(12) United States Patent
Barany et al.

(10) Patent No.: US 6,506,594 B1
(45) Date of Patent: *Jan. 14, 2003

(54) DETECTION OF NUCLEIC ACID SEQUENCE DIFFERENCES USING THE LIGASE DETECTION REACTION WITH ADDRESSABLE ARRAYS

(76) Inventors: Francis Barany, 450 E. 63rd St., Apt. #12C, New York, NY (US) 10021; Norman P. Gerry, 308 E. 83 St. 1C, New York, NY (US) 10028; Nancy E. Witowski, 7224 Tara Rd., Edina, MN (US) 55439; Joseph Day, 1147 Chess Dr., Foster City, CA (US) 94404; Robert P. Hammer, 4967 Tulane Dr., Baton Rouge, LA (US) 70808; George Barany, 1813 Prior Ave. N., Falcon Heights, MN (US) 55113

( * ) Notice: Subject to any disclaimer, the term of this patent is extended or adjusted under 35 U.S.C. 154(b) by 0 days.

This patent is subject to a terminal disclaimer.

(21) Appl. No.: 09/526,992

(22) Filed: Mar. 16, 2000

Related U.S. Application Data

(60) Provisional application No. 60/125,357, filed on Mar. 19, 1999.

(51) Int. Cl.$^7$ .......................... C12M 1/34; C12Q 1/68; C12P 19/34; C07H 21/02; C07H 21/04
(52) U.S. Cl. .................. 435/287.2; 435/6; 435/91.1; 435/287.1; 526/73.1; 526/24.3; 526/24.33
(58) Field of Search .................. 435/6, 91.1, 91.2, 435/183, 283.1, 287.1, 287.2, 288.4, 288.7; 436/94; 536/23.1, 24.3, 24.33, 25.3

(56) References Cited

U.S. PATENT DOCUMENTS

| | | | |
|---|---|---|---|
| 4,883,750 A | | 11/1989 | Whiteley |
| 4,988,617 A | | 1/1991 | Landegren |
| 5,143,854 A | | 9/1992 | Pirrung |
| 5,202,231 A | | 4/1993 | Drmanac |
| 5,324,633 A | | 6/1994 | Fodor |
| 5,405,783 A | | 4/1995 | Pirrung |
| 5,415,839 A | | 5/1995 | Zaun |
| 5,424,186 A | | 6/1995 | Fodor |
| 5,516,635 A | * | 5/1996 | Ekins et al. .................... 435/6 |
| 5,648,213 A | | 7/1997 | Reddy |
| 5,834,181 A | | 11/1998 | Shuber |
| 5,858,659 A | | 1/1999 | Sapolsky |
| 5,981,176 A | | 11/1999 | Wallace |
| 6,027,889 A | * | 2/2000 | Barany et al. .................. 435/6 |
| 6,143,495 A | * | 11/2000 | Lizardi et al. .................. 435/6 |

FOREIGN PATENT DOCUMENTS

| | | |
|---|---|---|
| EP | 0 601 714 A1 | 6/1994 |
| WO | WO 89/10977 | 11/1989 |
| WO | WO 90/15070 | 12/1990 |
| WO | WO 92/10588 | 6/1992 |
| WO | WO 92/16655 | 10/1992 |
| WO | WO 93/17126 | 9/1993 |
| WO | WO 93/20236 | 10/1993 |
| WO | WO 94/09022 | 4/1994 |
| WO | WO 94/11530 | 5/1994 |
| WO | WO 94/17206 | 8/1994 |
| WO | WO 94/17210 | 8/1994 |
| WO | WO 97/31256 A | 8/1997 |
| WO | WO-97/31256 * | 8/1997 |
| WO | WO 98/03673 A | 1/1998 |

OTHER PUBLICATIONS

Nonradioactive in situ hybridization manual from Boehringer Mannheim Biochemicals, p. 1, 1992.*

Nucleic acid hydbridization, a practical approach, p. 6, edited by Hames & Higgins, 1985. Published by IRL Press Limited, P. O. Box 1, Eynsham, Oxford OX 8 1JJ, England.*

Reynolds et al., "Analysis of Genetic Markers in Forensic DNA Samples Using the Polymerase Chain Reaction," *Anal. Chem.* 63:2–15 (1991).

Buyse et al., "Rapid DNA Typing of Class IIHLA Antigens Using the Polymerase Chain Reaction and Reverse Dot Blot Hybridization," *Tissue Antigens* 41:1–14 (1993).

Gyllensten et al., "PCR–Based HLA Class II Typing," *PCR Methods and Applications* 1:91–98 (1991).

Chamberlain et al., "Deletion Screening for the Duchenne Muscular Dystrophy Locus Via Multiplex DNA Amplification," *Nucleic Acids Research* 16(23):11141–11156 (1988).

Tsui, "Mutations and Sequence Variations Detected in the Cystic Fibrosis Transmembrane Conductance Regulator (CFTR) Gene: a Report from the Cystic Fibrosis Genetic Analysis Consortium," *Human Mutation* 1:197–203 (1992).

Hollstein et al., "53 Mutations in Human Cancers," *Science* 253:49–53 (1991).

Jou et al., "Deletion Detection in the Dystrophin Gene by Multiplex Gap Ligase Chain Reaction and Immunochromatographic Strip Technology," *Human Mutation* 5:86–93 (1995).

(List continued on next page.)

*Primary Examiner*—Ethan C. Whisenant
*Assistant Examiner*—Frank W Lu
(74) *Attorney, Agent, or Firm*—Nixon Peabody LLP

(57) ABSTRACT

The present invention describes a method for identifying one or more of a plurality of sequences differing by one or more single base changes, insertions, deletions, or translocations in a plurality of target nucleotide sequences. The ligation phase utilizes a ligation detection reaction between one oligonucleotide probe, which has a target sequence-specific portion and an addressable array-specific portion, and a second oligonucleotide probe, having a target sequence-specific portion and a detectable label. After the ligation phase, the capture phase is carried out by hybridizing the ligated oligonucleotide probes to a solid support with an array of immobilized capture oligonucleotides at least some of which are complementary to the addressable array-specific portion. Following completion of the capture phase, a detection phase is carried out to detect the labels of ligated oligonucleotide probes hybridized to the solid support. The ligation phase can be preceded by an amplification process. The present invention also relates to a kit for practicing this method, a method of forming arrays on solid supports, and the supports themselves.

75 Claims, 46 Drawing Sheets

OTHER PUBLICATIONS

Gibbs et al., "Detection of Single DNA Base Differences by Competitive Oligonucleotide Priming," *Nucleic Acids Research* 17(7):2437–2448 (1989).

Chehab e al., "Detection of Specific DNA Sequences by Fluorescence Amplification: A Color Complementation Assay," *Proc. Natl. Acad. Sci. USA*, 86:9178–9182(1989).

Landegren et al., "A Ligase–Mediated Gene Detection Technique", *Science* 241:1077–1080 (1988).

Nickerson et al., "Automated DNA Diagnosis Using an ELISA–Based Oligonucleotide Ligation Assay," *Proc. Natl. Acad. Sci. USA*, 87:8923–8927 (1990).

Wu et al., "The Ligation Amplification Reaction (LAR)–Amplification of Specific DNA Sequences Using Sequential Rounds of Template–Dependent Ligation," *Genomics* 4:560–569 (1989).

Chetverin et al., "Sequencing of Pools of Nucleic Acids on Oligonucleotide Arrays," *BioSystems* 30:215–231 (1993).

Kuznetsova et al., "DNA Sequencing by Hybridization with Oligonucleotides Immobilized in a Gel," *Mol. Biol. (Mosk-)(Russia)* 28(2):290–299 (1994) (English abstract attached).

Livshits et al., "Dissociation of Duplexes Formed by a Hybridization of DNA with Gel–Immobilized Oligonucleotides," *Journal of Biomolecular Structure & Dynamics* 11(4): 783–795 (1994).

Pease et al., "Light–Generated Oligonucleotide Arrays for Rapid DNA Sequence Analysis," *Proc. Natl. Acad. Sci. USA* 91:5022–5026 (1994).

Beattie et al., "Advances in Genosensor Research," *Clin. Chem.* 41(5) 700–706 (1995).

Southern et al., "Analyzing and Comparing Nucleic Acid Sequences by Hybridization to Arrays of Oligonucleotides: Evaluation using Experimental Models, " *Genomics*, 13:1008–1017 (1992).

Fodor et al., "Multiplexed Biochemical Assays with Biological Chips," *Nature*, 364:555–556 (1993).

Khrapko et al., "A Method for DNA Sequencing by Hybridization with Oligonucleotide Matrix," *J. DNA Seq. Map.*, 1:375–388 (1991).

Van Ness et al., "A Versatile Solid Support System for Oligodeoxynucleotide Probe–based Hybridization Assays," *Nucleic Acids Res.*, 19:3345–3350 (1991).

Zhang et al., "Single–base Mutational Analysis of Cancer and Genetic Diseases Using Membrane Bound Modified Oligonucleotides," *Nucleic Acids Res.* 19:3929–3933 (1991).

R.J. Lipshutz et al., "Using Oligonucleotide Probe Arrays to Assess Genetic Diversity," *Biotechniques* 19:442–447 (1995).

Maskos et al., "A Study of Oligonucleotide Reassociation Using Large Arrays of Oligonucleotides Synthesised on a Glass Support," *Nucleic Acids Res.*, 21:4663–4669 (1993).

Maskos et al., "A Novel Method for the Analysis of Multiple Sequence Variants by Hybridization to Oligonucleotides," *Nucleic Acids Res.*, 21:2267–2268 (1993).

Timofeev et al., "Regioselective Immobilization of Short Oligonucleotides to Acrylic Copolymer Gels," *Nucleic Acids Res.* 24:3142–3148 (1996).

Guo et al., Direct Fluorescence Analysis for Genetic Polymorphisms by Hybridization with Oligonucleotide Arrays on Glass Supports, *Nucleic Acids Res.* 22:5456–5465 (1994).

Hacia et al., "Detection of Heterozygous Mutations in BRCA1 Using High Density Oligonucleotide Arrays and Two–Colour Fluorescence Analysis," *Nat. Genet.* 14:441–447 (1996).

Chee et al., "Accessing Genetic Information with High–Density DNA Arrays," *Science* 274:610–614 (1996).

Schena et al., "Parallel Human Genome Analysis: Microarray–Based Expression Monitoring of 1000 Genes," *Proc. Natl. Acad. Sci. USA* 93:10614–10619 (1996).

Shalon et al., "A DNA Microarray System for Analyzing Complex DNA Samples Using Two–Color Fluorescent Probe Hybridization," *Genome Res.* 6:639–645 (1996).

Cronin et al., "Cystic Fibrosis Mutation Detection by Hybridization to Light–Generated DNA Probe Arrays," *Human Mutation* 7:244–255 (1996).

Wang et al., "Large–Scale Identification, Mapping, and Genotyping of Single–Nucleotide Polymorphisms in the Human Genome," *Science* 280:1077–1082 (1998).

Southern, "DNA Chips: Analyzing Sequence by Hybridization to Oligonucleotides on a Large Scale," *Trends in Genet.* 12(3):110–115 (1996).

Drobyshev et al., "Sequence Analysis by Hybridization with Oligonucleotide Microchip: Identification of α–Thalassemia Mutations," *Gene* 188:45–52 (1997).

Yershov et al., "DNA Analysis and Diagnostic on Oligonucleotide Microchips," *Proc. Natl. Acad. Sci. USA* 93:4913–4918 (1996).

Parinov et al., "DNA Sequencing by Hybridization to Microchip Octa– and Decanuleotides Extended by Stacked Pentanucleotides," *Nucleic Acids Res.* 24:2998–3004 (1996).

Kozal et al., "Extensive Polymorphisms Observed in HIV–1 Clade B Protease Gene Using High–Density Oligonucleotide Arrays," *Nature Medicine* 2:753–759 (1996).

Grossman et al., "High–Density Multiplex Detection of Nucleic Acid Sequences: Oligonucleotide Ligation Assay and Sequence–Coded Separation," *Nucleic Acids Research* 22(21):4527–4534 (1994).

Jin et al., "Alternating Current Impedance Characterization of the Structure of Alkylsiloxane Self–Assembled Monolayers on Silicon," *Langmuir* 10:2662–2671 (1994).

Cheng et al., "In Situ Attenuated Total Reflectance Fourier Transform Infrared Spectroscopy of Carboxylate–Bearing, Siloxane–Anchored, Self–Assembled Monolayers: A Study of Carboxylate Reactivity and Acid–Base Properties," *Langmuir*, 11:1190–1195 (1995).

Telenti et al., "Competitive Polymerase Chain Reaction Using an Internal Standard: Application to the Quantitation of Viral DNA," *Journal of Virological Methods* 39:259–268 (1992).

Wiedman et al., "Ligase Chain Reaction (LCR)—Overview and Applications," *PCR Methods & Appl.* 3:551–564 (1994).

Nikiforov et al.,"Genetic Bit Analysis: A Solid Phase Method for Typing Single Nucleotide Polymorphisms," *Nucleic Acids Res.* 22(20):4167–4175 (1994).

Janssen et al., "Evaluation of the DNA Fingerprinting Method AFLP as a New Tool in Bacterial Taxonomy," *Microbiology* 142:1881–1893 (1996).

Belgrader et al., "A Multiplex PCR–Ligase Detection Reaction Assay for Human Identity Testing," *Genome Science & Tech.* 1:77–87 (1996).

Weber et al., "Abundant Class of Human DNA Polymorphisms Which Can Be Typed Using the Polymerase Chain Reaction," *Amer. J. Hum. Genet.* 44:388–396 (1989).

Barany et al., "Cloning, Overexpression, And Nucleotide Sequence Of A Thermostable DNA Ligase Gene," *Gene* 109:1–11 (1991).

Barany, "Genetic Disease Detection and DNA Amplification Using Cloned Thermostable Ligase," *Proc. Natl. Acad. Sci. USA* 88:189–193 (1991).

Barany, "The Ligase Chain Reaction in a PCR World," *PCR Methods and Applications* 1:5–16 (1991).

Day et al., "Detection Of Steroid 21–Hydroxylase Alleles Using Gene–Specific PCR and a Multiplexed Ligation Detection Reaction," *Genomics* 29:152–162 (1995).

Day et al., "Identification of Non–Amplifying CYP21 Genes When Using PCR–Based Diagnosis of 21–Hydroxylase Deficiency in Congenital Adrenal Hyperplasia (CAH) Affected Pedigrees," *Hum. Mol. Genet.* 5(12):2039–2048 (1996).

Khanna et al., "Multiplex PCR/LDR for Detection of K–ras Mutations in Primary Colon Tumors," *Oncogene* 18:27–38 (1999).

Heller et al., "Discovery and Analysis of Inflammatory Disease–Related Genes Using cDNA Microarrays," *Proc. Nat'l. Acad. Sci. USA* 94:2150–2155 (1997).

Gerry et al., "Universal DNA Microarray Method for Multiplex Detection of Low Abundance Point Mutations," *J. Mol. Biol.* 292:251–262 (1999).

Reed et al., "Chromosome–Specific Microsatellite Sets for Fluorescence–Based, Semi–Automated Genome Mapping," *Nature Genetics* 7:390–395 (1994).

Lysov et al., "DNA Sequencing by Hybridization to Oligonucleotide Matrix. Calculation of Continuous Stacking Hybridization Efficiency," *Journal of Biomolecular Structure & Dynamics* 11(4):797–812 (1994).

Tong et al., "Biochemical Properties of a High Fidelity DNA Ligase from Thermus species AK16D," *Nucleic Acids Research* 27(3):788–794 (1999).

* cited by examiner

PCR/LDR

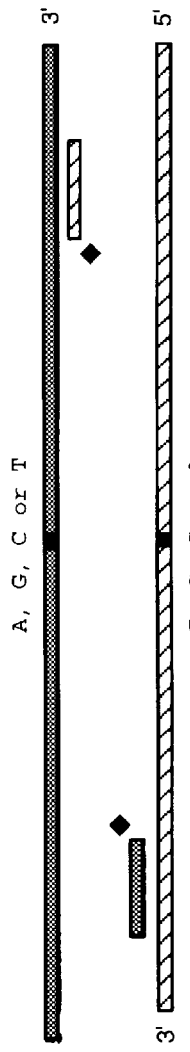

1. PCR amplify region(s) containing mutations using primers, dNTPs and Taq polymerase. ◆

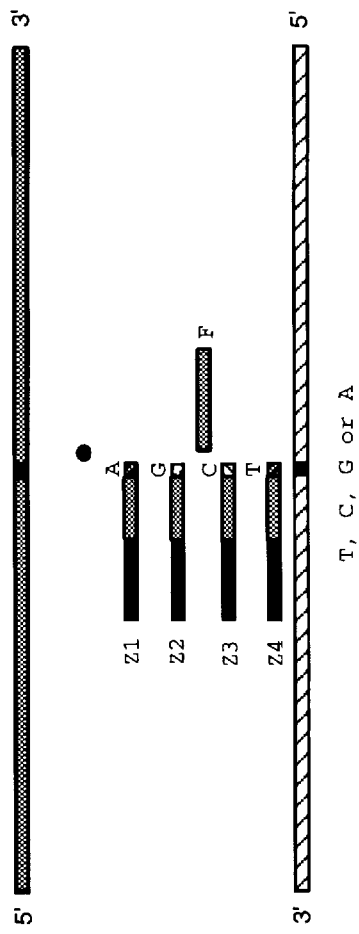

2. Perform LDR using allele-specific LDR primers and thermostable ligase. ● Allele specific oligonucleotides ligate to common oligonucleotides only when there is perfect complementarity at the junction.

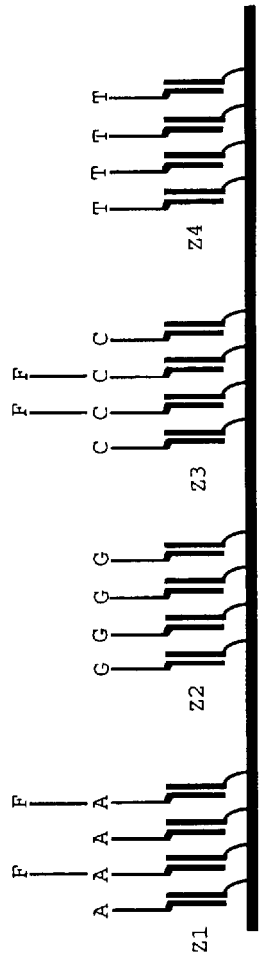

3. Capture fluorescent products on addressable array and quantify each allele.

*FIG. 4*

PCR/LDR : Nearby alleles

1. PCR amplify region(s) containing mutations using primers, dNTPs and *Taq* polymerase. ◆

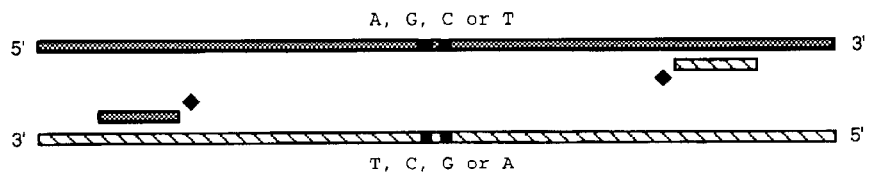

2. Perform LDR using allele-specific LDR primers and thermostable ligase. ● Allele specific oligonucleotides ligate to common oligonucleotides only when there is perfect complementarity at the junction.

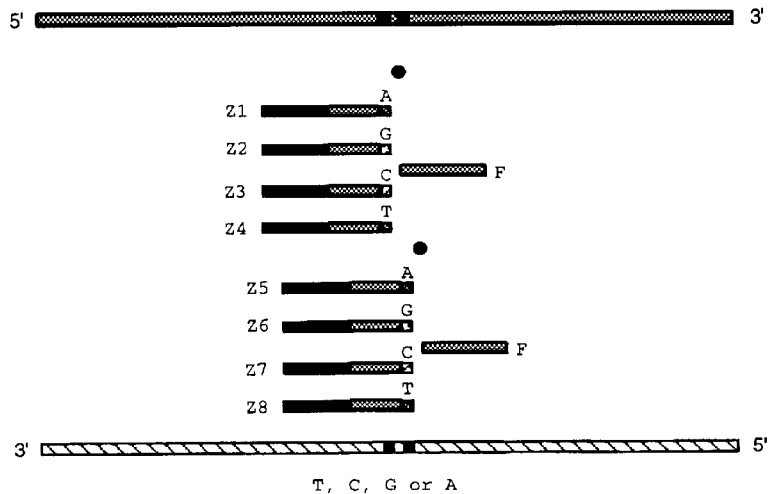

3. Capture fluorescent products on addressable array and quantify each allele.

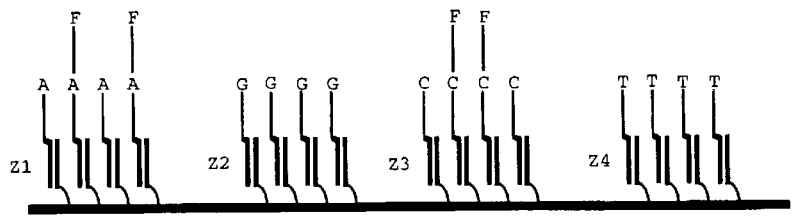

Heterozygous: A and C alleles.

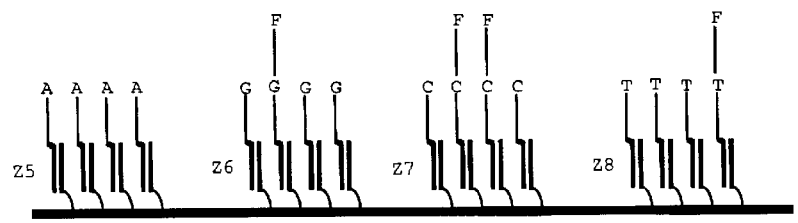

Heterozygous: G, C, and T alleles.

*FIG. 5*

PCR/ LDR : Insertions and Deletions

1. PCR amplify region(s) containing mutations using primers, dNTPs and Taq polymerase.◆

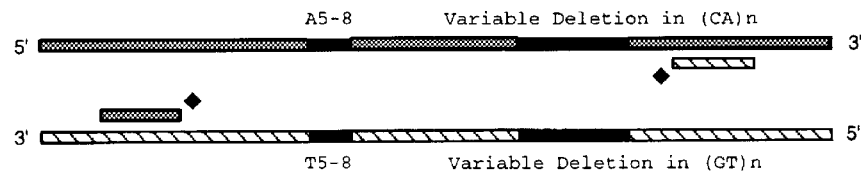

2. Perform LDR using allele-specific LDR primers and thermostable ligase. ● Allele specific oligonucleotides ligate to common oligonucleotides only when there is perfect complementarity at the junction.

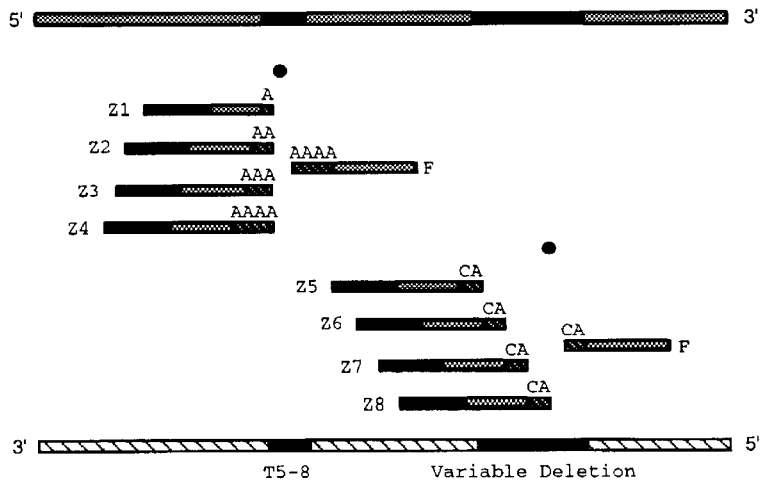

3. Capture fluorescent products on addressable array and quantify each allele.

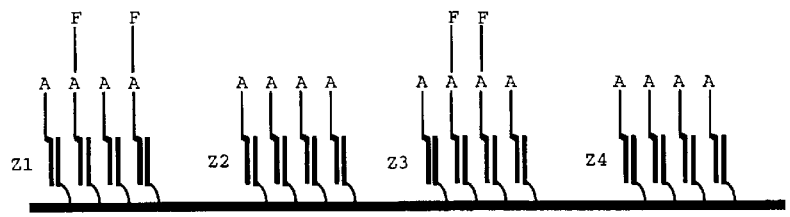

Heterozygous: A5 and A7 alleles.

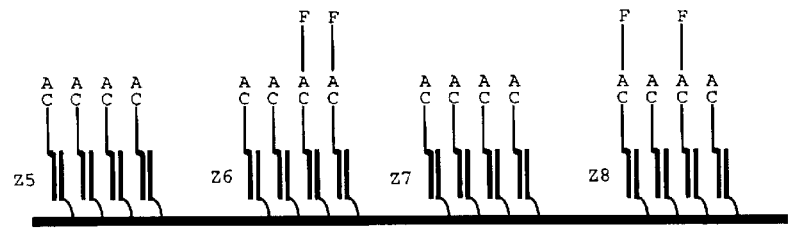

Heterozygous: (CA)5 and (CA)3 alleles.

*FIG. 6*

PCR/LDR : Adjacent alleles, cancer detection

1. PCR amplify region(s) containing mutations using primers, dNTPs and *Taq* polymerase. ◆

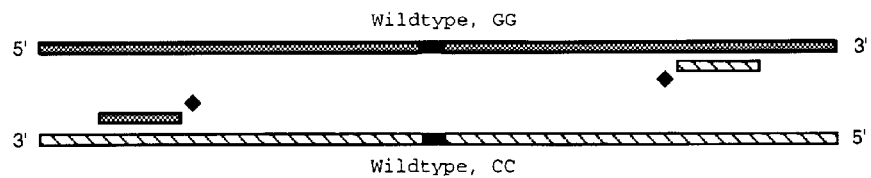

2. Perform LDR using allele-specific LDR primers and thermostable ligase. ● Allele specific oligonucleotides ligate to common oligonucleotides only when there is perfect complementarity at the junction.

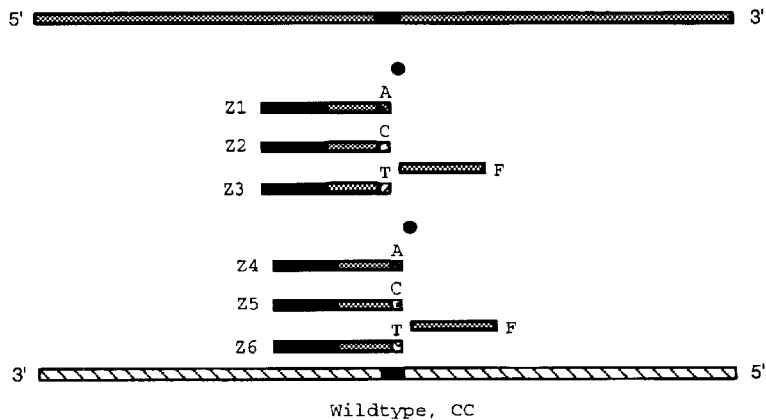

3. Capture fluorescent products on addressable array and quantify each allele.

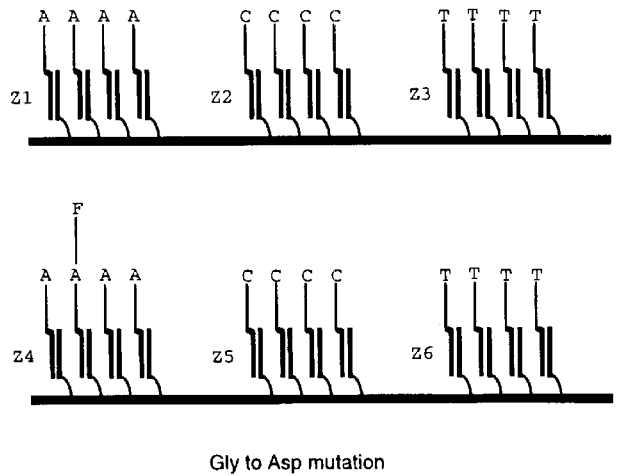

Gly to Asp mutation

*FIG. 7*

PCR/ LDR : Nearby alleles

1. PCR amplify region(s) containing mutations using primers, dNTPs and *Taq* polymerase. ◆

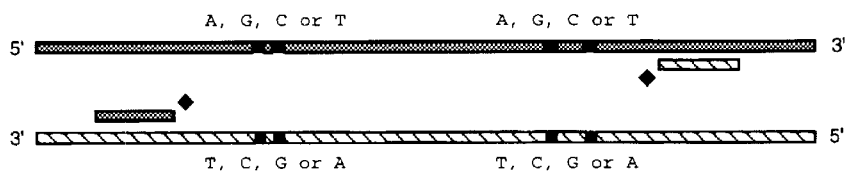

2. Perform LDR using allele-specific LDR primers and thermostable ligase. ● Allele specific oligonucleotides ligate to common oligonucleotides only when there is perfect complementarity at the junction.

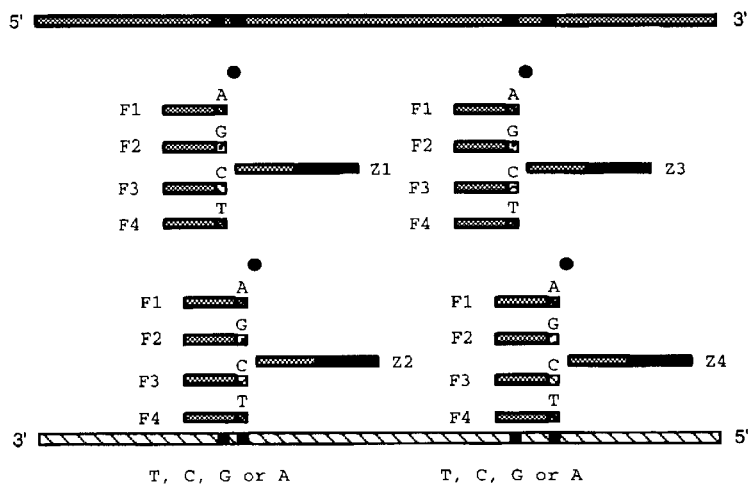

3. Capture fluorescent products on addressable array and quantify each allele.

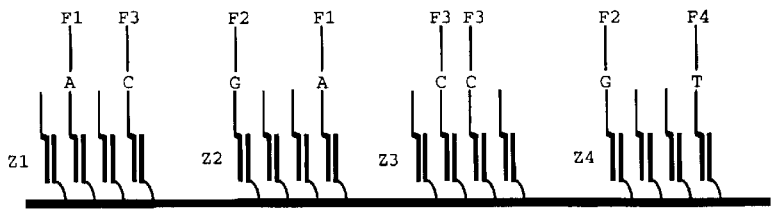

Heterozygous: A and C alleles.    Heterozygous: A and G alleles.    Homozygous: C allele.    Heterozygous: G and T alleles.

*FIG. 8*

PCR/LDR : Adjacent and Nearby alleles

1. PCR amplify region(s) containing mutations using primers, dNTPs and *Taq* polymerase. ♦

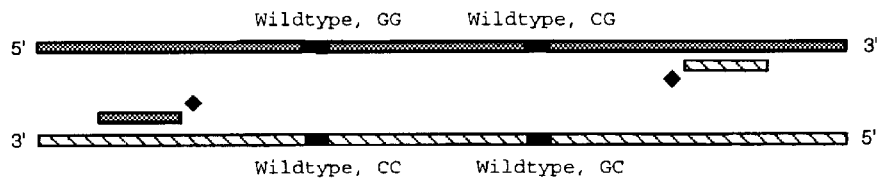

2. Perform LDR using allele-specific LDR primers and thermostable ligase. ● Allele specific oligonucleotides ligate to common oligonucleotides only when there is perfect complementarity at the junction.

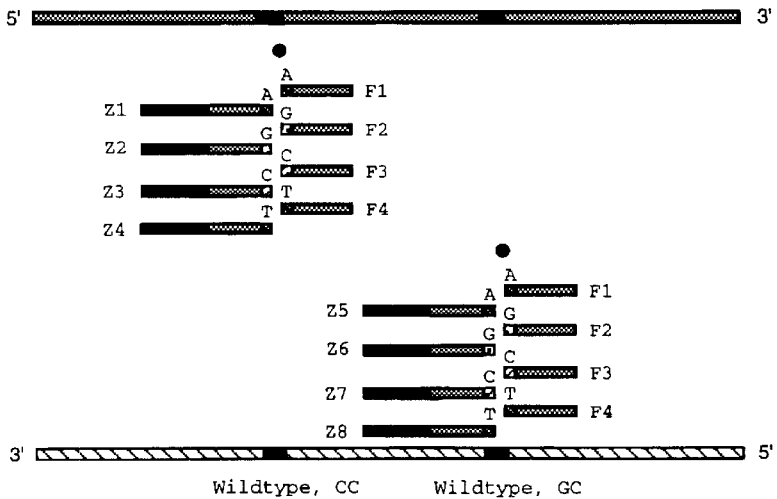

3. Capture fluorescent products on addressable array and quantify each allele.

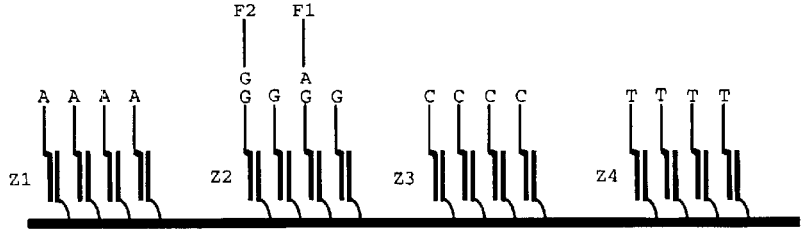

Heterozygous: Gly and Glu alleles.

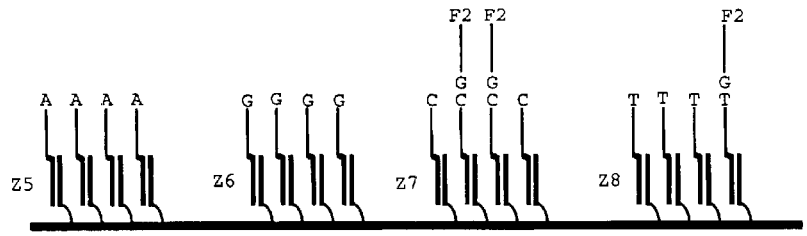

Heterozygous: Arg and Trp alleles.

*FIG. 9*

PCR/ LDR : All alleles of a single codon

1. PCR amplify region(s) containing mutations using primers, dNTPs and *Taq* polymerase. ◆

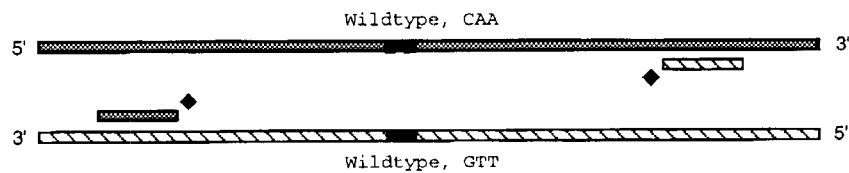

2. Perform LDR using allele-specific LDR primers and thermostable ligase. ● Allele specific oligonucleotides ligate to common oligonucleotides only when there is perfect complementarity at the junction.

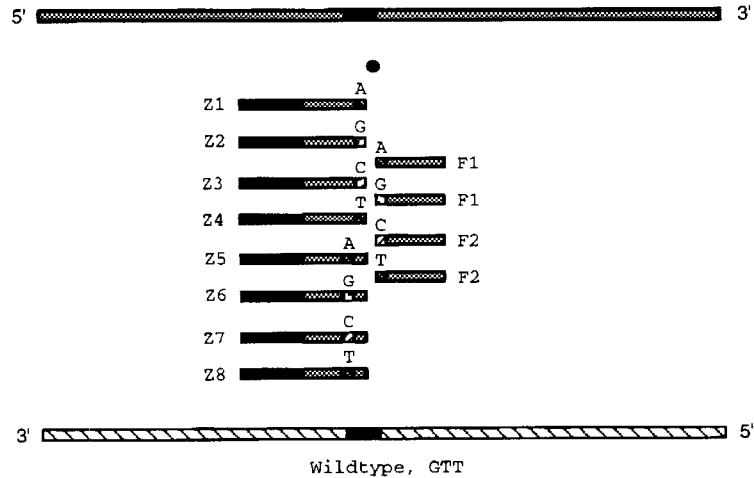

3. Capture fluorescent products on addressable array and quantify each allele.

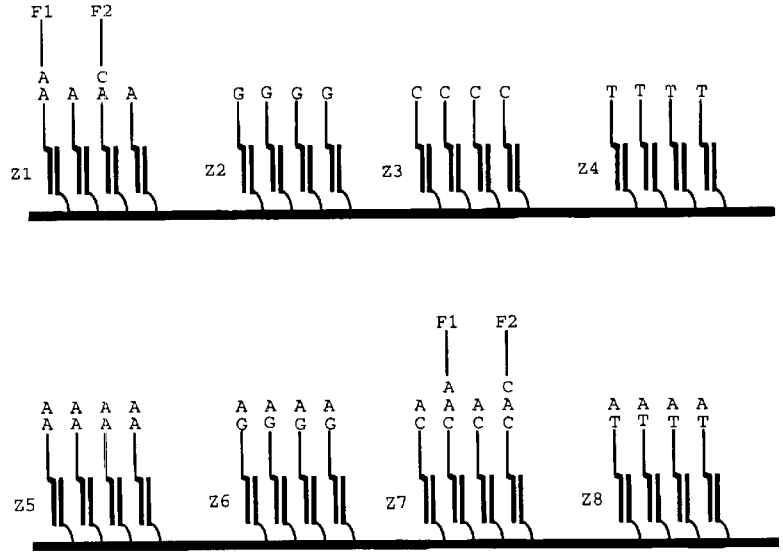

Heterozygous: Gln and His alleles.

*FIG. 10*

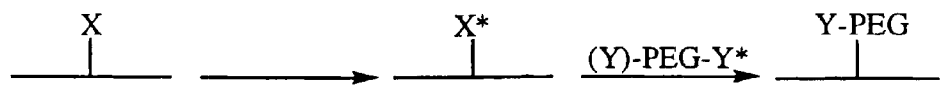

| X, Y | = | -OH<br>-CO$_2$H<br>-NH$_2$ | X*, Y* | = | -O(C=O)Z<br>-O(C=S)Z<br>-CO$_2$H |
|---|---|---|---|---|---|
| (Y) | = | W-NH- | | | -(C=O)Z<br>-NH$_2$<br>-N=C=O |

W = protecting group, e.g. Boc, Fmoc
Z = activating group, e.g. imidazole (Im), p-nitrophenol (OPnp),
   hydroxysuccinimide (OSu), pentafluorophenol (OPfp)
PEG = oligo or poly(ethylene glycol), backbone (CH$_2$CH$_2$O)$_n$ n = 6 to 200
   (can also be grown by anionic polymerization with 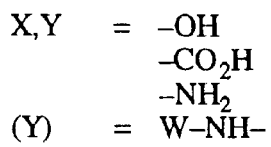)
WSC = water soluble carbodiimide

**Functional group transformations/activation (as needed), X → X*, Y → Y***

-OH → -O(CH$_2$)$_n$CO$_2$H     n = 1, 2
-OH → -O(C=O)NHCH$_2$CO$_2$H
-OH → -O(C=O)CH$_2$NH$_2$
-OH → -O(C=O)Im
-OH → -O(C=S)SCH$_2$(C=O)NH$_2$
-CO$_2$H → -(C=O)NH(CH$_2$)$_n$NH$_2$   n = 2,6
-CO$_2$H → -(C=O)Z
-NH$_2$ → -NH(C=O)(CH$_2$)$_n$CO$_2$H   n = 2, 3

**Covalent linkage, X* + Y***

-CO$_2$H + H$_2$N- + WSC + HOSu → -(C=O)NH-
-OH + Im(C=O)Im + H$_2$N- → -O(C=O)NH-

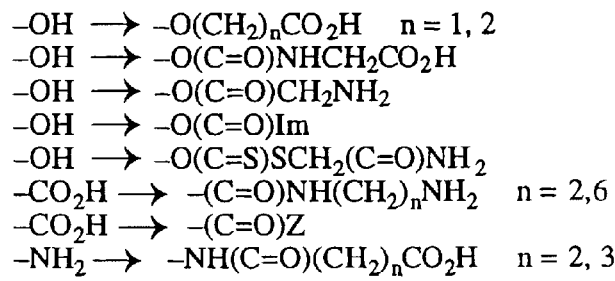

-OH + O=C=N- → -O(C=O)NH-
-O(C=S)SCH$_2$(C=O)NH$_2$ + H$_2$N- → -O(C=S)NH-
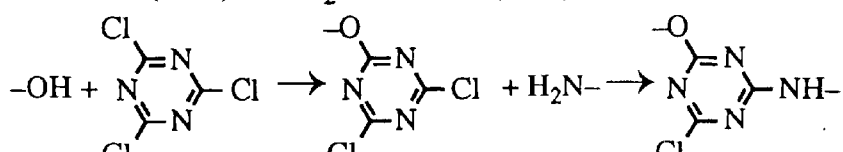

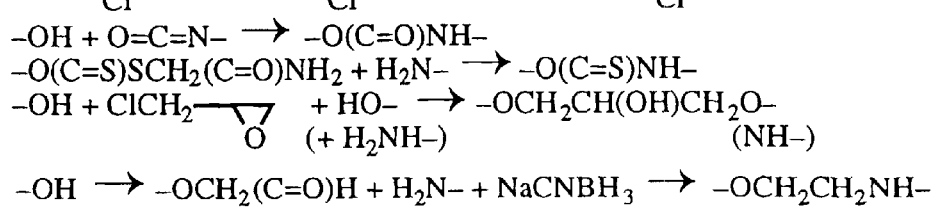

FIG. 11

FIG. 15A
1st addition of unique 24mers.
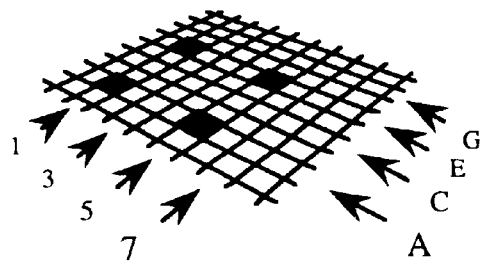
FIG. 15B
2nd addition of unique 24mers.
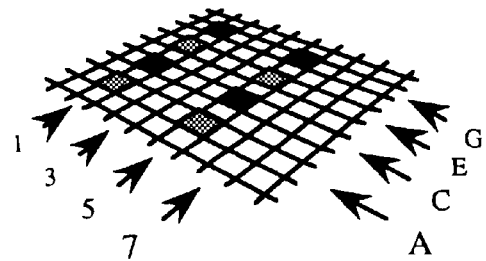
FIG. 15C
3rd addition of unique 24mers.
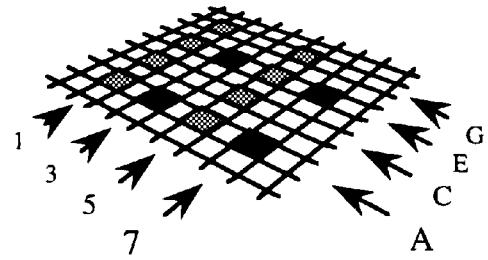
FIG. 15D
4th addition of unique 24mers.
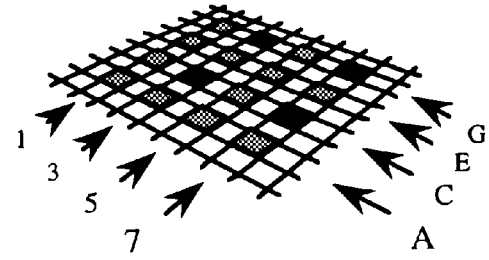
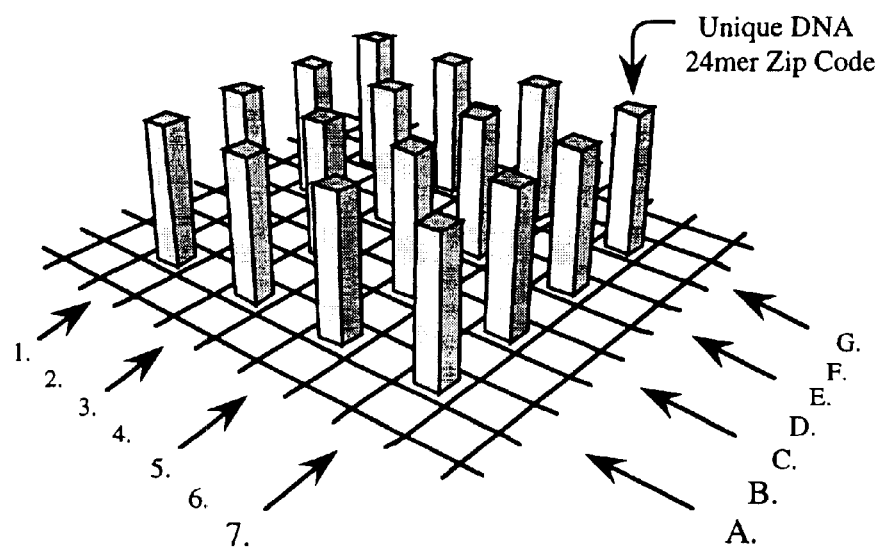
FIG. 15E

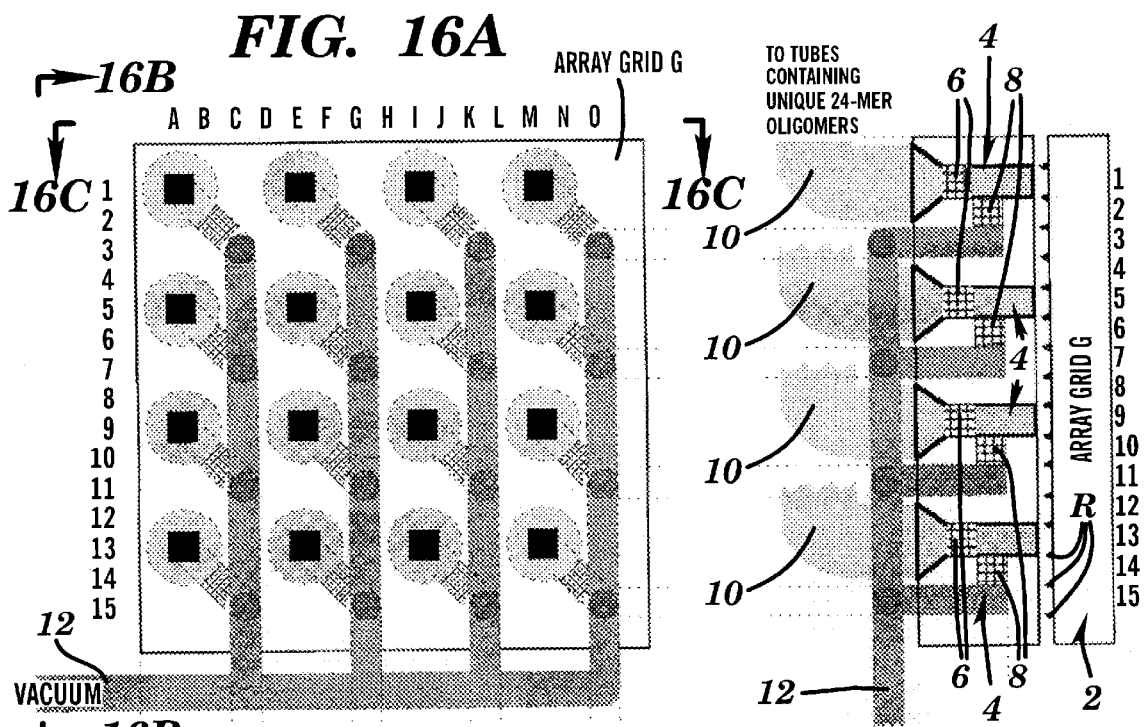
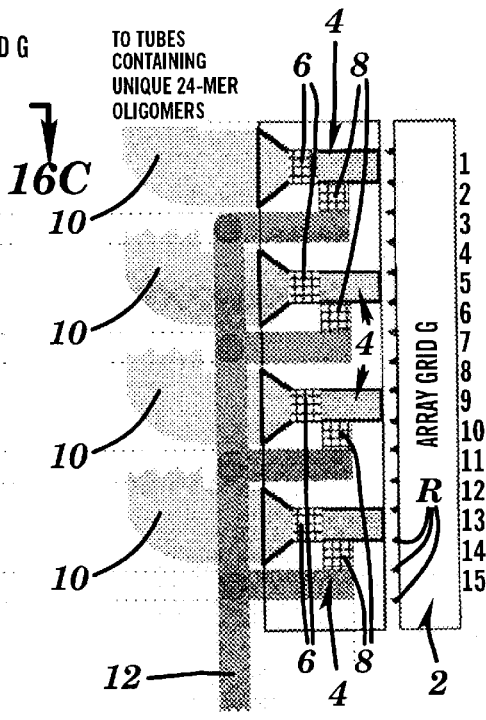
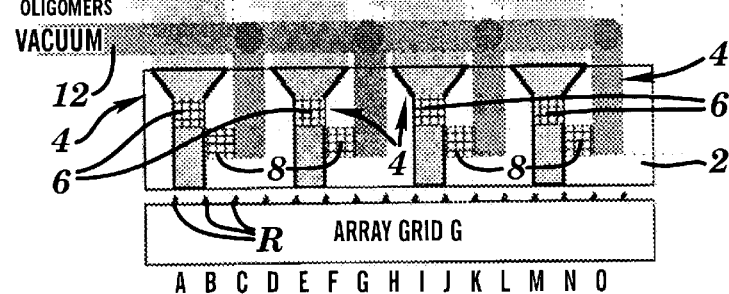
FIG. 16A
FIG. 16B
FIG. 16C

FIG. 17

1st Tetramer addition (columns)

| 1 | 2 | 3 | 4 | 5 |
|---|---|---|---|---|
| 1 | 2 | 3 | 4 | 5 |
| 1 | 2 | 3 | 4 | 5 |
| 1 | 2 | 3 | 4 | 5 |
| 1 | 2 | 3 | 4 | 5 |

FIG. 18A

2nd Tetramer addition (rows)

| 6 | 6 | 6 | 6 | 6 |
|---|---|---|---|---|
| 5 | 5 | 5 | 5 | 5 |
| 4 | 4 | 4 | 4 | 4 |
| 3 | 3 | 3 | 3 | 3 |
| 2 | 2 | 2 | 2 | 2 |

FIG. 18B

3rd Tetramer addition (columns)

| 3 | 4 | 5 | 6 | 1 |
|---|---|---|---|---|
| 3 | 4 | 5 | 6 | 1 |
| 3 | 4 | 5 | 6 | 1 |
| 3 | 4 | 5 | 6 | 1 |
| 3 | 4 | 5 | 6 | 1 |

FIG. 18C

4th Tetramer addition (rows)

| 2 | 2 | 2 | 2 | 2 |
|---|---|---|---|---|
| 1 | 1 | 1 | 1 | 1 |
| 6 | 6 | 6 | 6 | 6 |
| 5 | 5 | 5 | 5 | 5 |
| 4 | 4 | 4 | 4 | 4 |

FIG. 18D

5th Tetramer addition (columns)

| 6 | 1 | 2 | 3 | 4 |
|---|---|---|---|---|
| 6 | 1 | 2 | 3 | 4 |
| 6 | 1 | 2 | 3 | 4 |
| 6 | 1 | 2 | 3 | 4 |
| 6 | 1 | 2 | 3 | 4 |

FIG. 18E

6th Tetramer addition (rows)

| 3 | 3 | 3 | 3 | 3 |
|---|---|---|---|---|
| 2 | 2 | 2 | 2 | 2 |
| 1 | 1 | 1 | 1 | 1 |
| 6 | 6 | 6 | 6 | 6 |
| 5 | 5 | 5 | 5 | 5 |

FIG. 18F

Addressable array with full length PNA 24mers

| 1-6-3-2-6-3 | 2-6-4-2-1-3 | 3-6-5-2-2-3 | 4-6-6-2-3-3 | 5-6-1-2-4-3 |
|---|---|---|---|---|
| 1-5-3-1-6-2 | 2-5-4-1-1-2 | 3-5-5-1-2-2 | 4-5-6-1-3-2 | 5-5-1-1-4-2 |
| 1-4-3-6-6-1 | 2-4-4-6-1-1 | 3-4-5-6-2-1 | 4-4-6-6-3-1 | 5-4-1-6-4-1 |
| 1-3-3-5-6-6 | 2-3-4-5-1-6 | 3-3-5-5-2-6 | 4-3-6-5-3-6 | 5-3-1-5-4-6 |
| 1-2-3-4-6-5 | 2-2-4-4-1-5 | 3-2-5-4-2-5 | 4-2-6-4-3-5 | 5-2-1-4-4-5 |

FIG. 18G

FIG. 20A
1st Tetramer additions
(columns)
FIG. 20B
2nd Tetramer additions
(rows)
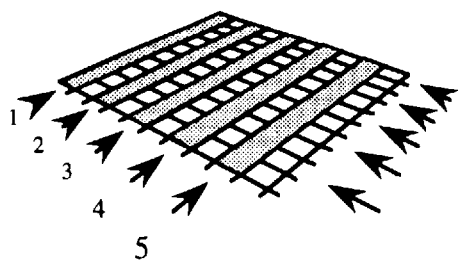
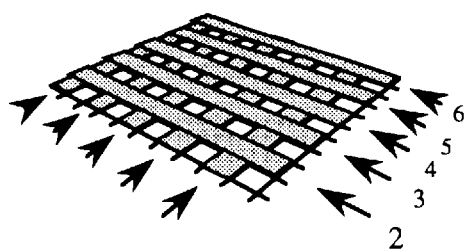
Unique PNA 24mer Zip
Code: 5-6-1-2-4-3.
Common PNA 12mer:
6-2-3. Does not hybridize.
1st Step  2nd Step
3rd Step  4th Step
5th Step  6th Step
FIG. 20C

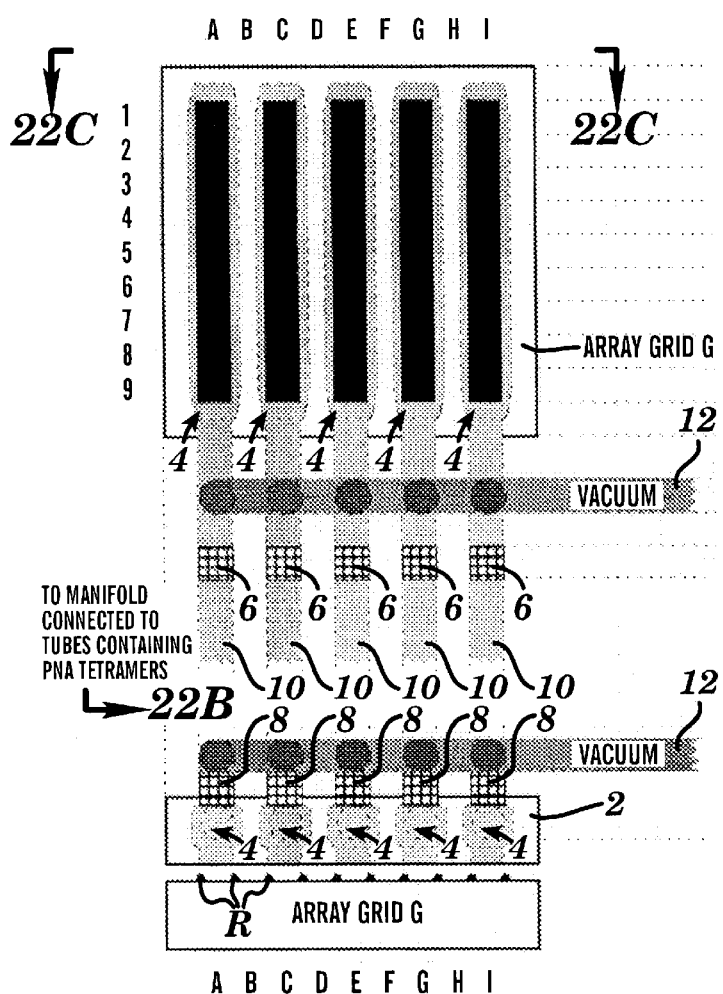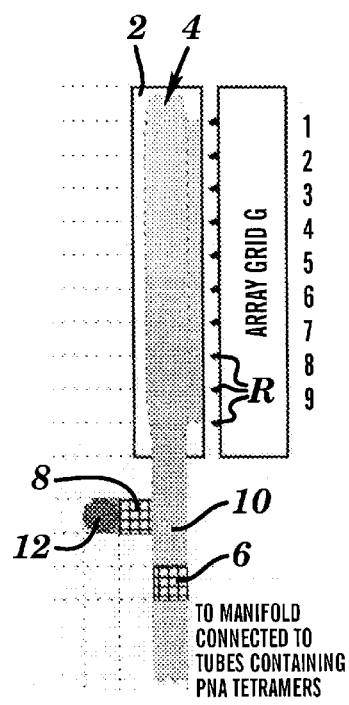
FIG. 22A
FIG. 22B
FIG. 22C

FIG. 23A
1st Tetramer additions
(columns)
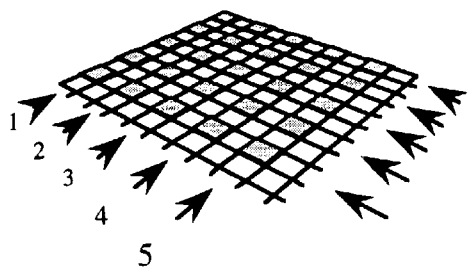
FIG. 23B
2nd Tetramer additions
(rows)
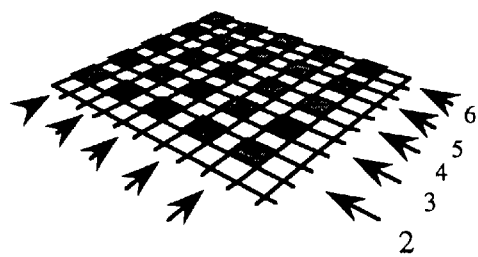
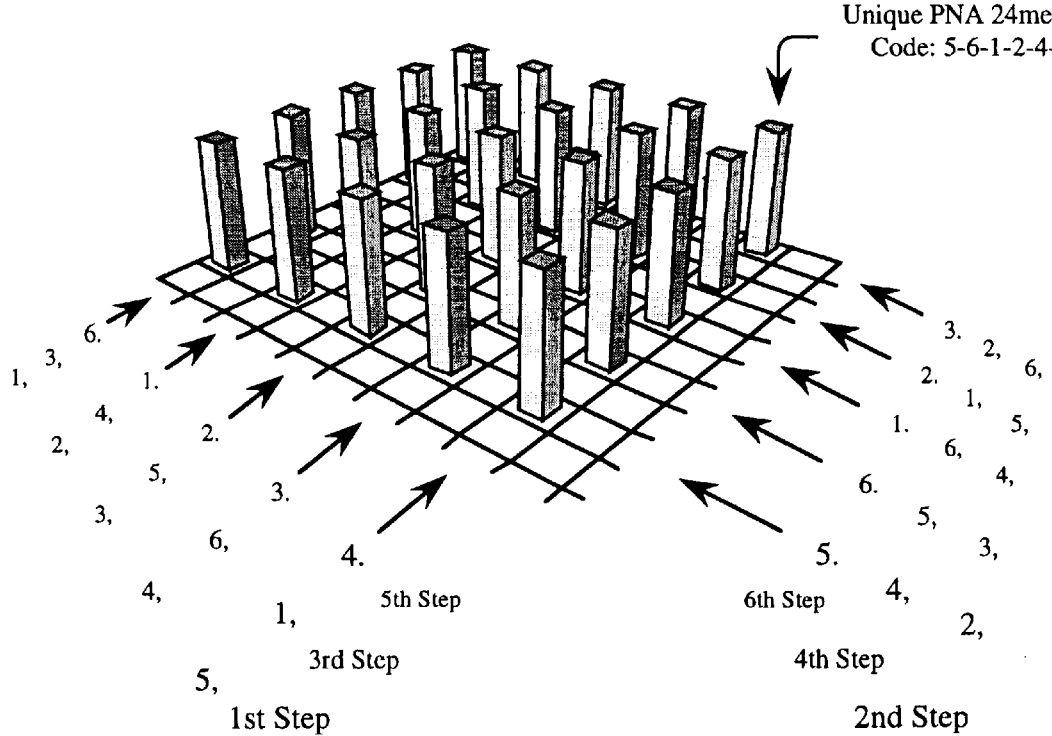
FIG. 23C

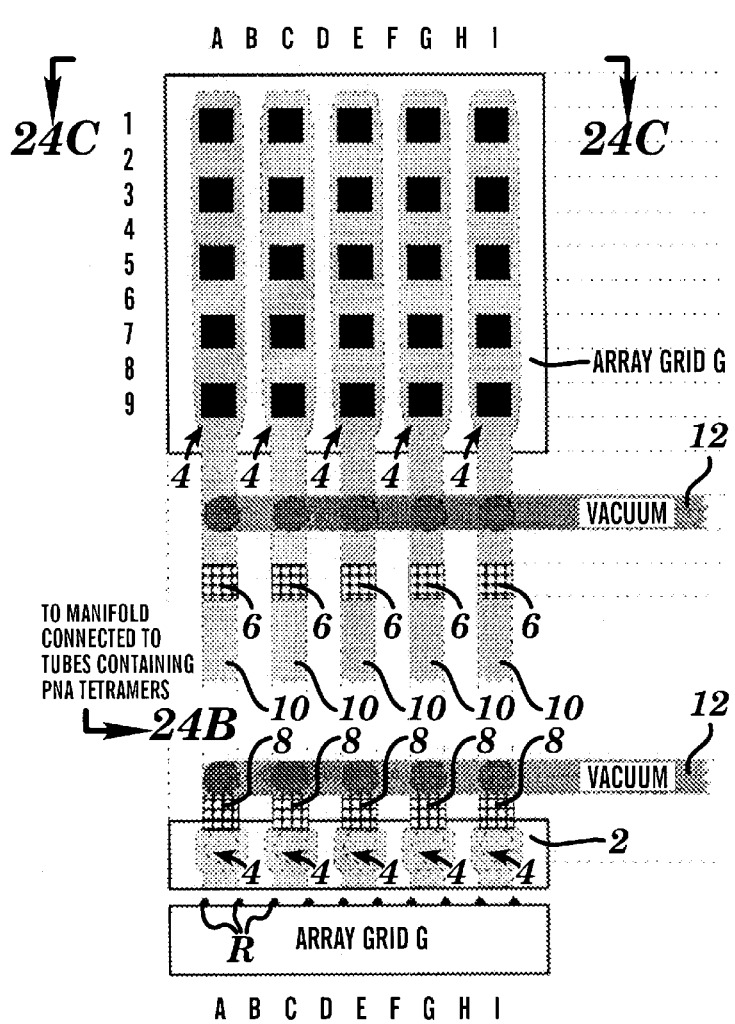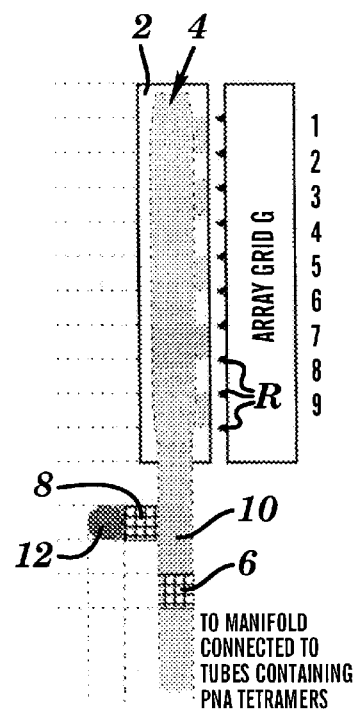
FIG. 24A
FIG. 24B
FIG. 24C

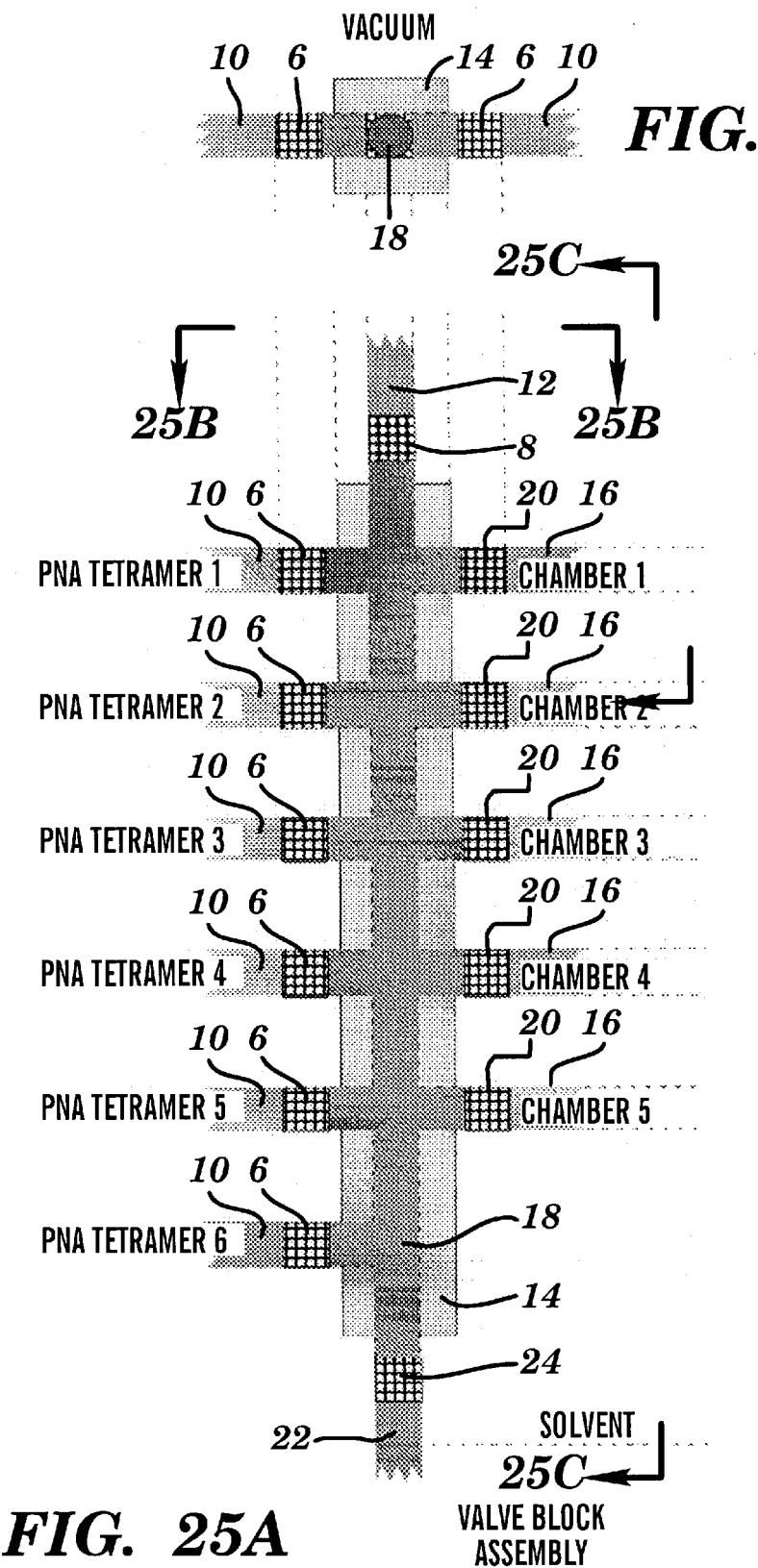
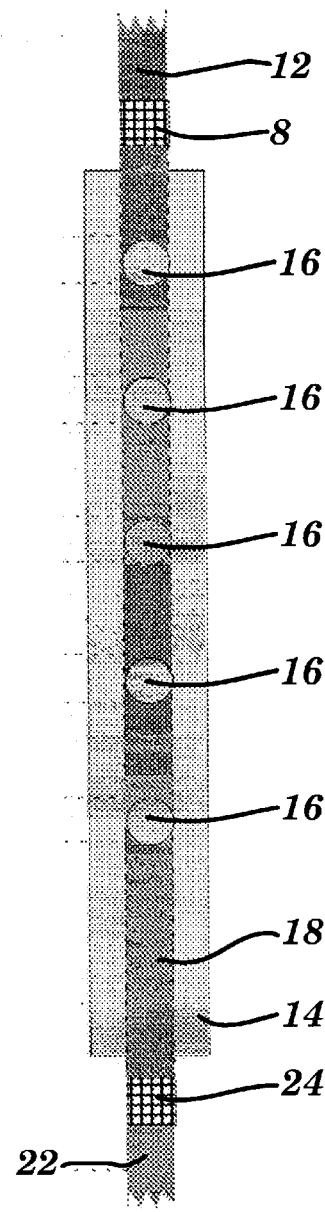
*FIG. 25A*  *FIG. 25B*  *FIG. 25C*
6 INPUTS AND 5 OUTPUTS

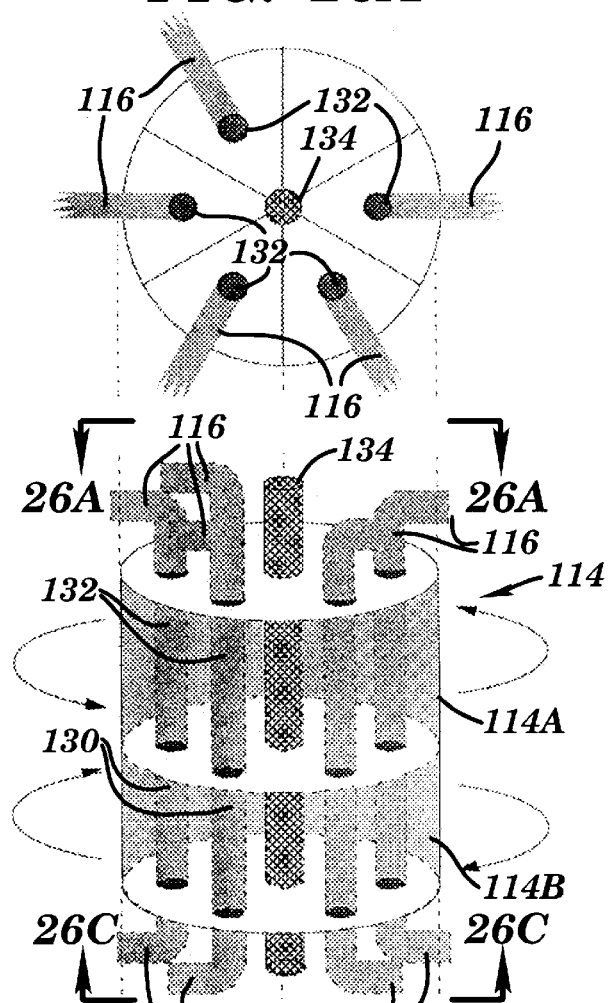
FIG. 26A
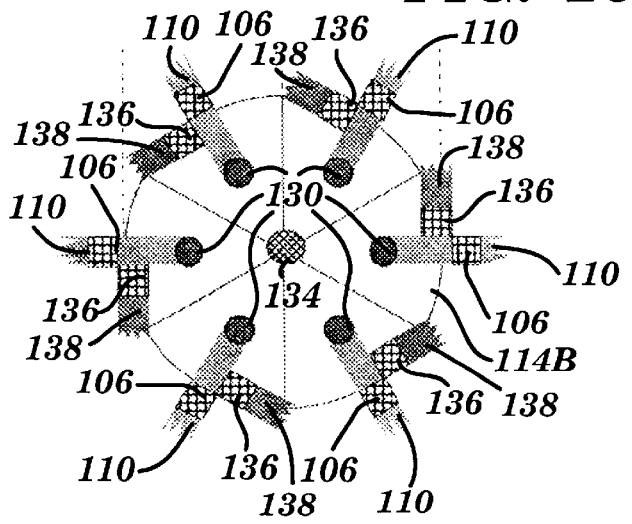
FIG. 26B
FIG. 26C
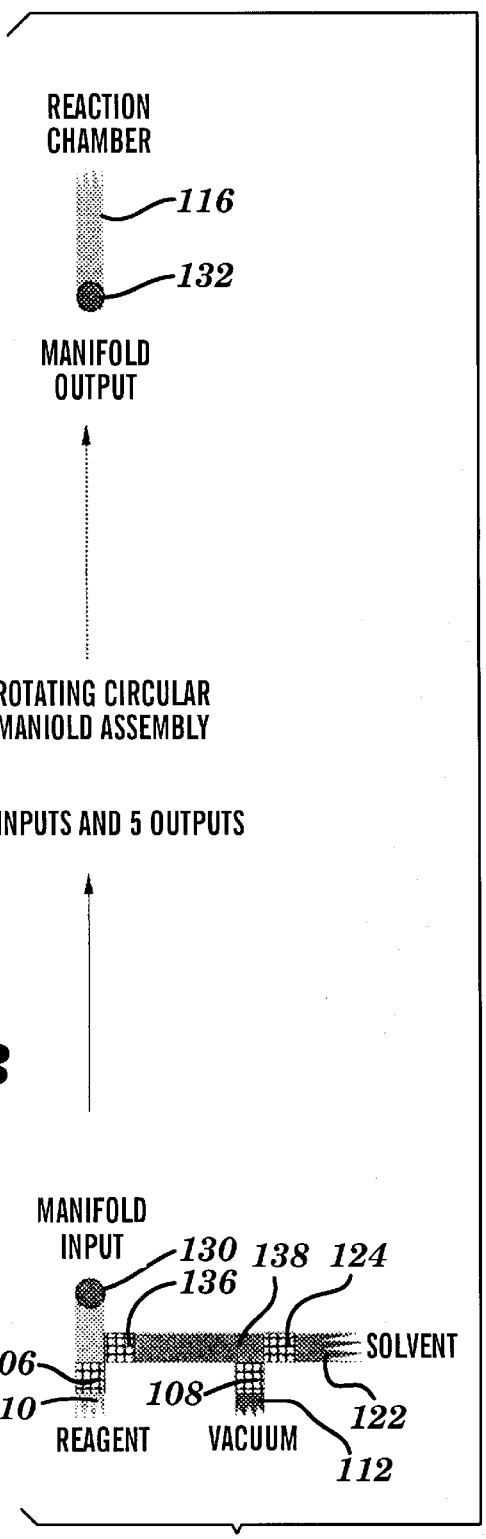
FIG. 26D

-COOH; PROBE 12

-COOH; PROBE 14

-NH2; PROBE 12

-NH2; PROBE 14

FIG. 28

2% EGDMA

2% HDDMA

4% EGDMA

*FIG. 29*

| Mutation | | LDR primer alignment | | | |
|---|---|---|---|---|---|
| BRCA1 exon 2 | WT | Fam ——— GAG | | | |
| 185delAG | MT | Tet ——— G | TG ——— A1 | | |
| BRCA1 exon 20 | WT | Fam ——— TCCC | | | |
| 5382insC | MT | Tet ——— TCCCC | A ——— A5 | | |
| BRCA2 exon 11 | WT | Fam ——— AGT | | | |
| 6174delT | MT | Tet ——— AG | GGA ——— A3 | | |

FIG. 40

| Mutation | LDR primer alignment | | | | |
|---|---|---|---|---|---|
| BRCA1 exon 2 | WT | A2 ———— GAG | | | |
| 185delAG | MT | A4 ———— G | TG ———— Fam | | |
| | | | | | |
| BRCA1 exon 20 | WT | A12 ———— TCCC | | | |
| 5382insC | MT | A13 ———— TCCCC | A ———— Fam | | |
| | | | | | |
| BRCA2 exon 11 | WT | A14 ———— AGT | | | |
| 6174delT | MT | A15 ———— AG | GGA ———— Fam | | |

DETECTION OF NUCLEIC ACID SEQUENCE DIFFERENCES USING THE LIGASE DETECTION REACTION WITH ADDRESSABLE ARRAYS

This application claims the benefit of U.S. Provisional Patent Application Serial No. 60/125,357, filed Mar. 19, 1999.

This invention was developed with government funding under National Institutes of Health Grant Nos. GM-41337-06, GM-43552-05, GM-42722-07, and GM-51628-02, and NIST Grant No. 1995-08-0006F. The U.S. Government may have certain rights.

FIELD OF THE INVENTION

The present invention relates to the detection of nucleic acid sequence differences in nucleic acids using a ligation phase, a capture phase, and a detection phase. The ligation phase utilizes a ligation detection reaction between one oligonucleotide probe which has a target sequence-specific portion and an addressable array-specific portion and a second oligonucleotide probe having a target sequence-specific portion and a detectable label. The capture phase involves hybridizing the ligated oligonucleotide probes to a solid support with an array of immobilized capture oligonucleotides at least some of which are complementary to the addressable array-specific portion. The labels of ligated oligonucleotide probes hybridized to the solid support are detected during the detection phase.

BACKGROUND OF THE INVENTION

Detection of Sequence Differences

Large-scale multiplex analysis of highly polymorphic loci is needed for practical identification of individuals, e.g., for paternity testing and in forensic science (Reynolds et al., Anal. Chem., 63:2–15 (1991)), for organ-transplant donor-recipient matching (Buyse et al., Tissue Antigens, 41:1–14 (1993) and Gyllensten et al., PCR Meth. Appl, 1:91–98 (1991)), for genetic disease diagnosis, prognosis, and pre-natal counseling (Chamberlain et al., Nucleic Acids Res., 16:11141–11156 (1988) and L. C. Tsui, Human Mutat., 1:197-203 (1992)), and the study of oncogenic mutations (Hollstein et al., Science, 253:49–53 (1991)). In addition, the cost-effectiveness of infectious disease diagnosis by nucleic acid analysis varies directly with the multiplex scale in panel testing. Many of these applications depend on the discrimination of single-base differences at a multiplicity of sometimes closely space loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample are fractionated by gel electrophoresis, then fixed on a nitrocellulose filter. By reacting the filter with one or more labeled probes under hybridization conditions, the presence of bands containing the probe sequence can be identified. The method is especially useful for identifying fragments in a restriction-enzyme DNA digest which contain a given probe sequence, and for analyzing restriction-fragment length polymorphisms ("RFLPs").

Another approach to detecting the presence of a given sequence or sequences in a polynucleotide sample involves selective amplification of the sequence(s) by polymerase chain reaction. U.S. Pat. No. 4,683,202 to Mullis, et al. and R. K. Saiki, et al., Science 230:1350 (1985). In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported. U.S. Pat. No. 4,883,750 to N. M. Whiteley, et al., D. Y. Wu, et al., Genomics 4:560 (1989), U. Landegren, et al., Science 241:1077 (1988), and E. Winn-Deen, et al., Clin. Chem. 37:1522 (1991). In one approach, known as oligonucleotide ligation assay ("OLA"), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of the two complementary pairs of probe elements, the target sequence is amplified geometrically, i.e., exponentially allowing very small amounts of target sequence to be detected and/or amplified. This approach is referred to as ligase chain reaction ("LCR"). F. Barany, "Genetic Disease Detection and DNA Amplification Using Cloned Thermostable Ligase," Proc. Nat'l Acad. Sci. USA, 88:189–93 (1991) and F. Barany, "The Ligase Chain Reaction (LCR) in a PCR World," PCR Methods and Applications, 1:5–16 (1991).

Another scheme for multiplex detection of nucleic acid sequence differences is disclosed in U.S. Pat. No. 5,470,705 to Grossman et. al. where sequence-specific probes, having a detectable label and a distinctive ratio of charge/translational frictional drag, can be hybridized to a target and ligated together. This technique was used in Grossman, et. al., "High-density Multiplex Detection of Nucleic Acid Sequences: Oligonucleotide Ligation Assay and Sequence-coded Separation," Nucl. Acids Res. 22(21):4527–34 (1994) for the large scale multiplex analysis of the cystic fibrosis transmembrane regulator gene.

Jou, et. al., "Deletion Detection in Dystrophin Gene by Multiplex Gap Ligase Chain Reaction and Immunochromatographic Strip Technology," Human Mutation 5:86–93 (1995) relates to the use of a so called "gap ligase chain reaction" process to amplify simultaneously selected regions of multiple exons with the amplified products being read on an immunochromatographic strip having antibodies specific to the different haptens on the probes for each exon.

There is a growing need, e.g., in the field of genetic screening, for methods useful in detecting the presence or absence of each of a large number of sequences in a target polynucleotide. For example, as many as 400 different mutations have been associated with cystic fibrosis. In screening for genetic predisposition to this disease, it is optimal to test all of the possible different gene sequence mutations in the subjects genomic DNA, in order to make a positive identification of "cystic fibrosis". It would be ideal to test for the presence or absence of all of the possible mutation sites in a single assay. However, the prior-art methods described above are not readily adaptable for use in detecting multiple selected sequences in a convenient, automated single-assay format.

Solid-phase hybridization assays require multiple liquid-handling steps, and some incubation and wash temperatures must be carefully controlled to keep the stringency needed for single-nucleotide mismatch discrimination. Multiplexing of this approach has proven difficult as optimal hybridization conditions vary greatly among probe sequences.

Allele-specific PCR products generally have the same size, and a given amplification tube is scored by the presence or absence of the product band in the gel lane associated with each reaction tube. Gibbs et al., *Nucleic Acids Res.*, 17:2437–2448 (1989). This approach requires splitting the test sample among multiple reaction tubes with different primer combinations, multiplying assay cost. PCR has also discriminated alleles by attaching different fluorescent dyes to competing allelic primers in a single reaction tube (F. F. Chehab, et al., *Proc. Natl. Acad. Sci. USA*, 86:9178–9182 (1989)), but this route to multiplex analysis is limited in scale by the relatively few dyes which can be spectrally resolved in an economical manner with existing instrumentation and dye chemistry. The incorporation of bases modified with bulky side chains can be used to differentiate allelic PCR products by their electrophoretic mobility, but this method is limited by the successful incorporation of these modified bases by polymerase, and by the ability of electrophoresis to resolve relatively large PCR products which differ in size by only one of these groups. Livak et al., *Nucleic Acids Res.*, 20:4831–4837 (1989). Each PCR product is used to look for only a single mutation, making multiplexing difficult.

Ligation of allele-specific probes generally has used solid-phase capture (U. Landegren et al., *Science*, 241:1077–1080 (1988); Nickerson et al., *Proc. Natl. Acad. Sci. USA*, 87:8923–8927 (1990)) or size-dependent separation (D. Y. Wu, et al., *Genomics*, 4:560–569 (1989) and F. Barany, *Proc. Natl. Acad. Sci.*, 88:189–193 (1991)) to resolve the allelic signals, the latter method being limited in multiplex scale by the narrow size range of ligation probes. The gap ligase chain reaction process requires an additional step—polymerase extension. The use of probes with distinctive ratios of charge/translational frictional drag technique to a more complex multiplex will either require longer electrophoresis times or the use of an alternate form of detection.

The need thus remains for a rapid single assay format to detect the presence or absence of multiple selected sequences in a polynucleotide sample.

Use of Oligonucleotide Arrays for Nucleic Acid Analysis

Ordered arrays of oligonucleotides immobilized on a solid support have been proposed for sequencing, sorting, isolating, and manipulating DNA. It has been recognized that hybridization of a cloned single-stranded DNA molecule to all possible oligonucleotide probes of a given length can theoretically identify the corresponding complementary DNA segments present in the molecule. In such an array, each oligonucleotide probe is immobilized on a solid support at a different predetermined position. All the oligonucleotide segments in a DNA molecule can be surveyed with such an array.

One example of a procedure for sequencing DNA molecules using arrays of oligonucleotides is disclosed in U.S. Pat. No. 5,202,231 to Drmanac, et. al. This involves application of target DNA to a solid support to which a plurality of oligonucleotides are attached. Sequences are read by hybridization of segments of the target DNA to the oligonucleotides and assembly of overlapping segments of hybridized oligonucleotides. The array utilizes all possible oligonucleotides of a certain length between 11 and 20 nucleotides, but there is little information about how this array is constructed. See also A. B. Chetverin, et. al., "Sequencing of Pools of Nucleic Acids on Oligonucleotide Arrays," *BioSystems* 30: 215–31 (1993); WO 92/16655 to Khrapko et. al.; Kuznetsova, et. al., "DNA Sequencing by Hybridization with Oligonucleotides Immobilized in Gel. Chemical Ligation as a Method of Expanding the Prospects for the Method," *Mol. Biol.* 28(20): 290–99(1994); M. A. Livits, et. al., "Dissociation of Duplexes Formed by Hybridization of DNA with Gel-Immobilized Oligonucleotides," *J. Biomolec. Struct. & Dynam.* 11(4): 783–812 (1994).

WO 89/10977 to Southern discloses the use of a support carrying an array of oligonucleotides capable of undergoing a hybridization reaction for use in analyzing a nucleic acid sample for known point mutations, genomic fingerprinting, linkage analysis, and sequence determination. The matrix is formed by laying nucleotide bases in a selected pattern on the support. This reference indicates that a hydroxyl linker group can be applied to the support with the oligonucleotides being assembled by a pen plotter or by masking.

WO 94/11530 to Cantor also relates to the use of an oligonucleotide array to carry out a process of sequencing by hybridization. The oligonucleotides are duplexes having overhanging ends to which target nucleic acids bind and are then ligated to the non-overhanging portion of the duplex. The array is constructed by using streptavidin-coated filter paper which captures biotinylated oligonucleotides assembled before attachment.

WO 93/17126 to Chetverin uses sectioned, binary oligonucleotide arrays to sort and survey nucleic acids. These arrays have a constant nucleotide sequence attached to an adjacent variable nucleotide sequence, both bound to a solid support by a covalent linking moiety. The constant nucleotide sequence has a priming region to permit amplification by PCR of hybridized strands. Sorting is then carried out by hybridization to the variable region. Sequencing, isolating, sorting, and manipulating fragmented nucleic acids on these binary arrays are also disclosed. In one embodiment with enhanced sensitivity, the immobilized oligonucleotide has a shorter complementary region hybridized to it, leaving part of the oligonucleotide uncovered. The array is then subjected to hybridization conditions so that a complementary nucleic acid anneals to the immobilized oligonucleotide. DNA ligase is then used to join the shorter complementary region and the complementary nucleic acid on the array. There is little disclosure of how to prepare the arrays of oligonucleotides.

WO 92/10588 to Fodor et. al., discloses a process for sequencing, fingerprinting, and mapping nucleic acids by hybridization to an array of oligonucleotides. The array of oligonucleotides is prepared by a very large scale immobilized polymer synthesis which permits the synthesis of large, different oligonucleotides. In this procedure, the substrate surface is functionalized and provided with a linker group by which oligonucleotides are assembled on the substrate. The regions where oligonucleotides are attached have protective groups (on the substrate or individual nucleotide subunits) which are selectively activated. Generally, this involves imaging the array with light using a mask of varying configuration so that areas exposed are deprotected. Areas which have been deprotected undergo a chemical reaction with a protected nucleotide to extend the oligonucleotide sequence where imaged. A binary masking strategy can be used to build two or more arrays at a given time. Detection involves positional localization of the region where hybridization has taken place. See also U.S. Pat. Nos. 5,324,633 and 5,424,186 to Fodor et. al., U.S. Pat. Nos. 5,143,854 and 5,405,783 to Pirrung, et. al., WO 90/15070 to Pirrung, et. al., A. C. Pease, et. al., "Light-generated Oligonucleotide Arrays for Rapid DNA Sequence Analysis", *Proc. Natl. Acad. Sci USA* 91: 5022–26 (1994). K. L. Beattie, et. al., "Advances in Genosensor Research," *Clin. Chem.* 41(5): 700–09 (1995) discloses attachment of previously assembled oligonucleotide probes to a solid support.

There are many drawbacks to the procedures for sequencing by hybridization to such arrays. Firstly, a very large number of oligonucleotides must be synthesized. Secondly, there is poor discrimination between correctly hybridized, properly matched duplexes and those which are mismatched. Finally, certain oligonucleotides will be difficult to hybridize to under standard conditions, with such oligonucleotides being capable of identification only through extensive hybridization studies.

The present invention is directed toward overcoming these deficiencies in the art.

SUMMARY OF THE INVENTION

The present invention relates to a method for identifying one or more of a plurality of sequences differing by one or more single base changes, insertions deletions, or translocations in a plurality of target nucleotide sequences. The method includes a ligation phase, a capture phase, and a detection phase.

The ligation phase requires providing a sample potentially containing one or more nucleotide sequences with a plurality of sequence differences. A plurality of oligonucleotide sets are utilized in this phase. Each set includes a first oligonucleotide probe, having a target-specific portion and an addressable array-specific portion, and a second oligonucleotide probe, having a target-specific portion and a detectable reporter label. The first and second oligonucleotide probes in a particular set are suitable for ligation together when hybridized adjacent to one another on a corresponding target nucleotide sequence. However, the first and second oligonucleotide probes have a mismatch which interferes with such ligation when hybridized to another nucleotide sequence present in the sample. A ligase is also utilized. The sample, the plurality of oligonucleotide probe sets, and the ligase are blended to form a mixture. The mixture is subjected to one or more ligase detection reaction cycles comprising a denaturation treatment and a hybridization treatment. The denaturation treatment involves separating any hybridized oligonucleotides from the target nucleotide sequences. The hybridization treatment involves hybridizing the oligonucleotide probe sets at adjacent positions in a base-specific manner to their respective target nucleotide sequences, if present in the sample, and ligating them to one another to form a ligated product sequence containing (a) the addressable array-specific portion, (b) the target-specific portions connected together, and (c) the detectable reporter label. The oligonucleotide probe sets may hybridize to nucleotide sequences in the sample other than their respective target nucleotide sequences but do not ligate together due to a presence of one or more mismatches and individually separate during denaturation treatment.

The next phase of the process is the capture phase. This phase involves providing a solid support with capture oligonucleotides immobilized at particular sites. The capture oligonucleotides are complementary to the addressable array-specific portions. The mixture, after being subjected to the ligation phase, is contacted with the solid support under conditions effective to hybridize the addressable array-specific portions to the capture oligonucleotides in a base-specific manner. As a result, the addressable array-specific portions are captured on the solid support at the site with the complementary capture oligonucleotides.

After the capture phase is the detection phase. During this portion of the process, the reporter labels of the ligated product sequences are captured on the solid support at particular sites. When the presence of the reporter label bound to the solid support is detected, the respective presence of one or more nucleotide sequences in the sample is indicated.

The present invention also relates to a kit for carrying out the method of the present invention which includes the ligase, the plurality of oligonucleotide sets, and the solid support with immobilized capture oligonucleotides.

Another aspect of the present invention relates to a method of forming an array of oligonucleotides on a solid support. This method involves providing a solid support having an array of positions each suitable for attachment of an oligonucleotide. A linker or surface (which can be non-hydrolyzable), suitable for coupling an oligonucleotide to the solid support at each of the array positions, is attached to the solid support. An array of oligonucleotides on a solid support is formed by a series of cycles of activating selected array positions for attachment of multimer nucleotides and attaching multimer nucleotides at the activated array positions.

Yet another aspect of the present invention relates to an array of oligonucleotides on a solid support per se. The solid support has an array of positions each suitable for attachment of an oligonucleotide. A linker or support (which can be non-hydrolyzable), suitable for coupling an oligonucleotide to the solid support, is attached to the solid support at each of the array positions. An array of oligonucleotides are placed on a solid support with at least some of the array positions being occupied by oligonucleotides having greater than sixteen nucleotides.

One aspect of the present invention involves providing the solid support with a porous surface.

Another aspect of the present invention involves carrying out the contacting of the mixture with the solid support under conditions effective to mask negative charges.

The present invention contains a number of advantages over prior art systems, particularly, its ability to carry out multiplex analyses of complex genetic systems. As a result, a large number of nucleotide sequence differences in a sample can be detected at one time. The present invention is useful for detection of, for example, cancer mutations, inherited (germline) mutations, and infectious diseases. This technology can also be utilized in conjunction with environmental monitoring, forensics, and the food industry.

In addition, the present invention provides quantitative detection of mutations in a high background of normal sequences, allows detection of closely-clustered mutations, permits detection using addressable arrays, and is amenable to automation. By combining the sensitivity of PCR with the specificity of LDR, common difficulties encountered in allele-specific PCR, such as false-positive signal generation, primer interference during multiplexing, limitations in obtaining quantitative data, and suitability for automation, have been obviated. In addition, by relying on the specificity of LDR to distinguish single-base mutations, the major inherent problem of oligonucleotide probe arrays (i.e. their inability to distinguish single-base changes at all positions in heterozygous samples) has been overcome. PCR/LDR addresses the current needs in cancer detection; to quantify mutations which may serve as clonal markers and to detect minimal residual disease and micrometastases.

In carrying out analyses of different samples, the solid support containing the array can be reused. This reduces the quantity of solid supports which need to be manufactured and lowers the cost of analyzing each sample.

The present invention also affords great flexibility in the synthesis of oligonucleotides and their attachment to solid supports. Oligonucleotides can be synthesized off of the solid support and then attached to unique surfaces on the support. This technique can be used to attach fall length oligonucleotides or peptide nucleotide analogues ("PNA") to the solid support. Alternatively, shorter nucleotide or analogue segments (dimer, trimer, tetramer, etc.) can be employed in a segment condensation or block synthesis approach to fall length oligomers on the solid support.

BRIEF DESCRIPTION OF THE DRAWINGS

FIG. 4 is a schematic diagram depicting a PCR/LDR process, according to the present invention, using addresses on the allele-specific probes which distinguishes all possible bases at a given site.

FIG. 5 is a schematic diagram depicting a PCR/LDR process, according to the present invention, using addresses on the allele-specific probes for detecting the presence of any possible base at two nearby sites.

FIG. 6 is a schematic diagram of a PCR/LDR process, according to the present invention, using addresses on the allele-specific probes distinguishing insertions and deletions.

FIG. 7 is a schematic diagram of a PCR/LDR process, in accordance with the present invention, using addresses on the allele-specific probes to detect a low abundance mutation (within a codon) in the presence of an excess of normal sequence.

FIG. 8 is a schematic diagram of a PCR/LDR process, in accordance with the present invention, where the address is placed on the common probe and the allele differences are distinguished by different fluorescent signals F1, F2, F3, and F4.

FIG. 9 is a schematic diagram of a PCR/LDR process, in accordance with the present invention, where both adjacent and nearby alleles are detected.

FIG. 10 is a schematic diagram of a PCR/LDR process, in accordance with the present invention, where all possible single-base mutations for a single codon are detected.

FIG. 11 shows the chemical reactions for covalent modifications, grafting, and oligomer attachments to solid supports.

In FIG. 13B, the addressable array-specific portions are on the allele-specific probe. Alleles are distinguished by capture of fluorescent signals on addresses Z1 and Z2, respectively. In FIG. 13C, the addressable array-specific portions are on the common probe and alleles are distinguished by capture of fluorescent signals F1 and F2, which correspond to the two alleles, respectively.

FIGS. 15A–E are perspective views of the 8×8 array construction protocol of FIGS. 14A–E.

FIGS. 16A–C are views of an apparatus used to spot full-length, individual 24 mer oligomers on a solid support in accordance with FIGS. 14A–E to 15A–E.

FIG. 17 shows a design in accordance with the present invention using 36 tetramers differing by at least 2 bases, which can be used to create a series of unique 24-mers.

FIGS. 18A–G are schematic diagrams showing addition of PNA tetramers to generate a 5×5 array of unique 25 mer addresses.

FIGS. 20A–C are perspective views of the 8×8 array construction protocol of FIGS. 19B–C.

FIGS. 22A–C are schematic views of an apparatus used to synthesize the 8×8 array of 24 mers on a solid support in accordance with FIGS. 19B–C, 20A–C, and 21A–G.

FIGS. 23A–C are perspective views of the 8×8 array construction protocol of FIG. 19 (FIGS. 19D–19E).

FIGS. 24A–C are schematic views of an apparatus used to synthesize the 5×5 array of 24 mers on a solid support, in accordance with FIGS. 19D–E and 23A–C.

FIGS. 25A–C are schematic diagrams of a valve block assembly capable of routing six input solutions to 5 output ports.

FIGS. 26A–D are diagrams of a circular manifold capable of simultaneously channeling 6 input solutions into 5 output ports.

FIG. 28 shows phosphorimager data for different derivatized surfaces.

FIG. 29 shows phosphorimager data for different crosslinking conditions of the polymer matrix.

FIG. 35A shows a schematic representation of LDR probes used to distinguish mutations. Each allele specific probe contains an addressable sequence complement (Z1 or Z3) on the 5'-end and the discriminating base on the 3'-end. The common LDR probe is phosphorylated on the 5'-end and contains a fluorescent label on the 3'-end. The probes hybridize adjacent to each other on target DNA, and the nick will be sealed by the ligase if and only if there is perfect complementarity at the junction. FIG. 35B shows the presence and type of mutation is determined by hybridizing the contents of an LDR reaction to an addressable DNA array. The sequences of the probes' addressable array-specific portions are designed to be sufficiently different, so that only probes containing the correct complement to a given portion will remain bound at that address. FIG. 35C is a schematic representation of chromosomal DNA containing the K-ras gene. Exons are shaded and the position of codons 12 and 13 are shown. Exon-specific probes were used to selectively amplify K-ras DNA flanking codons 12 and 13. Probes were designed for LDR detection of seven possible mutations in these two codons as described in FIG. 35A above.

FIG. 40 shows the ligation of probes to detect 3 specific mutations in BRCA 1 and BRCA 2 genes.

FIG. 41 shows the ligation of probes to detect 3 specific mutations in BRCA 1 and BRCA 2 genes.

DETAILED DESCRIPTION OF THE INVENTION AND DRAWINGS

Figure 1:
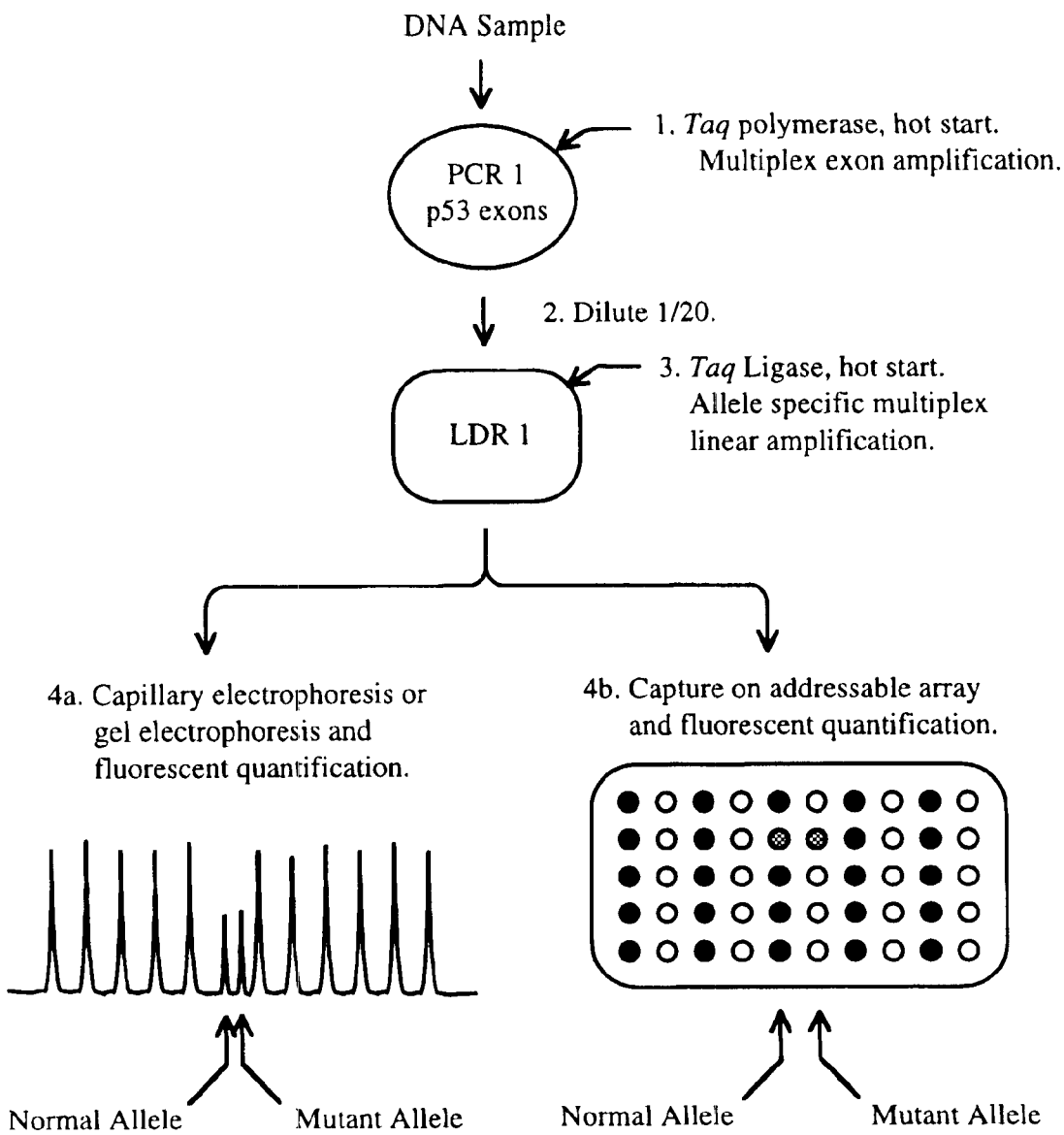
FIG. 1 is a flow diagram depicting polymerase chain reaction ("PCR")/ligase detection reaction ("LDR") processes, according to the prior art and the present invention, for detection of germline mutations, such as point mutations.

The present invention relates to a method for identifying one or more of a plurality of sequences differing by one or more single-base changes, insertions, deletions, or translocations in a plurality of target nucleotide sequences. The method includes a ligation phase, a capture phase, and a detection phase.

The ligation phase requires providing a sample potentially containing one or more nucleotide sequences with a plurality of sequence differences. A plurality of oligonucleotide sets are utilized in this phase. Each set includes a first oligonucleotide probe, having a target-specific portion and an addressable array-specific portion, and a second oligonucleotide probe, having a target-specific portion and a detectable reporter label. The first and second oligonucleotide probes in a particular set are suitable for ligation together when hybridized adjacent to one another on a corresponding target nucleotide sequence. However, the first and second oligonucleotide probes have a mismatch which interferes with such ligation when hybridized to another nucleotide sequence present in the sample. A ligase is also utilized. The sample, the plurality of oligonucleotide probe sets, and the ligase are blended to form a mixture. The mixture is subjected to one or more ligase detection reaction cycles comprising a denaturation treatment and a hybridization treatment. The denaturation treatment involves separating any hybridized oligonucleotides from the target nucleotide sequences. The hybridization treatment involves hybridizing, the oligonucleotide probe sets at adjacent positions in a base-specific manner to their respective target nucleotide sequences, if present in the sample, and ligating them to one another to form a ligated product sequence containing (a) the addressable array-specific portion, (b) the target-specific portions connected together, and (c) the detectable reporter label. The oligonucleotide probe sets may hybridize to nucleotide sequences in the sample other than their respective target nucleotide sequences but do not ligate together due to a presence of one or more mismatches and individually separate during denaturation treatment.

The next phase of the process is the capture phase. This phase involves providing a solid support with capture oligonucleotides immobilized at particular sites. The capture oligonucleotides are complementary to the addressable array-specific portions. The mixture, after being subjected-to the ligation phase, is contacted with the solid support under conditions effective to hybridize the addressable array-specific portions to the capture oligonucleotides in a base-specific manner. As a result, the addressable array-specific portions are captured on the solid support at the site with the complementary capture oligonucleotides.

One aspect of the present invention involves providing the solid support with a porous surface.

Another aspect of the present invention involves carrying out the contacting of the mixture with the solid support under conditions effective to mask negative charges.

After the capture phase is the detection phase. During this portion of the process, the reporter labels of the ligated product sequences are captured on the solid support at particular sites. When the presence of the reporter label bound to the solid support is detected, the respective presence of one or more nucleotide sequences in the sample is indicated.

Often, a number of different single-base mutations, insertions, or deletions may occur at the same nucleotide position of the sequence of interest. The method provides for having an oligonucleotide set, where the second oligonucleotide probe is common and contains the detectable label, and the first oligonucleotide probe has different addressable array-specific portions and target-specific portions. The first oligonucleotide probe is suitable for ligation to a second adjacent oligonucleotide probe at a first ligation junction, when hybridized without mismatch, to the sequence in question. Different first adjacent oligonucleotide probes would contain different discriminating base(s) at the junction where only a hybridization without mismatch at the junction would allow for ligation. Each first adjacent oligonucleotide would contain a different addressable array-specific portion, and, thus, specific base changes would be distinguished by capture at different addresses. In this scheme, a plurality of different capture oligonucleotides are attached at different locations on the solid support for multiplex detection of additional nucleic acid sequences differing from other nucleic acids by at least a single base. Alternatively, the first oligonucleotide probe contains common addressable array-specific portions, and the second oligonucleotide probes have different detectable labels and target-specific portions.

Such arrangements permit multiplex detection of additional nucleic acid sequences differing from other nucleic acids by at least a single base. The nucleic acids sequences can be on the same or different alleles when carrying out such multiplex detection.

The present invention also relates to a kit for carrying out the method of the present invention which includes the ligase, the plurality of different oligonucleotide probe sets, and the solid support with immobilized capture oligonucleotides. Primers for preliminary amplification of the target nucleotide sequences may also be included in the kit. If amplification is by polymerase chain reaction, polymerase may also be included in the kit.

Figure 2:
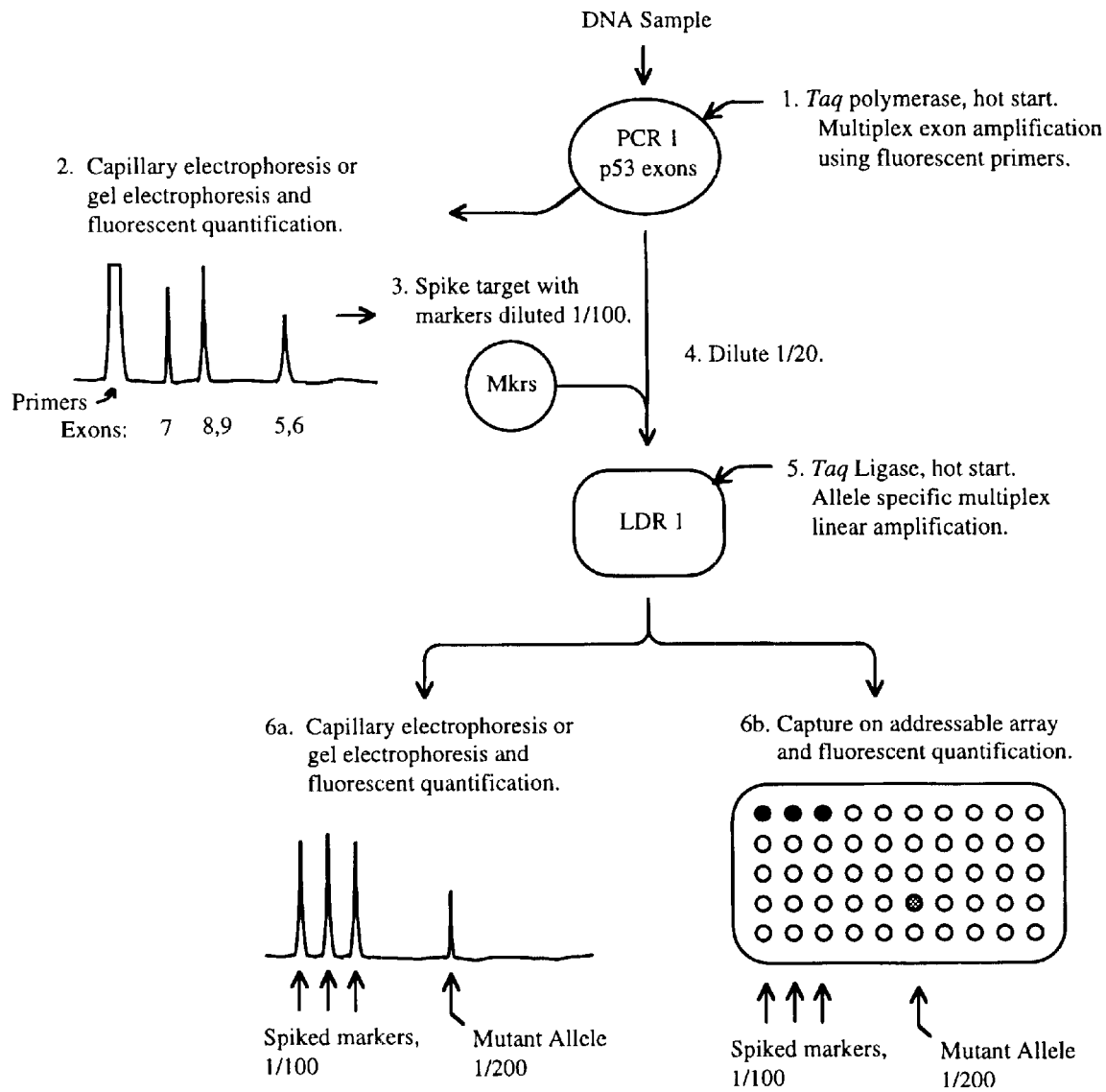
FIG. 2 is a flow diagram depicting PCR/LDR processes, according to the prior art and the present invention, for detection of cancer-associated mutations.

FIGS. 1 and 2 show flow diagrams of the process of the present invention compared to a prior art ligase detection reaction utilizing capillary or gel electrophoresis/fluorescent quantification. FIG. 1 relates to detection of a germline mutation detection, while FIG. 2 shows the detection of cancer.

FIG. 1 depicts the detection of a germline point mutation, such as the p53 mutations responsible for Li-Fraumeni syndrome. In step 1, after DNA sample preparation, exons 5–8 are PCR amplified using Taq (i.e. *Thermus aquaticus*) polymerase under hot start conditions. At the end of the reaction, Taq polymerase is degraded by heating at 100° C. for 10 min. Products are diluted 20-fold in step 2 into fresh LDR buffer containing allele-specific and common LDR probes. A tube generally contains about 100 to 200 fmoles of each primer. In step 3, the ligase detection reaction is initiated by addition of Taq ligase under hot start conditions. The LDR probes ligate to their adjacent probes only in the presence of target sequence which gives perfect complementarity at the junction site. The products may be detected in two different formats. In the first format 4a., used in the prior art, fluorescently-labeled LDR probes contain different length poly A or hexaethylene oxide tails. Thus, each LDR product, resulting from ligation to normal DNA with a slightly different mobility, yields a ladder of peaks. A germline mutation would generate a new peak on the electrophorogram. The size of the new peak will approximate the amount of the mutation present in the original sample; 0% for homozygous normal, 50% for heterozygous carrier, or 100% for homozygous mutant. In the second format 4b., in accordance with the present invention, each allele-specific probe contains e.g., 24 additional nucleotide bases on their 5' ends. These sequences are unique addressable sequences which will specifically hybridize to their complementary address sequences on an addressable array. In the LDR reaction, each allele-specific probe can ligate to its adjacent fluorescently labeled common probe in the presence of the corresponding target sequence. Wild type and mutant alleles are captured on adjacent addresses on the array. Unreacted probes are washed away. The black dots indicate 100% signal for the wild type allele. The white dots indicate 0% signal for the mutant alleles. The shaded dots indicate the one position of germline mutation, 50% signal for each allele.

FIG. 2 depicts detection of somatic cell mutations in the p53 tumor suppressor gene but is general for all low sensitivity mutation detection. In step 1, DNA samples are prepared and exons 5–9 are PCR amplified as three fragments using fluorescent PCR primers. This allows for fluorescent quantification of PCR products in step 2 using capillary or gel electrophoresis. In step 3, the products are spiked with a 1/100 dilution of marker DNA (for each of the three fragments). This DNA is homologous to wild type DNA, except it contains a mutation which is not observed in cancer cells, but which may be readily detected with the appropriate LDR probes. The mixed DNA products in step 4 are diluted 20-fold into buffer containing all the LDR probes which are specific only to mutant or marker alleles. In step 5, the ligase reaction is initiated by addition of Taq ligase under hot start conditions. The LDR probes ligate to their adjacent probes only in the presence of target sequences which give perfect complementarity at the junction site. The products may be detected in the same two formats described in FIG. 1. In the format of step 6a, which is used in the prior art, products are separated by capillary or gel electrophoresis, and fluorescent signals are quantified. Ratios of mutant peaks to marker peaks give approximate amount of cancer mutations present in the original sample divided by 100. In the format of step 6b, in accordance with the present invention, products are detected by specific hybridization to complementary sequences on an addressable array. Ratios of fluorescent signals in mutant dots to marker dots give the approximate amount of cancer mutations present in the original sample divided by 100.

The ligase detection reaction process, in accordance with the present invention, is best understood by referring to FIGS. 3–10. It is described generally in WO 90/17239 to Barany et al., F. Barany et al., "Cloning, Overexpression and Nucleotide Sequence of a Thermostable DNA Ligase-encoding Gene," *Gene,* 109:1–11 (1991), and F. Barany, "Genetic Disease Detection and DNA Amplification Using Cloned Thermostable Ligase," *Proc. Natl. Acad. Sci. USA,* 88:189–193 (1991), the disclosures of which are hereby incorporated by reference. In accordance with the present invention, the ligase detection reaction can use 2 sets of complementary oligonucleotides. This is known as the ligase chain reaction which is described in the 3 immediately preceding references, which are hereby incorporated by reference. Alternatively, the ligase detection reaction can involve a single cycle which is known as the oligonucleotide ligation assay. See Landegren, et al., "A Ligase-Mediated Gene Detection Technique," *Science* 241:1077–80 (1988); Landegren, et al., "DNA Diagnostics—Molecular Techniques and Automation," *Science* 242:229–37 (1988); and U.S. Pat. No. 4,988,617 to Landegren, et al.

During the ligase detection reaction phase of the process, the denaturation treatment is carried out at a temperature of 80–105° C., while hybridization takes place at 50–85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase of the process is 1 to 250 minutes.

The oligonucleotide probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

In one variation, the oligonucleotides of the oligonucleotide probe sets each have a hybridization or melting temperature (i.e. $T_m$) of 66–70° C. These oligonucleotides are 20–28 nucleotides long.

It may be desirable to destroy chemically or enzymatically unconverted LDR oligonucleotide probes that contain addressable nucleotide array-specific portions prior to capture of the ligation products on a DNA array. Such unconverted probes will otherwise compete with ligation products for binding at the addresses on the array of the solid support which contain complementary sequences. Destruction can be accomplished by utilizing an exonuclease, such as exonuclease III (L-H Guo and R. Wu, *Methods in Enzymology* 100:60–96 (1985), which is hereby incorporated by reference) in combination with LDR probes that are blocked at the ends and not involved with ligation of probes to one another. The blocking moiety could be a reporter group or a phosphorothioate group. T. T. Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p.285–291 (1994), which is hereby incorporated by reference. After the LDR process, unligated probes are selectively destroyed by incubation of the reaction mixture with the exonuclease. The ligated probes are protected due to the elimination of free 3' ends which are required for initiation of the exonuclease reaction. This approach results in an increase in the signal-to-noise ratio, especially where the LDR reaction forms only a small amount of product. Since unligated oligonucleotides compete for capture by the capture oligonucleotide, such competition with the ligated oligonucleotides lowers the signal. An additional advantage of this approach is that unhybridized label-containing sequences are degraded and, therefore, are less able to cause a target-independent background signal, because they can be removed more easily from the DNA array by washing.

The oligonucleotide probe sets, as noted above, have a reporter label suitable for detection. Useful labels include chromophores, fluorescent moieties, enzymes, antigens, heavy metals, magnetic probes, dyes, phosphorescent groups, radioactive materials, chemiluminescent moieties, and electrochemical detecting moieties. The capture oligonucleotides can be in the form of ribonucleotides, deoxyribonucleotides, modified ribonucleotides, modified deoxyribonucleotides, peptide nucleotide analogues, modified peptide nucleotide analogues, modified phosphate-sugar backbone oligonucleotides, nucleotide analogues, and mixtures thereof. Where the process of the present invention involves use of a plurality of oligonucleotide sets, the second oligonucleotide probes can be the same, while the addressable array-specific portions of the first oligonucleotide probes differ. Alternatively, the addressable array-specific portions of the first oligonucleotide probes may be the same, while the reporter labels of the second oligonucleotide probes are different.

Prior to the ligation detection reaction phase of the present invention, the sample is preferably amplified by an initial target nucleic acid amplification procedure. This increases the quantity of the target nucleotide sequence in the sample. For example, the initial target nucleic acid amplification may be accomplished using the polymerase chain reaction process, self-sustained sequence replication, or Q-β replicase-mediated RNA amplification. The polymerase chain reaction process is the preferred amplification procedure and is fully described in H. Erlich, et. al., "Recent Advances in the Polymerase Chain Reaction," *Science* 252: 1643–50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487–91 (1988), which are hereby incorporated by reference. J. Guatelli, et. al., "Isothermal, in vitro Amplification of Nucleic Acids by a Multienzyme Reaction Modeled After Retroviral Replication," *Proc. Natl. Acad. Sci. USA* 87: 1874–78 (1990), which is hereby incorporated by reference, describes the self-sustained sequence replication process. The Q-β replicase-mediated RNA amplification is disclosed in F. Kramer, et. al., "Replicatable RNA Reporters," *Nature* 339: 401–02 (1989), which is hereby incorporated by reference.

Figure 3:
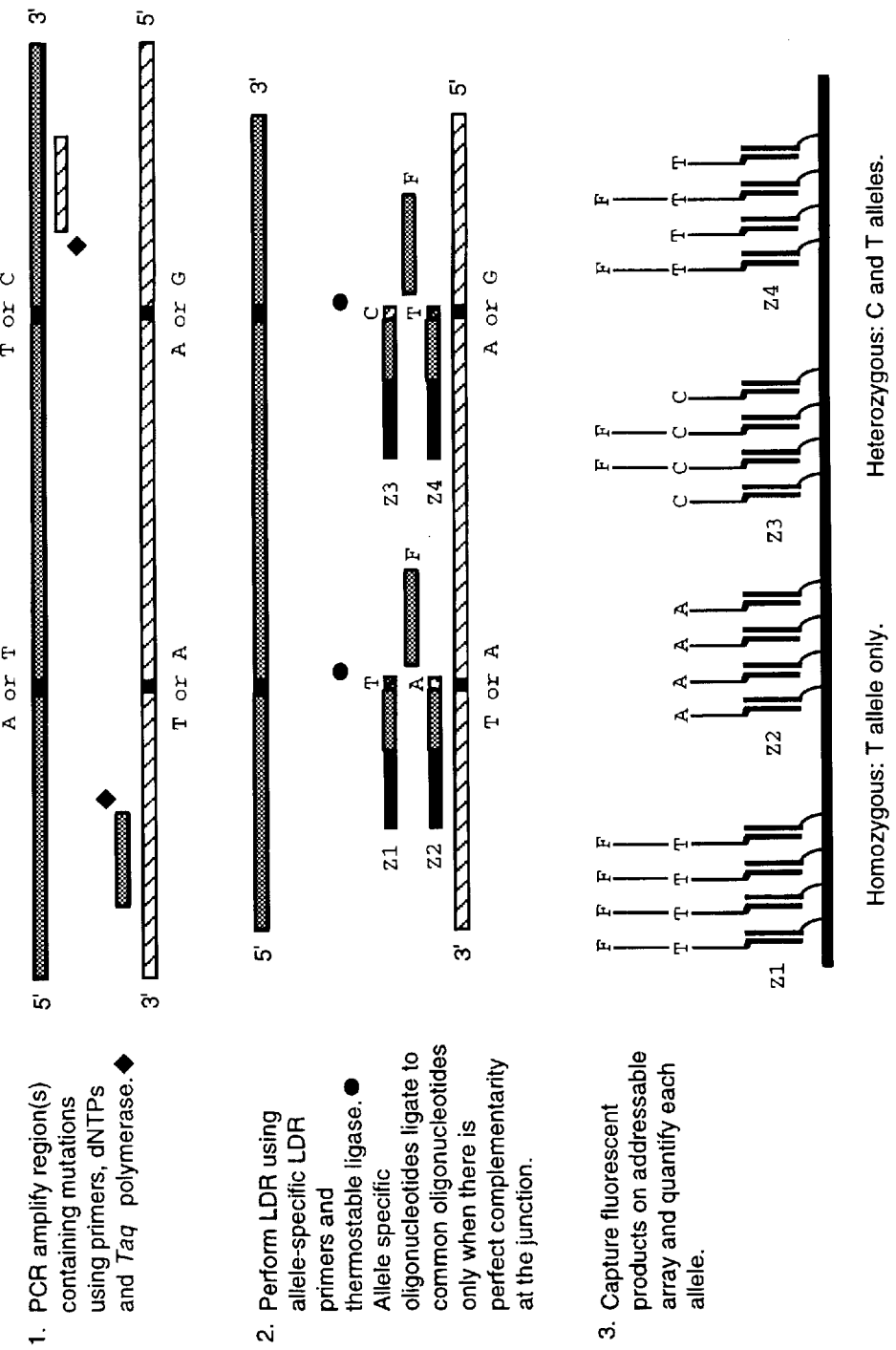
FIG. 3 is a schematic diagram depicting a PCR/LDR process, according to the present invention, using addresses on the allele-specific probes for detecting homo- or heterozygosity at two polymorphisms (i.e. allele differences) on the same gene.

The use of the polymerase chain reaction process and then the ligase detection process, in accordance with the present invention, is shown in FIG. 3. Here, homo- or heterozygosity at two polymorphisms (i.e. allele differences) are on the same gene. Such allele differences can alternatively be on different genes.

As shown in FIG. 3, the target nucleic acid, when present in the form of a double stranded DNA molecule is denatured to separate the strands. This is achieved by heating to a temperature of 80–105° C. Polymerase chain reaction primers are then added and allowed to hybridize to the strands, typically at a temperature of 20–85° C. A thermostable polymerase (e.g., *Thermus aquaticus* polymerase) is also added, and the temperature is then adjusted to 50–85° C. to extend the primer along the length of the nucleic acid to which the primer is hybridized. After the extension phase of the polymerase chain reaction, the resulting double stranded molecule is heated to a temperature of 80–105° C. to denature the molecule and to separate the strands. These hybridization, extension, and denaturation steps may be repeated a number of times to amplify the target to an appropriate level.

Once the polymerase chain reaction phase of the process is completed, the ligation detection reaction phase begins, as shown in FIG. 3. After denaturation of the target nucleic acid, if present as a double stranded DNA molecule, at a temperature of 80–105° C., preferably 94° C., ligation detection reaction oligonucleotide probes for one strand of the target nucleotide sequence are added along with a ligase (for example, as shown in FIG. 3, a thermostable ligase like

*Thermus aquaticus* ligase). The oligonucleotide probes are then allowed to hybridize to the target nucleic acid molecule and ligate together, typically, at a temperature of 45–85° C., preferably, 65° C. When there is perfect complementarity at the ligation junction, the oligonucleotides can be ligated together. Where the variable nucleotide is T or A, the presence of T in the target nucleotide sequence will cause the oligonucleotide probe with the addressable array-specific portion Z1 to ligate to the oligonucleotide probe with the reporter label F, and the presence of A in the target nucleotide sequence will cause the oligonucleotide probe with the addressable array-specific portion Z2 to ligate to the oligonucleotide probe with reporter label F. Similarly, where the variable nucleotide is A or G, the presence of T in the target nucleotide sequence will cause the oligonucleotide probe with addressable array-specific portion Z4 to ligate to the oligonucleotide probe with the reporter label F, and the presence of C in the target nucleotide sequence will cause the oligonucleotide probe with the addressable array-specific portion Z3 to ligate to the oligonucleotide probe with reporter label F. Following ligation, the material is again subjected to denaturation to separate the hybridized strands. The hybridization/ligation and denaturation steps can be carried through one or more cycles (e.g., 1 to 50 cycles) to amplify the target signal. Fluorescent ligation products (as well as unligated oligonucleotide probes having an addressable array-specific portion) are captured by hybridization to capture probes complementary to portions Z1, Z2, Z3, and Z4 at particular addresses on the addressable arrays. The presence of ligated oligonucleotides is then detected by virtue of the label F originally on one of the oligonucleotides. In FIG. 3, ligated product sequences hybridize to the array at addresses with capture oligonucleotides complementary to addressable array-specific portions Z1 and Z3, while unligated oligonucleotide probes with addressable array-specific portions Z2 and Z4 hybridize to their complementary capture oligonucleotides. However, since only the ligated product sequences have label F, only their presence is detected.

FIG. 4 is a flow diagram of a PCR/LDR process, in accordance with the present invention, which distinguishes any possible base at a given site. Appearance of fluorescent signal at the addresses complementary to addressable array-specific portions Z1, Z2, Z3, and Z4 indicates the presence of A, G, C, and T alleles in the target nucleotide sequence, respectively. Here, the presence of the A and C alleles in the target nucleotide sequences is indicated due to the fluorescence at the addresses on the solid support with capture oligonucleotide probes complementary to portions Z1 and Z3, respectively. Note that in FIG. 4 the addressable array-specific portions are on the discriminating oligonucleotide probes, and the discriminating base is on the 3' end of these probes.

FIG. 5 is a flow diagram of a PCR/LDR process, in accordance with the present invention, for detecting the presence of any possible base at two nearby sites. Here, the LDR primers are able to overlap, yet are still capable of ligating provided there is perfect complementarity at the junction. This distinguishes LDR from other approaches, such as allele-specific PCR where overlapping primers would interfere with one another. In FIG. 5, the first nucleotide position is heterozygous at the A and C alleles, while the second nucleotide position is heterozygous to the G, C, and T alleles. As in FIG. 4, the addressable array-specific portions are on the discriminating oligonucleotide probes, and the discriminating base is on the 3' end of these probes. The reporter group (e.g., the fluorescent label) is on the 3' end of the common oligonucleotide probes. This is possible for example with the 21 hydroxylase gene, where each individual has 2 normal and 2 pseudogenes, and, at the intron 2 splice site (nucleotide 656), there are 3 possible single bases (G, A, and C). Also, this can be used to detect low abundance mutations in HIV infections which might indicate emergence of drug resistant (e.g., to AZT) strains. Returning to FIG. 5, appearance of fluorescent signal at the addresses complementary to addressable array-specific portions Z1, Z2, Z3, Z4, Z5, Z6, Z7, and Z8 indicates the presence of the A, G, C, and T, respectively, in the site heterozygous at the A and C alleles, and A, G, C, and T, respectively, in the site heterozygous at the G, C, and T alleles.

FIG. 6 is a flow diagram of a PCR/LDR process, in accordance with the present invention, where insertions (top left set of probes) and deletions (bottom right set of probes) are distinguished. On the left, the normal sequence contains 5 A's in a polyA tract. The mutant sequence has an additional 2As inserted into the tract. Therefore, the LDR products with addressable array-specific portions Z1 (representing the normal sequence) and Z3 (representing a 2 base pair insertion) would be fluorescently labeled by ligation to the common primer. While the LDR process (e.g., using a thermostable ligase enzyme) has no difficulty distinguishing single base insertions or deletions in mononucleotide repeats, allele-specific PCR is unable to distinguish such differences, because the 3' base remains the same for both alleles. On the right, the normal sequence is a (CA)5 repeat (i.e. CACACACACA). The mutant contains two less CA bases than the normal sequence (i.e. CACACA). These would be detected as fluorescent LDR products at the addressable array-specific portions Z8 (representing the normal sequence) and Z6 (representing the 2 CA deletion) addresses. The resistance of various infectious agents to drugs can also be determined using the present invention. In FIG. 6, the presence of ligated product sequences, as indicated by fluorescent label F, at the address having capture oligonucleotides complementary to Z1 and Z3 demonstrates the presence of both the normal and mutant poly A sequences. Similarly, the presence of ligated product sequences, as indicated by fluorescent label F, at the address having capture oligonucleotides complementary to Z6 and Z8 demonstrates the presence of both the normal CA repeat and a sequence with one repeat unit deleted.

FIG. 7 is a flow diagram of a PCR/LDR process, in accordance with the present invention, using addressable array-specific portions to detect a low abundance mutation in the presence of an excess of normal sequence. FIG. 7 shows codon 12 of the K-ras gene, sequence G<u>G</u>T, which codes for glycine ("Gly"). A small percentage of the cells contain the G to A mutation in G<u>A</u>T, which codes for aspartic acid ("Asp"). The LDR probes for wild-type (i.e. normal sequences) are missing from the reaction. If the normal LDR probes (with the discriminating base=G) were included, they would ligate to the common probes and overwhelm any signal coming from the mutant target. Instead, as shown in FIG. 7, the existence of a ligated product sequence with fluorescent label F at the address with a capture oligonucleotide complementary to addressable array-specific portion Z4 indicates the presence of the aspartic acid encoding mutant.

FIG. 8 is a flow diagram of a PCR/LDR process, in accordance with the present invention, where the addressable array-specific portion is placed on the common oligonucleotide probe, while the discriminating oligonucleotide probe has the reporter label. Allele differences are distinguished by different fluorescent signals, F1, F2, F3, and F4. This mode allows for a more dense use of the arrays, because each position is predicted to light up with some group. It has the disadvantage of requiring fluorescent groups which have minimal overlap in their emission spectra and will require multiple scans. It is not ideally suitable for detection of low abundance alleles (e.g., cancer associated mutations).

FIG. 9 is a flow diagram of a PCR/LDR process, in accordance with the present invention, where both adjacent and nearby alleles are detected. The adjacent mutations are right next to each other, and one set of oligonucleotide probes discriminates the bases on the 3' end of the junction (by use of different addressable array-specific portions Z1, Z2, Z3, and Z4), while the other set of oligonucleotide probes discriminates the bases on the 5' end of the junction (by use of different fluorescent reporter labels F1, F2, F3, and F4). In FIG. 9, codons in a disease gene (e.g. CFTR for cystic fibrosis) encoding Gly and arginine ("Arg"), respectively, are candidates for germline mutations. The detection results in FIG. 9 show the Gly (GGA; indicated by the ligated product sequence having portion Z2 and label F2) has been mutated to glutamic acid ("Glu") (GAA; indicated by the ligated product sequence having portion Z2 and label F1), and the Arg (CGG; indicated by the ligated product sequence having portion Z7 and label F2) has been mutated to tryptophan ("Trp") (TGG; indicated by the ligated product sequence with portion Z8 and label F2). Therefore, the patient is a compound heterozygous individual (i.e. with allele mutations in both genes) and will have the disease.

FIG. 10 is a flow diagram of a PCR/LDR process, in accordance with the present invention, where all possible single-base mutations for a single codon are detected. Most amino acid codons have a degeneracy in the third base, thus the first two positions can determine all the possible mutations at the protein level. These amino acids include arginine, leucine, serine, threonine, proline, alanine, glycine, and valine. However, some amino acids are determined by all three bases in the codon and, thus, require the oligonucleotide probes to distinguish mutations in 3 adjacent positions. By designing four oligonucleotide probes containing the four possible bases in the penultimate position to the 3' end, as well as designing an additional four capture oligonucleotides containing the four possible bases at the 3' end, as shown in FIG. 10, this problem has been solved. The common oligonucleotide probes with the reporter labels only have two fluorescent groups which correspond to the codon degeneracies and distinguish between different ligated product sequences which are captured at the same array address. For example, as shown in FIG. 10, the presence of a glutamine ("Gln") encoding codon (i.e., CAA and CAG) is indicated by the presence of a ligated product sequence containing portion Z1 and label F2. Likewise, the existence of a Gln to histidine ("His") encoding mutation (coded by the codon CAC) is indicated by the presence of ligated product sequences with portion Z1 and label F2 and with portion Z7 and label F2 There is an internal redundancy built into this assay due to the fact that primers Z1 and Z7 have the identical sequence.

A particularly important aspect of the present invention is its capability to quantify the amount of target nucleotide sequence in a sample. This can be achieved in a number of ways by establishing standards which can be internal (i.e. where the standard establishing material is amplified and detected with the sample) or external (i.e. where the standard establishing material is not amplified, and is detected with the sample).

In accordance with one quantification method, the signal generated by the reporter label, resulting from capture of ligated product sequences produced from the sample being analyzed, are detected. The strength of this signal is compared to a calibration curve produced from signals generated by capture of ligated product sequences in samples with known amounts of target nucleotide sequence. As a result, the amount of target nucleotide sequence in the sample being analyzed can be determined. This technique involves use of an external standard.

Another quantification method, in accordance with the present invention, relates to an internal standard. Here, a known amount of one or more marker target nucleotide sequences are added to the sample. In addition, a plurality of marker-specific oligonucleotide probe sets are added along with the ligase, the previously-discussed oligonucleotide probe sets, and the sample to a mixture. The marker-specific oligonucleotide probe sets have (1) a first oligonucleotide probe with a target-specific portion complementary to the marker target nucleotide sequence and an addressable array-specific portion complementary to capture oligonucleotides on the support and (2) a second oligonucleotide probe with a target-specific portion complementary to the marker target nucleotide sequence and a detectable reporter label. The oligonucleotide probes in a particular marker-specific oligonucleotide set are suitable for ligation together when hybridized adjacent to one another on a corresponding marker target nucleotide sequence. However, there is a mismatch which interferes with such ligation when hybridized to any other nucleotide sequence present in the sample or added marker sequences. The presence of ligated product sequences captured on the solid support is identified by detection of reporter labels. The amount of target nucleotide sequences in the sample is then determined by comparing the amount of captured ligated product generated from known amounts of marker target nucleotide sequences with the amount of other ligated product sequences captured.

Another quantification method in accordance with the present invention involves analysis of a sample containing two or more of a plurality of target nucleotide sequences with a plurality of sequence differences. Here, ligated product sequences corresponding to the target nucleotide sequences are detected and distinguished by any of the previously-discussed techniques. The relative amounts of the target nucleotide sequences in the sample are then quantified by comparing the relative amounts of captured ligated product sequences generated. This provides a quantitative measure of the relative level of the target nucleotide sequences in the sample.

The ligase detection reaction process phase of the present invention can be preceded by the ligase chain reaction process to achieve oligonucleotide product amplification. This process is fully described in F. Barany, et. al., "Cloning, Overexpression and Nucleotide Sequence of a Thermostable DNA Ligase-encoding Gene," *Gene* 109: 1–11 (1991) and F. Barany, "Genetic Disease Detection and DNA Amplification Using Cloned Thermostable Ligase," *Proc. Natl. Acad. Sci. USA* 88: 189–93 (1991), which are hereby incorporated by reference. Instead of using the ligase chain reaction to achieve amplification, a transcription-based amplifying procedure can be used.

The preferred thermostable ligase is that derived from *Thermus aquaticus*. This enzyme can be isolated from that organism. M. Takahashi, et al., "Thermophillic DNA Ligase," *J. Biol. Chem.* 259:10041–47 (1984), which is hereby incorporated by reference. Alternatively, it can be prepared recombinantly. Procedures for such isolation as well as the recombinant production of *Thermus aquaticus* ligase as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," *Gene* 109: 1–11 (1991), which are hereby incorporated by reference. These references contain complete sequence information for this ligase as well as the encoding DNA. Other suitable ligases include *E. coli* ligase, T4 ligase, Thermus sp. AK16 ligase, *Aquifex aeolicus* ligase, *Thermotoga maritima* ligase, and Pyrococcus ligase.

The ligation amplification mixture may include a carrier DNA, such as salmon sperm DNA.

The hybridization step, which is preferably a thermal hybridization treatment, discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli*, Salmonella, Shigella, Klebsiella, Pseudomonas, *Listeria monocytogenes*, *Mycobacterium tuberculosis*, *Mycobacterium avium-intracellulare*, Yersinia, Francisella, Pasteurella, Brucella, Clostridia, *Bordetella pertussis*, Bacteroides, *Staphylococcus aureus*, *Streptococcus pneumonia*, B-Hemolytic strep., Corynebacteria, Legionella, Mycoplasma, Ureaplasma, Chlamydia, *Neisseria gonorrhea*, *Neisseria meningitides*, *Hemophilus influenza*, *Enterococcus faecalis*, *Proteus vulgaris*, *Proteus mirabilis*, *Helicobacter pylori*, *Treponema palladium*, *Borrelia burgdorferi*, *Borrelia recurrentis*, Rickettsial pathogens, Nocardia, and Acitnomycetes.

Fungal infectious agents which can be detected by the present invention include *Cryptococcus neoformans*, *Blastomyces dermatitidis*, *Histoplasma capsulatum*, *Coccidioides immitis*, *Paracoccicioides brasiliensis*, *Candida albicans*, *Aspergillus fumigautus*, Phycomycetes (Rhizopus), *Sporothrix schenckii*, *Chromomycosis*, and *Maduromycosis*.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodiumfalciparum*, *Plasmodium malaria*, *Plasmodium vivax*, *Plasmodium ovale*, *Onchoverva volvulus*, Leishmania, Trypanosoma spp., Schistosoma spp., *Entamoeba histolytica*, Cryptosporidum, Giardia spp., Trichimonas spp., *Balatidium coli*, *Wuchereria bancrofti*, Toxoplasma spp., *Enterobius vermicularis*, *Ascaris lumbricoides*, *Trichuris trichiura*, *Dracunculus medinesis*, trematodes, *Diphyllobothrium latum*, Taenia spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal screening for chromosomal and genetic aberrations or post natal screening for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Syndrome, thalassemia, Klinefelter's Syndrome, Huntington's Disease, autoimmune diseases, lipidosis, obesity defects, hemophilia, inborn errors in metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, *Familial polyposis coli*, Her2/Neu amplification, Bcr/Ab1, K-ras gene, human papillomavirus Types 16 and 18, leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, ENT tumors, and loss of heterozygosity.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety or forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Desirably, the oligonucleotide probes are suitable for ligation together at a ligation junction when hybridized adjacent to one another on a corresponding target nucleotide sequence due to perfect complementarity at the ligation junction. However, when the oligonucleotide probes in the set are hybridized to any other nucleotide sequence present in the sample, there is a mismatch at a base at the ligation junction which interferes with ligation. Most preferably, the mismatch is at the base adjacent the 3' base at the ligation junction. Alternatively, the mismatch can be at the bases adjacent to bases at the ligation junction.

The process of the present invention is able to detect the first and second nucleotide sequences in the sample in an amount of 100 attomoles to 250 femtomoles. By coupling the LDR step with a primary polymerase-directed amplification step, the entire process of the present invention is able to detect target nucleotide sequences in a sample containing as few as a single molecule. Furthermore, PCR amplified products, which often are in the picomole amounts, may easily be diluted within the above range. The ligase detection reaction achieves a rate of formation of mismatched ligated product sequences which is less than 0.005 of the rate of formation of matched ligated product sequences.

Once the ligation phase of the process is completed, the capture phase is initiated. During the capture phase of the process, the mixture is contacted with the solid support at a temperature of 25–90° C., preferably 60–80° C., and for a time period of 10–180 minutes, preferably up to 60 minutes. Hybridizations may be accelerated or improved by mixing the ligation mixture during hybridization, or by adding volume exclusion, chaotropic agents, tetramethylammonium chloride, or N,N,N, Trimethylglycine (Betaine monohydrate). When an array consists of dozens to hundreds of addresses, it is important that the correct ligation products have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed with buffer to remove unhybridized probe and optimize detection of captured probe. Alternatively, the array is washing sequentially.

Preferably, the solid support has a porous surface of a hydrophilic polymer composed of combinations of acrylamide with functional monomers containing carboxylate, aldehyde, or amino groups. This surface is formed by coating the support with a polyacrylamide based gel. Suitable formulations include mixtures of acrylamide/acrylic acid and N,N-dimethylacrylamide/glycerol monomethacrylate. A crosslinker, N,N'-methylenebisacryl-amide, is present at a level less than 50:1, preferably less than 500:1.

One embodiment of masking negative charges during the contacting of the solid support with the ligation mixture is achieved by using a divalent cation. The divalent cation can be $Mg^{2+}$, $Ca^{2+}$, $MN^{2+}$, or $Co^{2+}$. Typically, masking with the divalent cation is carried out by pre-hydridizing the solid support with hybridization buffer containing the cation at a minimum concentration of 10 mM for a period of 15 minutes at room temperature.

Another embodiment of masking negative charges during the contacting of the solid support with the ligation mixtures is achieved by carrying out the contacting at a pH at or below 6.0. This is effected by adding a buffer to the ligation mixtures before or during contact of it with the solid support. Suitable buffers include 2-(N-morpholino)ethanesulfonic acid (MES), sodium phosphate, and potassium phosphate.

Another embodiment of masking negative charges during the contacting of the solid support with the ligation mixture is achieved by capping free carboxylic acid groups with a neutralizing agent while preserving the hydrophillicity of the polymer. Suitable neutralizing agents include ethanolamine diethanolamine, propanolamine, dipropanolamine, isopropanolamine, and diisopropanolamine. Typically, masking with neutralizing agents is carried out by activating the carboxylic acid groups within the solid support with 1-[3-dimethylamino)propyl]-3-ethylcarbodiimide hydrochloride and N-hydroxysuccinimide followed by treatment with a solution of the neutralizing agent in a polar aprotic solvent such as chloroform, dichloromethane, or tetrahydrfuran.

By masking the negative charges in accordance with the present invention, an enhanced ability to detect the presence of ligated product in the presence of unligated oligonucleotide probes is achieved. In particular, the present invention is effective to detect the presence of ligated product in a ratio to unligated oligonucleotide probes of less than 1:300, preferably less than 1:900, more preferably less than 1:3000, and most preferably less than 1:9000.

In addition, by masking the negative charges in accordance with the present invention, an enhanced ability to detect the presence of a target nucleotide sequence from a non-target nucleotide sequence where the target nucleotide sequence differs from a non-target nucleotide sequence by a single base difference is achieved. In particular, the present invention is effective to detect target nucleotide sequence in a ratio of the target nucleotide sequence to non-target nucleotide sequence of less than 1:20, preferably less than 1:50, more preferably less than 1:100, most preferably less than 1:200.

It is important to select capture oligonucleotides and addressable nucleotide sequences which will hybridize in a stable fashion. This requires that the oligonucleotide sets and the capture oligonucleotides be configured so that the oligonucleotide sets hybridize to the target nucleotide sequences at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The detection phase of the process involves scanning and identifying if ligation of particular oligonucleotide sets occurred and correlating ligation to a presence or absence of the target nucleotide sequence in the test sample. Scanning can be carried out by scanning electron microscopy, confocal microscopy, charge-coupled device, scanning tunneling electron microscopy, infrared microscopy, atomic force microscopy, electrical conductance, and fluorescent or phosphor imaging. Correlating is carried out with a computer.

Another aspect of the present invention relates to a method of forming an array of oligonucleotides on a solid support. This method involves providing a support having an array of positions each suitable for attachment of an oligonucleotide. A linker or support (preferably non-hydrolyzable), suitable for coupling an oligonucleotide to the support at each of the array positions, is attached to the solid support. An array of oligonucleotides on a solid support is formed by a series of cycles of activating selected array positions for attachment of multimer nucleotides and attaching multimer nucleotides at the activated array positions.

Yet another aspect of the present invention relates to an array of oligonucleotides on a support per se. The solid support has an array of positions each suitable for an attachment of an oligonucleotide. A linker or support (preferably non-hydrolyzable), suitable for coupling an oligonucleotide to the solid support, is attached to the solid support at each of the array positions. An array of oligonucleotides are placed on a solid support with at least some of the array positions being occupied by oligonucleotides having greater than sixteen nucleotides.

In the method of forming arrays, multimer oligonucleotides from different multimer oligonucleotide sets are attached at different array positions on a solid support. As a result, the support has an array of positions with different groups of multimer oligonucleotides attached at different positions.

The 1,000 different addresses can be unique capture oligonucleotide sequences (e.g., 24-mer) linked covalently to the target-specific sequence (e.g., approximately 20- to 25-mer) of a LDR oligonucleotide probe. A capture oligonucleotide probe sequence does not have any homology to either the target sequence or to other sequences on genomes which may be present in the sample. This oligonucleotide probe is then captured by its addressable array-specific portion, a sequence complementary to the capture oligonucleotide on the addressable solid support array. The concept is shown in two possible formats, for example, for detection of the p53 R248 mutation (FIGS. 13A–C).

Figure 13A:
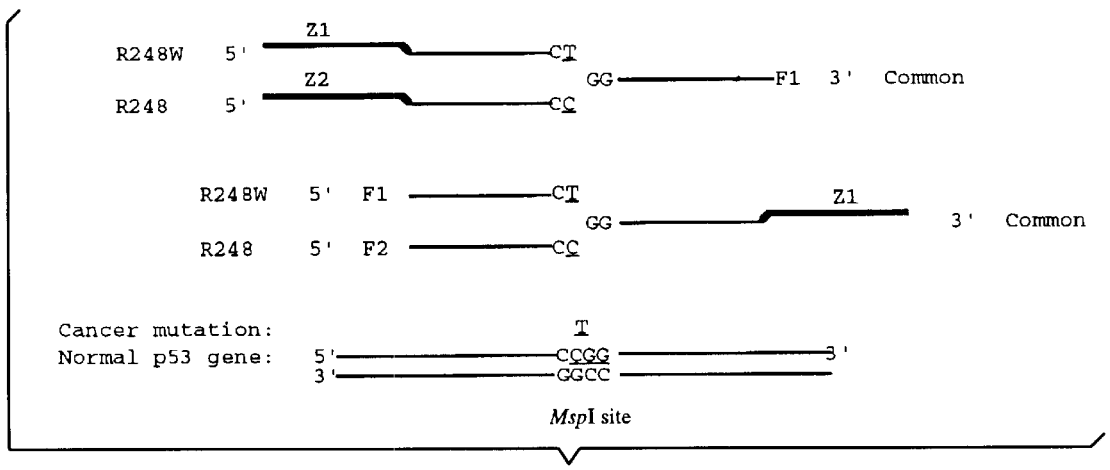
FIGS. 13A–C show two alternative formats for oligonucleotide probe capture.
Figure 13B:
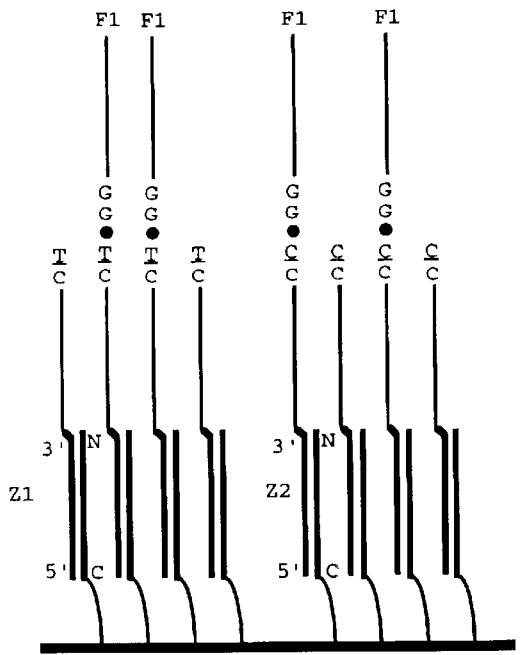
Figure 13C:
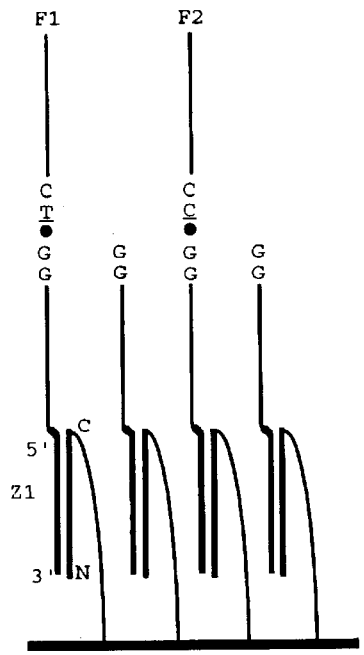

FIGS. 13A–C show two alternative formats for oligonucleotide probe design to identify the presence of a germ line mutation in codon 248 of the p53 tumor suppressor gene. The wild type sequence codes for arginine (R248), while the cancer mutation codes for tryptophan (R248W). The bottom part of the diagram is a schematic diagram of the capture oligonucleotide. The thick horizontal line depicts the membrane or surface containing the addressable array. The thin curved lines indicate a flexible linker arm. The thicker lines indicate a capture oligonucleotide sequence, attached to the solid surface in the C to N direction. For illustrative purposes, the capture oligonucleotides are drawn vertically, making the linker arm in section B appear "stretched". Since the arm is flexible, the capture oligonucleotide will be able to hybridize 5' to C and 3' to N in each case, as dictated by base pair complementarity. A similar orientation of oligonucleotide hybridization would be allowed if the oligonucleotides were attached to the membrane at the N-terminus. In this case, DNA/PNA hybridization would be in standard antiparallel 5' to 3' and 3' to 5'. Other modified sugar-phosphate backbones would be used in a similar fashion. FIG. 13B shows two LDR probes that are designed to discriminate wild type and mutant p53 by containing the discriminating base C or T at the 3' end. In the presence of the correct target DNA and Tth ligase, the discriminating probe is covalently attached to a common downstream oligonucleotide. The downstream oligonucleotide is fluorescently labeled. The discriminating oligonucleotides are distinguished by the presence of unique addressable array-specific portions, Z1 and Z2, at each of their 5' ends. A black dot indicates that target dependent ligation has taken place. After ligation, oligonucleotide probes may be captured by their complementary addressable array-specific portions at unique addresses on the array. Both ligated and unreacted oligonucleotide probes are captured by the oligonucleotide array. Unreacted fluorescently labeled common primers and target DNA are then washed away at a high temperature (approximately 65° C. to 80° C.) and low salt. Mutant signal is distinguished by detection of fluorescent signal at the capture oligonucleotide complementary to addressable array-specific portion Z1, while wild type signal appears at the capture oligonucleotide complementary to addressable array-specific portion Z2. Heterozygosity is indicated by equal signals at the capture oligonucleotides complementary to addressable array-specific portions Z1 and Z2. The signals may be quantified using a fluorescent imager. This format uses a unique address for each allele and may be preferred for achieving very accurate detection of low levels of signal (30 to 100 attomoles of LDR product). FIG. 13C shows the discriminating signals may be quantified using a fluorescent imager. This format uses a unique address where oligonucleotide probes are distinguished by having different fluorescent groups, F1 and F2, on their 5' end. Either oligonucleotide probe may be ligated to a common downstream oligonucleotide probe containing an addressable array-specific portion Z1 on its 3' end. In this format, both wild type and mutant LDR products are captured at the same address on the array, and are distinguished by their different fluorescence. This format allows for a more efficient use of the array and may be preferred when trying to detect hundreds of potential germline mutations.

The solid support can be made from a wide variety of materials. The substrate may be biological, nonbiological, organic, inorganic, or a combination of any of these, existing as particles, strands, precipitates, gels, sheets, tubing, spheres, containers, capillaries, pads, slices, films, plates, slides, discs, membranes, etc. The substrate may have any convenient shape, such as a disc, square, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polyethylene, polypropylene, polyvinyl chloride, poly(methyl acrylate), poly(methyl methacrylate), or combinations thereof. Other substrate materials will be readily apparent to those of ordinary skill in the art upon review of this disclosure. In a preferred embodiment, the substrate is flat glass or single-crystal silicon.

According to some embodiments, the surface of the substrate is etched using well known techniques to provide for desired surface features. For example, by way of the formation of trenches, v-grooves, mesa structures, raised platforms, or the like, the synthesis regions may be more closely placed within the focus point of impinging light, be provided with reflective "mirror" structures for maximization of light collection from fluorescent sources, or the like.

Surfaces on the solid substrate will usually, though not always, be composed of the same material as the substrate. Thus, the surface may be composed of any of a wide variety of materials, for example, polymers, plastics, ceramics, polysaccharides, silica or silica-based materials, carbon, metals, inorganic glasses, membranes, or composites thereof. The surface is functionalized with binding members which are attached firmly to the surface of the substrate. Preferably, the surface functionalities will be reactive groups such as silanol, olefin, amino, hydroxyl, aldehyde, keto, halo, acyl halide, or carboxyl groups. In some cases, such functionalities preexist on the substrate. For example, silica based materials have silanol groups, polysaccharides have hydroxyl groups, and synthetic polymers can contain a broad range of functional groups, depending on which monomers they are produced from. Alternatively, if the substrate does not contain the desired functional groups, such groups can be coupled onto the substrate in one or more steps.

A variety of commercially-available materials, which include suitably modified glass, plastic, or carbohydrate surfaces or a variety of membranes, can be used. Depending on the material, surface functional groups (e.g., silanol, hydroxyl, carboxyl, amino) may be present from the outset (perhaps as part of the coating polymer), or will require a separate procedure (e.g., plasma amination, chromic acid oxidation, treatment with a functionalized side chain alkyltrichlorosilane) for introduction of the functional group. Hydroxyl groups become incorporated into stable carbamate (urethane) linkages by several methods. Amino functions can be acylated directly, whereas carboxyl groups are activated, e.g., with N,N'-carbonyldiimidazole or water-soluble carbodiimides, and reacted with an amino-functionalized compound. As shown in FIG. 11, the solid supports can be membranes or surfaces with a starting functional group X. Functional group transformations can be carried out in a variety of ways (as needed) to provide group X* which represents one partner in the covalent linkage with group Y*. FIG. 11 shows specifically the grafting of PEG (i.e. polyethylene glycol), but the same repertoire of reactions can be used (however needed) to attach carbohydrates (with hydroxyl), linkers (with carboxyl), and/or oligonucleotides that have been extended by suitable functional groups (amino or carboxyl). In some cases, group X* or Y* is pre-activated (isolatable species from a separate reaction); alternatively, activation occurs in situ. Referring to PEG as drawn in FIG. 11, Y and Y* can be the same (homobifunctional) or different (heterobifunctional); in the latter case, Y can be protected for further control of the chemistry. Unreacted amino groups will be blocked by acetylation or succinylation, to ensure a neutral or negatively charged environment that "repels" excess unhybridized DNA. Loading levels can be determined by standard analytical methods. Fields, et al., "Principles and Practice of Solid-Phase Peptide Synthesis," *Synthetic Peptides: A User's Guide*, G. Grant, Editor, W. H. Freeman and Co.: New York. p. 77–183 (1992), which is hereby incorporated by reference.

One approach to applying functional groups on a silica-based support surface is to silanize with a molecule either having the desired functional group (e.g., olefin, amino, hydroxyl, aldehyde, keto, halo, acyl halide, or carboxyl) or a molecule A able to be coupled to another molecule B containing the desired functional group. In the former case, functionalizing of glass- or silica-based supports with, for example, an amino group is carried out by reacting with an amine compound such as 3-aminopropyl triethoxysilane, 3-aminopropylmethyldiethoxysilane, 3-aminopropyl dimethylethoxysilane, 3-aminopropyl trimethoxysilane, N-(2-aminoethyl)-3-aminopropylmethyl dimethoxysilane, N-(2-aminoethyl-3-aminopropyl) trimethoxysilane, aminophenyl trimethoxysilane, 4-aminobutyldimethyl methoxysilane, 4-aminobutyl triethoxysilane, aminoethylaminomethyphenethyl trimethoxysilane, or mixtures thereof. In the latter case, molecule A preferably contains olefinic groups, such as vinyl, acrylate, methacrylate, or allyl, while molecule B contains olefinic groups and the desired functional groups. In this case, molecules A and B are polymerized together. In some cases, it is desirable to modify the silanized surface to modify its properties (e.g., to impart biocompatibility and to increase mechanical stability). This can be achieved by addition of olefinic molecule C along with molecule B to produce a polymer network containing molecules A, B, and C.

Molecule A is defined by the following formula:

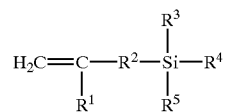

$R^1$ is H or $CH_3$ $R^2$ is (C=O)—O—$R^6$, aliphatic group with or without functional substituent(s), an aromatic group with or without functional substituent(s), or mixed aliphatic/aromatic groups with or without functional substituent(s);

$R^3$ is an O-alkyl, alkyl, or halogen group;

$R^4$ is an O-alkyl, alkyl, or halogen group;

$R^5$ is an O-alkyl, alkyl, or halogen group; and $R^6$ is an aliphatic group with or without functional substituent(s), an aromatic group with or without functional substituent(s), or mixed aliphatic/aromatic groups with or without functional substituent(s). Examples of Molecule A include 3-(trimethoxysilyl) propyl methacrylate, N-[3-(trimethoxysilyl)propyl]-N'-(4-vinylbenzyl)ethylenediamine, triethoxyvinylsilane, triethylvinylsilane, vinyltrichlorosilane, vinyltrimethoxysilane, and vinyltrimethylsilane.

Molecule B can be any monomer containing one or more of the functional groups described above. Molecule B is defined by the following formula:

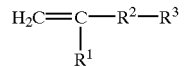

(i)
  $R^1$ is H or $CH_3$,
  $R^2$ is (C=O), and
  $R^3$ is OH or Cl.

or (ii)
  $R^1$ is H or $CH_3$ and
  $R^2$ is (C=O)—O—$R^4$, an aliphatic group with or without functional substituent(s), an aromatic group with or without functional substituent(s), and mixed aliphatic/aromatic groups with or without functional substituent(s); and
  $R^3$ is a functional group, such as OH, COOH, $NH_2$, halogen, SH, COCl, or active ester; and
  $R^4$ is an aliphatic group with or without functional substituent(s), an aromatic group with or without functional substituent(s), or mixed aliphatic/aromatic groups with or without functional substituent(s). Examples of molecule B include acrylic acid, acrylamide, methacrylic acid, vinylacetic acid, 4-vinylbenzoic acid, itaconic acid, allyl amine, allylethylamine, 4-aminostyrene, 2-aminoethyl methacrylate, acryloyl chloride, methacryloyl chloride, chlorostyrene, dichlorostyrene, 4-hydroxystyrene, hydroxymethyl styrene, vinylbenzyl alcohol, allyl alcohol, 2-hydroxyethyl methacrylate, or poly(ethylene glycol) methacrylate.

Molecule C can be any molecule capable of polymerizing to molecule A, molecule B, or both and may optionally contain one or more of the functional groups described above. Molecule C can be any monomer or cross-linker, such as acrylic acid, methacrylic acid, vinylacetic acid, 4-vinylbenzoic acid, itaconic acid, allyl amine, allylethylamine, 4-aminostyrene, 2-aminoethyl methacrylate, acryloyl chloride, methacryloyl chloride, chlorostyrene, dichlorostyrene, 4-hydroxystyrene, hydroxymethyl styrene, vinylbenzyl alcohol, allyl alcohol, 2-hydroxyethyl methacrylate, poly(ethylene glycol) methacrylate, methyl acrylate, methyl methacrylate, ethyl acrylate, ethyl methacrylate, styrene, 1-vinylimidazole, 2-vinylpyridine, 4-vinylpyridine, divinylbenzene, ethylene glycol dimethacryarylate, N,N'-methylenediacrylamide, N,N'-phenylenediacrylamide, 3,5-bis(acryloylamido) benzoic acid, pentaerythritol triacrylate, trimethylolpropane trimethacrylate, pentaerythritol tetraacrylate, trimethylolpropane ethoxylate (14/3 EO/OH) triacrylate, trimethyolpropane ethoxylate (7/3 EO/OH) triacrylate, triethylolpropane propoxylate (1 PO/OH) triacrylate, or trimethyolpropane propoxylate (2 PO/PH triacrylate).

Generally, the functional groups serve as starting points for oligonucleotides that will ultimately be coupled to the support. These functional groups can be reactive with an organic group that is to be attached to the solid support or it can be modified to be reactive with that group, as through the use of linkers or handles. The functional groups can also impart various desired properties to the support.

After functionalization (if necessary) of the support, tailor-made polymer networks containing activated functional groups that may serve as carrier sites for complementary oligonucleotide capture probes can be grafted to the support. The advantage of this approach is that the loading capacity of capture probes can thus be increased significantly, while physical properties of the intermediate solid-to-liquid phase can be controlled better. Parameters that are subject to optimization include the type and concentration of functional group-containing monomers, as well as the type and relative concentration of the crosslinkers that are used.

The surface of the functionalized substrate is preferably provided with a layer of linker molecules, although it will be understood that the linker molecules are not required elements of the invention. The linker molecules are preferably of sufficient length to permit polymers in a completed substrate to interact freely with molecules exposed to the substrate. The linker molecules should be 6–50 atoms long to provide sufficient exposure. The linker molecules may be, for example, aryl acetylene, ethylene glycol oligomers containing 2–10 monomer units, diamines, diacids, amino acids, or combinations thereof.

According to alternative embodiments, the linker molecules are selected based upon their hydrophilic/hydrophobic properties to improve presentation of synthesized polymers to certain receptors. For example, in the case of a hydrophilic receptor, hydrophilic linker molecules will be preferred to permit the receptor to approach more closely the synthesized polymer.

According to another alternative embodiment, linker molecules are also provided with a photocleavable group at any intermediate position. The photocleavable group is preferably cleavable at a wavelength different from the protective group. This enables removal of the various polymers following completion of the syntheses by way of exposure to the different wavelengths of light.

The linker molecules can be attached to the substrate via carbon-carbon bonds using, for example, (poly)trifluorochloroethylene surfaces or, preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized monolayer. In alternative embodiments, the linker molecules are adsorbed to the surface of the substrate.

Figure 12A:
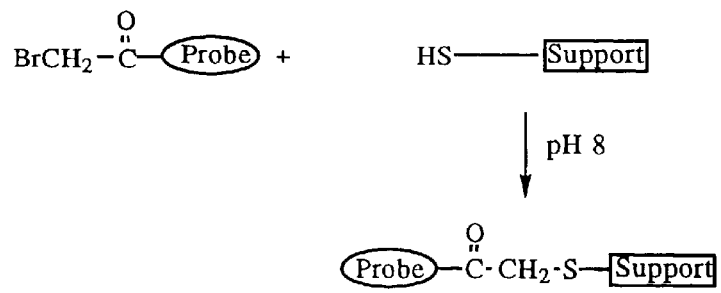
FIGS. 12A–C show proposed chemistries for covalent attachment of oligonucleotides to solid supports.
Figure 12B:
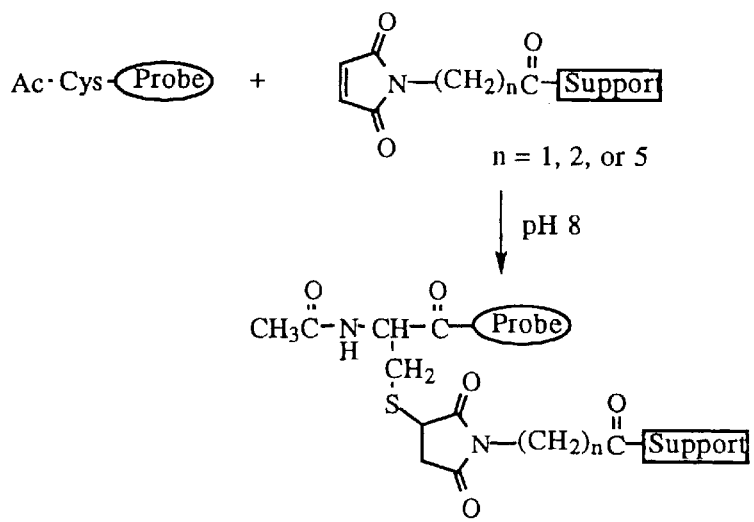
Figure 12C:
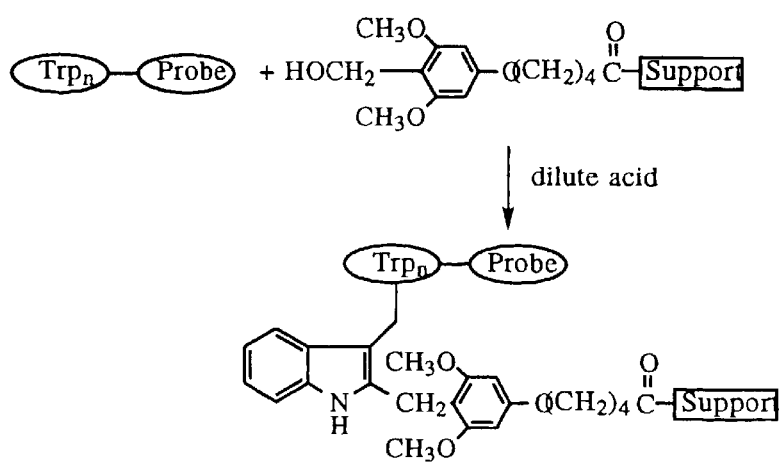

It is often desirable to introduce a PEG spacer with complementary functionalization, prior to attachment of the starting linker for DNA or PNA synthesis. G. Barany, et al., "Novel Polyethylene Glycol-polystyrene (PEG-PS) Graft Supports for Solid-phase Peptide Synthesis," ed. C. H. Schneider and A. N. Eberle., Leiden, The Netherlands: Escom Science Publishers. 267–268 (1993); Zalipsky, et al., "Preparation and Applications of Polyethylene Glycol-polystyrene Graft Resin Supports for Solid-phase Peptide Synthesis," *Reactive Polymers,* 22:243–58 (1994); J. M. Harris, ed. "Poly(Ethylene Glycol) Chemistry: Biotechnical and Biomedical Applications," (1992), Plenum Press: New York, which are hereby incorporated by reference. Similarly, dextran layers can be introduced as needed. Cass, et al., "Pilot, A New Peptide Lead Optimization Technique and Its Application as a General Library Method, in Peptides—Chemistry, Structure and Biology: Proceedings of the Thirteenth American Peptide Symposium", R. S. Hodges and J. A. Smith, Editor. (1994), Escom: Leiden, The Netherlands; Lofas, et al., "A Novel Hydrogel Matrix on Gold Surface Plasma Resonance Sensors for Fast and Efficient Covalent Immobilization of Ligands," *J. Chem. Soc. Chem. Commun.,* pp. 1526–1528 (1990), which are hereby incorporated by reference. Particularly preferred linkers are tris(alkoxy) benzyl carbonium ions with dilute acid due to their efficient and specific trapping with indole moieties. DNA oligonucleotides can be synthesized and terminated with a residue of the amino acid tryptophan, and conjugated efficiently to supports that have been modified by tris(alkoxy)benzyl ester (hypersensitive acid labile ("HAL")) or tris(alkoxy) benzylamide ("PAL") linkers [F. Albericio, et al., *J. Org. Chem.,* 55:3730–3743 (1990); F. Albericio and G. Barany, *Tetrahedron Lett.,* 32:1015–1018 (1991)], which are hereby incorporated by reference). Other potentially rapid chemistries involve reaction of thiols with bromoacetyl or maleimido functions. In one variation, the terminus of amino functionalized DNA is modified by bromoacetic anhydride, and the bromoacetyl function is captured by readily established thiol groups on the support. Alternatively, an N-acetyl, S-tritylcysteine residue coupled to the end of the probe provides, after cleavage and deprotection, a free thiol which can be captured by a maleimido group on the support. As shown in FIG. 12, chemically synthesized probes can be extended, on either end. Further variations of the proposed chemistries are readily envisaged. FIG. 12A shows that an amino group on the probe is modified by bromoacetic anhydride; the bromoacetyl function is captured by a thiol group on the support. FIG. 12B shows that an N-acetyl, S-tritylcysteine residue coupled to the end of the probe provides, after cleavage and deprotection, a free thiol which is captured by a maleimido group on the support. FIG. 12C shows a probe containing an oligo-tryptophanyl tail (n=1 to 3), which is captured after treatment of a HAL-modified solid support with dilute acid.

To prepare the arrays of the present invention, the solid supports must be charged with DNA oligonucleotides or PNA oligomers. This is achieved either by attachment of pre-synthesized probes, or by direct assembly and side-chain deprotection (without release of the oligomer) onto the support. Further, the support environment needs to be such as to allow efficient hybridization. Toward this end, two factors may be identified: (i) sufficient hydrophilic character of support material (e.g., PEG or carbohydrate moieties) and (ii) flexible linker arms (e.g., hexaethylene oxide or longer PEG chains) separating the probe from the support backbone. It should be kept in mind that numerous ostensibly "flat surfaces" are quite thick at the molecular level. Lastly, it is important that the support material not provide significant background signal due to non-specific binding or intrinsic fluorescence.

The linker molecules and monomers used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups, an additional step of reactivation will be required. In some embodiments, this will be done by heating.

The protective group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxycarbonyl ("NVOC"), 2-nitrobenzyloxycarbonyl ("NBOC"), Benzyloxycarbonyl ("BOC"), fluorenylmethoxycarbonyl ("FMOC"), or α,α-dimethyl-dimethoxybenzyloxycarbonyl ("DDZ") is used. In one embodiment, a nitro aromatic compound containing a benzylic hydrogen ortho to the nitro group is used, i.e., a chemical of the form:

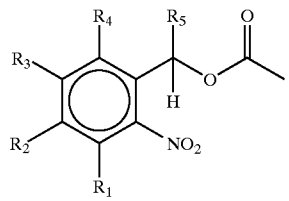

where $R_1$ is alkoxy, alkyl, halo, aryl, alkenyl, or hydrogen; $R_2$ is alkoxy, alkyl, halo, aryl, nitro, or hydrogen; $R_3$ is alkoxy, alkyl, halo, nitro, aryl, or hydrogen; $R_4$ is alkoxy, alkyl, hydrogen, aryl, halo, or nitro; and $R_5$ is alkyl, alkynyl, cyano, alkoxy, hydrogen, halo, aryl, or alkenyl. Other materials which may be used include o-hydroxy-α-methyl cinnamoyl derivatives. Photoremovable protective groups are described in, for example, Patchornik, *J. Am. Chem. Soc.* 92:6333 (1970) and Amit et al., *J. Org. Chem.* 39:192 (1974), both of which are hereby incorporated by reference.

In an alternative embodiment, the positive reactive group is activated for reaction with reagents in solution. For example, a 5-bromo-7-nitro indoline group, when bound to a carbonyl, undergoes reaction upon exposure to light at 420 nm.

In a second alternative embodiment, the reactive group on the linker molecule is selected from a wide variety of negative light-reactive groups including a cinnamete group.

Alternatively, the reactive group is activated or deactivated by electron beam lithography, x-ray lithography, or any other radiation. A suitable reactive group for electron beam lithography is a sulfonyl group. Other methods may be used including, for example, exposure to a current source. Other reactive groups and methods of activation may be used in view of this disclosure.

The linking molecules are preferably exposed to, for example, light through a suitable mask using photolithographic techniques of the type known in the semiconductor industry and described in, for example, Sze, *VLSI Technology*, McGraw-Hill (1983), and Mead et al., *Introduction to VLSI Systems*, Addison-Wesley (1980), which are hereby incorporated by reference for all purposes. The light may be directed at either the surface containing the protective groups or at the back of the substrate, so long as the substrate is transparent to the wavelength of light needed for removal of the protective groups.

The mask is in one embodiment a transparent support material selectively coated with a layer of opaque material. Portions of the opaque material are removed, leaving opaque material in the precise pattern desired on the substrate surface. The mask is brought directly into contact with the substrate surface. "Openings" in the mask correspond to locations on the substrate where it is desired to remove photoremovable protective groups from the substrate. Alignment may be performed using conventional alignment techniques in which alignment marks are used accurately to overlay successive masks with previous patterning steps, or more sophisticated techniques may be used. For example, interferometric techniques such as the one described in Flanders et al., "A New Interferometric Alignment Technique." *App. Phys. Lett.* 31:426–428 (1977), which is hereby incorporated by reference, may be used.

To enhance contrast of light applied to the substrate, it is desirable to provide contrast enhancement materials between the mask and the substrate according to some embodiments. This contrast enhancement layer may comprise a molecule which is decomposed by light such as quinone diazide or a material which is transiently bleached at the wavelength of interest. Transient bleaching of materials will allow greater penetration where light is applied, thereby enhancing contrast. Alternatively, contrast enhancement may be provided by way of a cladded fiber optic bundle.

The light may be from a conventional incandescent source, a laser, a laser diode, or the like. If non-collimated sources of light are used, it may be desirable to provide a thick- or multi-layered mask to prevent spreading of the light onto the substrate. It may, further, be desirable in some embodiments to utilize groups which are sensitive to different wavelengths to control synthesis. For example, by using groups which are sensitive to different wavelengths, it is possible to select branch positions in the synthesis of a polymer or eliminate certain masking steps.

Alternatively, the substrate may be translated under a modulated laser or diode light source. Such techniques are discussed in, for example, U.S. Pat. No. 4,719,615 to Feyrer et al., which is hereby incorporated by reference. In alternative embodiments, a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled to permit light to contact selected regions of the substrate. Alternatively, synthesis may take place on the end of a series of optical fibers to which light is selectively applied. Other means of controlling the location of light exposure will be apparent to those of skill in the art.

The development of linkers and handles for peptide synthesis is described in Fields, et al., "Principles and Practice of Solid-Phase Peptide Synthesis, "*Synthetic Peptides: A User's Guide,* G. Grant, Editor. W. H. Freeman and Co.: New York. p. 77–183 (1992); G. Barany, et al., "Recent Progress on Handles and Supports for Solid-phase Peptide Synthesis", *Peptides-Chemistry, Structure and Biology:*

Proceedings of the Thirteenth American Peptide Symposium. R. S. Hodges and J. A. Smith, Editor. Escom Science Publishers: Leiden, The Netherlands pp.1078–80 (1994), which are hereby incorporated by reference. This technology is readily extendable to DNA and PNA. Of particular interest is the development of PAL (Albericio, et al., "Preparation and Application of the 5-(4-(9-Fluorenylmethyloxycarbonyl)Aminomethyl-3,5-Dimethoxyphenoxy)Valeric Acid (PAL) Handle for the Solid-phase Synthesis of C-terminal Peptide Amides under Mild Conditions," *J. Org. Chem.,* 55:3730–3743 (1990), which is hereby incorporated by reference, and ester (HAL) (Albericio, et al., "Hypersensitive Acid-labile (HAL) Tris (alkoxy)Benzyl Ester Anchoring for Solid-phase Synthesis of Protected Peptide Segments," *Tetrahedron Lett.,* 32:1015–1018 (1991), which is hereby incorporated by reference, linkages, which upon cleavage with acid provide, respectively, C-terminal peptide amides, and protected peptide acids that can be used as building blocks for so-called segment condensation approaches. The stabilized carbonium ion generated in acid from cleavage of PAL or HAL linkages can be intercepted by tryptophanyl-peptides. While this reaction is a nuisance for peptide synthesis and preventable (in part) by use of appropriate scavengers, it has the positive application of chemically capturing oligo-Trp-end-labelled DNA and PNA molecules by HAL-modified surfaces.

The art recognizes several approaches to making oligonucleotide arrays. Southern, et al., "Analyzing and Comparing Nucleic Acid Sequences by Hybridization to Arrays of Oligonucleotides: Evaluation using Experimental Models," *Genomics,* 13:1008–1017 (1992); Fodor, et al., "Multiplexed Biochemical Assays with Biological Chips," *Nature,* 364:555–556 (1993); Khrapko, et al., "A Method for DNA Sequencing by Hybridization with Oligonucleotide Matrix," *J. DNA Seq. Map.,* 1:375–388 (1991); Van Ness, et al., "A Versatile Solid Support System for Oligodeoxynucleoside Probe-based Hybridization Assays," *Nucleic Acids Res.,* 19:3345–3350 (1991); Zhang, et al., "Single-base Mutational Analysis of Cancer and Genetic Diseases Using Membrane Bound Modified Oligonucleotides," *Nucleic Acids Res.,* 19:3929–3933 (1991); K. Beattie, "Advances in Genosensor Research," *Clin. Chem.* 41(5):700–06 (1995), which are hereby incorporated by reference. These approaches may be divided into three categories: (i) Synthesis of oligonucleotides by standard methods and their attachment one at a time in a spatial array; (ii) Photolithographic masking and photochemical deprotection on a silicon chip, to allow for synthesis of short oligonucleotides (Fodor, et al., "Multiplexed Biochemical Assays with Biological Chips," *Nature,* 364:555–556 (1993) and R. J. Lipshutz, et al., "Using Oligonucleotide Probe Arrays To Assess Genetic Diversity," *Biotechniques* 19:442–447 (1995), which are hereby incorporated by reference); and (iii) Physical masking to allow for synthesis of short oligonucleotides by addition of single bases at the unmasked areas (Southern, et al., "Analyzing and Comparing Nucleic Acid Sequences by Hybridization to Arrays of Oligonucleotides: Evaluation Using Experimental Models," *Genomics,* 13:1008–1017 (1992), Maskos, et al., "A Study of Oligonucleotide Reassociation Using Large Arrays of Oligonucleotides Synthesised on a Glass Support," *Nucleic Acids Res.,* 21:4663–4669 (1993), which are hereby incorporated by reference).

Although considerable progress has been made in constructing oligonucleotide arrays, some containing as many as 256 independent addresses, these procedures are less preferred, for detecting specific DNA sequences by hybridizations. More particularly, arrays containing longer oligonucleotides can currently be synthesized only by attaching one address at a time and, thus, are limited in potential size. Current methods for serially attaching an oligonucleotide take about 1 hour, thus an array of 1,000 addresses would require over 40 days of around-the-clock work to prepare. Arrays containing short oligonucleotides of 8- to 10- mers do not have commercial applicability, because longer molecules are needed to detect single base differences effectively.

These prior procedures may still be useful to prepare said supports carrying an array of oligonucleotides for the method of detection of the present invention. However, there are more preferred approaches.

It is desirable to produce a support with a good loading of oligonucleotide or PNA oligomer in a relatively small, but well-defined area. Current, commercially available fluorescent imagers can detect a signal as low as 3 attomoles per 50 $\mu$m square pixel. Thus, a reasonable size address or "spot" on an array would be about 4×4 pixels, or 200 $\mu$m square. Smaller addresses could be used with CCD detection. The limit of detection for such an address would be about 48 attomoles per "spot", which is comparable to the 100 attomole detection limit using a fluorescent DNA sequencing machine. The capacity of oligonucleotides which can be loaded per 200 $\mu$m square will give an indication of the potential signal to noise ratio. A loading of 20 fmoles would give a signal to noise ratio of about 400 to 1, while 200 fmoles would allow for a superb signal to noise ratio of about 4000 to 1. The oligonucleotide or PNA oligomer should be on a flexible "linker arm" and on the "outside" or "surface" of the solid support for easier hybridizations. The support should be non-fluorescent, and should not interfere with hybridization nor give a high background signal due to nonspecific binding.

The complementary capture oligonucleotide addresses on the solid supports can be either DNA or PNA. PNA-based capture is preferred over DNA-based capture, because PNA/DNA duplexes are much stronger than DNA/DNA duplexes, by about 1° C./base-pair. M. Egholm, et al., "PNA Hybridizes to Complementary Oligonucleotides Obeying the Watson-Crick Hydrogen-bonding Rules," *Nature,* 365:566–568 (1993), which is hereby incorporated by reference. Thus, for a 24-mer DNA/DNA duplex with $T_m$=72° C., the corresponding duplex with one PNA strand would have a "predicted" $T_m$=96° C. (the actual melting point might be slightly lower as the above "rule of thumb" is less accurate as melting points get over 80° C.). Additionally, the melting difference between DNA/DNA and PNA/DNA becomes even more striking at low salt.

The melting temperature of DNA/DNA duplexes can be estimated as [4n(G.C)+2m(A.T)]° C. Oligonucleotide capture can be optimized by narrowing the $T_m$ difference between duplexes formed by capture oligonucleotides and the complementary addressable array-specific portions hybridized to one another resulting from differences in G.C/A.T content. Using 5-propynyl-dU in place of thymine increases the $T_m$ of DNA duplexes an average of 1.7° C. per substitution. Froehler, et al., "Oligonucleotides Containing C-5 Propyne Analogs of 2'-deoxyuridine and 2'-deoxycytidine," *Tetrahedron Lett.,* 33:5307–5310 (1992) and J. Sagi, et al., *Tetrahedron Letters,* 34:2191 (1993), which are hereby incorporated by reference. The same substitution in the capture scheme should lower the $T_m$ difference between the components of such duplexes and raise the $T_m$ for all of the duplexes. Phosphoramidite derivatives of 5-propynyl-dU having the following structure can be prepared according to the immediately preceding Froehler and Sagi references, which are hereby incorporated by reference.

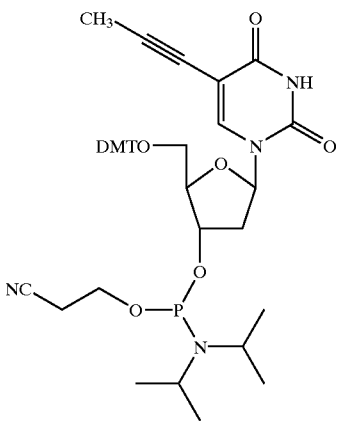

The 5-propynyluracil PNA monomer with Fmoc amino protection can be made by the following synthesis (where DMF is N,N'-dimethylformamide, DCC is N,N'-dicyclohexylcarbodiimide, HOBt is 1-hydroxybenzotriazole, and THF is tetrahydrofuran):

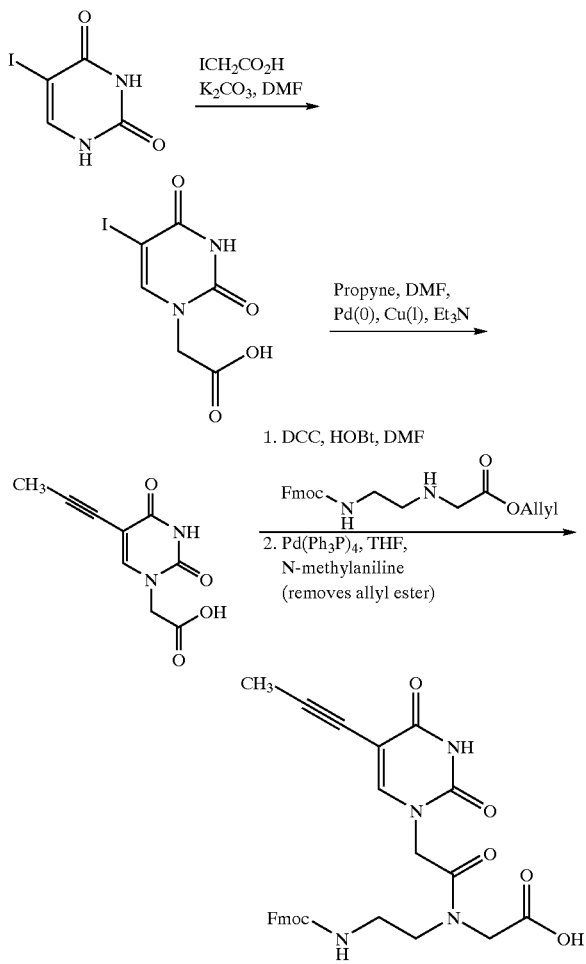

Using the methods described by Egholm, et al., "Peptide Nucleic Acids (PNA). Oligonucleotide Analogues with an Achiral Peptide Backbone," *J. Am. Chem. Soc.,* 114:1895–1897 (1992) and Egholm, et al., "Recognition of Guanine and Adenine in DNA by Cytosine and Thymine Containing Peptide Nucleic Acids (PNA)," *J. Am. Chem. Soc.,* 114:9677–9678 (1992), which are hereby incorporated by reference. The synthesis scheme above describes the preparation of a PNA monomer having a 5-propynyl-uracil base component. 5-Iodouracil is first alkylated with iodoacetic acid, and, then, the propynl group is coupled to the base moiety by a Pd/Cu catalyst. The remaining steps in the scheme follow from the above-referenced methods. These monomers can be incorporated into synthetic DNA and PNA strands.

There are two preferred general approaches for synthesizing arrays. In the first approach, fill-length DNA oligonucleotides or PNA oligomers are prepared and are subsequently linked covalently to a solid support or membrane. In the second approach, specially designed PNA oligomers or DNA oligonucleotides are constructed by sequentially adding multimers to the support. These multimers are added to specific rows or columns on a solid support or membrane surface. The resulting "checkerboard" pattern generates unique addressable arrays of full length PNA or DNA.

FIGS. 14–16 show different modes of preparing full-length DNA oligonucleotides or PNA oligomers and, subsequently, linking those full length molecules to the solid support.

Figure 14A:
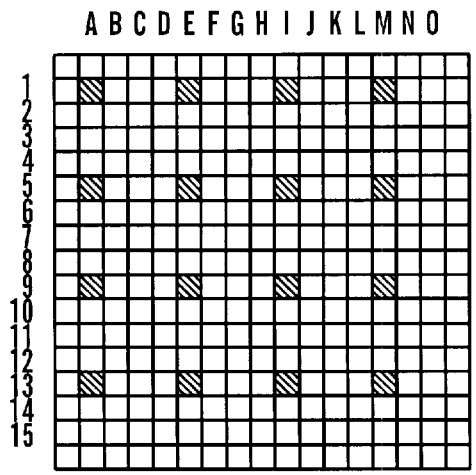
FIGS. 14A–E depict a protocol for constructing an 8×8 array of oligomers by spotting full-length, individual 24 mer oligomers at various sites on a solid support.
Figure 14B:
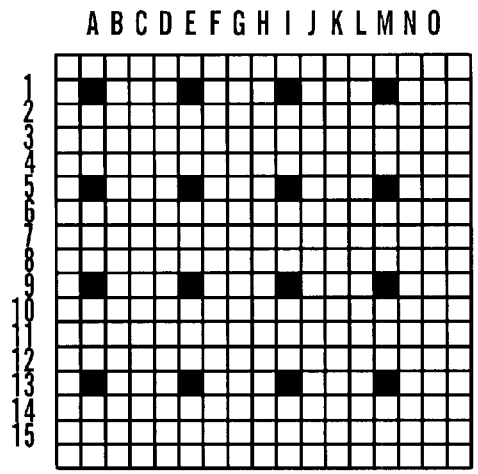
Figure 14C:
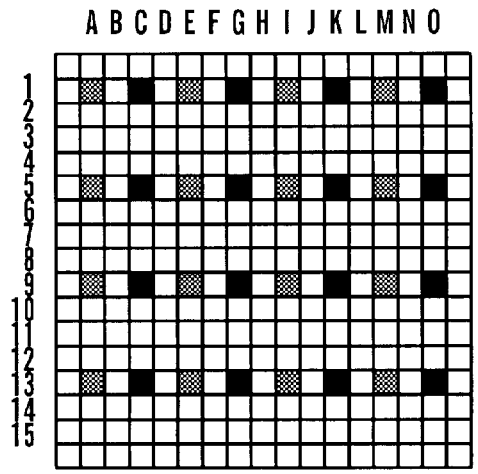
Figure 14D:
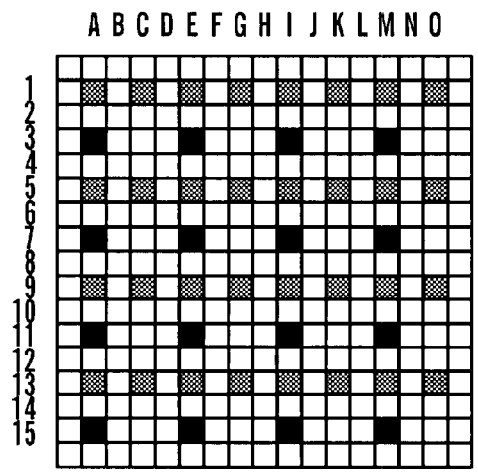
Figure 14E:
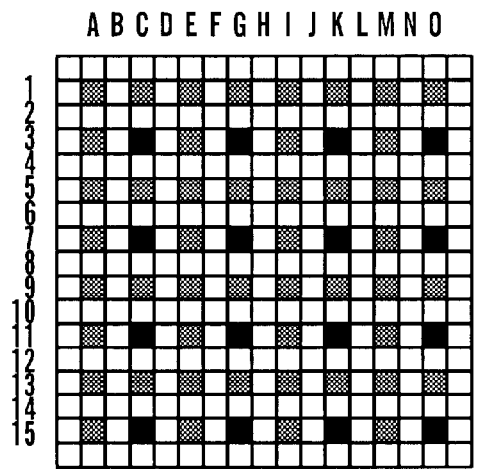

FIGS. 14A–E depict a method for constructing an array of DNA or PNA oligonucleotides by coupling individual full-length oligonucleotides to the appropriate locations in a grid. The array of FIG. 14A shows the pattern of oligonucleotides that would be generated if oligonucleotides are coupled to sixteen 200 $\mu$m×200 $\mu$m regions of the array surface. Each individual 200 $\mu$m×200 $\mu$m region contains DNA or PNA with a unique sequence which is coupled to the surface. The individual square regions will be separated from adjacent squares by 200 $\mu$m. The array of FIG. 14A can thus support 64 (8×8) different oligonucleotides in an 3 mm by 3 mm area. In order to multiplex the construction of the array, 16 squares separated by a distance of 800 $\mu$m will be coupled simultaneously to their specific oligonucleotides. Therefore, the 8×8 grid could be constructed with only 4 machine steps as shown in FIGS. 14B–14E. In these diagrams, the dark squares represent locations that are being altered in the current synthesis step, while the hatched squares represent regions which have been synthesized in earlier steps. The first step (FIG. 14B) would immobilize oligonucleotides at locations A1, E1, I1, M1, A5, E5, I5, M5, A9, E9, I9, M9, A13, E13, I13, and M13 simultaneously. In the next step (FIG. 14C), the machine would be realigned to start in Column C. After having completed Row 1, the next step (FIG. 14D) would start at Row 3. Finally, the last 16 oligonucleotides would be immobilized in order to complete the 8×8 grid (FIG. 14E). Thus, the construction of the 8×8 array could be reduced to 4 synthesis steps instead of 64 individual spotting reactions. This method would be easily extended and an apparatus capable of spotting 96 oligomers simultaneously could be used rapidly to construct larger arrays.

FIGS. 15A–E represent a perspective dimensional view of the array construction process described in FIG. 14. In FIGS. 15A–E, the construction of a 4×4 (16) array using a machine capable of spotting four different 24-mers simultaneously is depicted. First, as shown in FIG. 15A, the machine attaches 4 oligomers at locations A1, E1, A5, and E5. Next, as shown in FIG. 15B, the machine is shifted horizontally and attaches 4 oligomers at locations C1, G1, C5, and G5. Next, as shown in FIG. 15C, the machine is repositioned and attaches 4 oligomers at locations A3, E3, A7, and E7. Finally, as shown in FIG. 15D, the machine attaches the 4 remaining oligomers at positions C3, G3, C7, and G7. The completed array contains sixteen 24-mers as shown in the perspective view of FIG. 15E.

FIGS. 16A–C show views for an application apparatus 2 capable of simultaneously coupling 16 different oligonucleotides to different positions on an array grid G as shown in FIG. 14. The black squares in the top view (FIG. 16A) represent sixteen 200 μm×200 μm regions that are spatially separated from each other by 600 μm. The apparatus shown has 16 input ports which would allow tubes containing different oligonucleotides to fill the funnel-shaped chambers above different locations on the array. The side views (FIGS. 16B–C, taken along lines 16B–16B and 16C–16C, of FIG. 16A, respectively) of the apparatus demonstrate that funnel shaped chambers 4 align with the appropriate region on the array below the apparatus. In addition, two valves 6 and 8 (hatched squares in FIGS. 16A–C) control the flow of fluid in the 16 independent reaction chambers. One valve 6 controls the entry of fluids from the input port 10, while the other valve 8 would be attached to a vacuum line 12 in order to allow loading and clearing of the reaction chamber 4. The apparatus would first be aligned over the appropriate 200 μm×200 μm regions of the array. Next, the entire apparatus is firmly pressed against the array, thus forming a closed reaction chamber above each location. The presence of raised 10 μm ridges R around each location on the array ensures the formation of a tight seal which would prevent leakage of oligomers to adjacent regions on the array. Next, the valve 8 to vacuum line 12 would be opened, while the valve 10 from the input solution port 10 would be closed. This would remove air from the reaction chamber 4 and would create a negative pressure in the chamber. Then, the valve 8 to vacuum line 12 would be closed and the valve 10 from the input solution port 10 would be opened. The solution would flow into the reaction chamber 4 due to negative pressure. This process eliminates the possibility of an air bubble forming within the reaction chamber 4 and ensures even distribution of oligonucleotides across the 200 μm×200 μm region. After the oligonucleotides have been coupled to the activated array surface, the input valve 6 would be closed, the valve 8 to vacuum line 12 would be opened, and the apparatus would be lifted from the array surface in order to remove completely any excess solution from the reaction chamber. A second apparatus can now be realigned for the synthesis of the next 16 locations on the array.

FIGS. 15 to 26 show different modes of constructing PNA oligomers or DNA oligonucleotides on a solid support by sequentially adding, respectively, PNA or DNA, multimers to the support.

As an example of assembling arrays with multimers, such assembly can be achieved with tetramers. Of the 256 ($4^4$) possible ways in which four bases can be arranged as tetramers, 36 that have unique sequences can be selected. Each of the chosen tetramers differs from all the others by at least two bases, and no two dimers are complementary to each other. Furthermore, tetramers that would result in self-pairing or hairpin formation of the addresses have been eliminated.

The final tetramers are listed in Table 1 and have been numbered arbitrarily from 1 to 36. This unique set of tetramers are used as design modules for the sometimes desired 24-mer capture oligonucleotide address sequences. The structures can be assembled by stepwise (one base at a time) or convergent (tetramer building blocks) synthetic strategies. Many other sets of tetramers may be designed which follow the above rules. The segment approach is not uniquely limited to tetramers, and other units, i.e. dimers, trimers, pentamers, or hexamers could also be used.

TABLE 1

List of tetramer PNA sequences and complementary DNA sequences, which differ from each other by at least 2 bases.

| Number | Sequence (N-C) | Complement (5'–3') | G + C |
|---|---|---|---|
| 1. | TCTG | CAGA | 2 |
| 2. | TGTC | GACA | 2 |
| 3. | TCCC | GGGA | 3 |
| 4. | TGCG | CGCA | 3 |
| 5. | TCGT | ACGA | 2 |
| 6. | TTGA | TCAA | 1 |
| 7. | TGAT | ATCA | 1 |
| 8. | TTAG | CTAA | 1 |
| 9. | CTTG | CAAG | 2 |
| 10. | CGTT | AACG | 2 |
| 11. | CTCA | TGAG | 2 |
| 12. | CACG | CGTG | 3 |
| 13. | CTGT | ACAG | 2 |
| 14. | CAGC | GCTG | 3 |
| 15. | CCAT | ATGG | 2 |
| 16. | CGAA | TTCG | 2 |
| 17. | GCTT | AAGC | 2 |
| 18. | GGTA | TACC | 2 |
| 19. | GTCT | AGAC | 2 |
| 20. | GACC | GGTC | 3 |
| 21. | GAGT | ACTC | 2 |
| 22. | GTGC | GCAC | 3 |
| 23. | GCAA | TTGC | 2 |
| 24. | GGAC | GTCC | 3 |
| 25. | AGTG | CACT | 2 |
| 26. | AATC | GATT | 1 |
| 27. | ACCT | AGGT | 2 |
| 28. | ATCG | CGAT | 2 |
| 29. | ACGG | CCGT | 3 |
| 30. | AGGA | TCCT | 2 |
| 31. | ATAC | GTAT | 1 |
| 32. | AAAG | CTTT | 1 |
| 33. | CCTA | TAGG | 2 |
| 34. | GATG | CATC | 2 |
| 35. | AGCC | GGCT | 3 |
| 36. | TACA | TGTA | 1 |

Note that the numbering scheme for tetramers permits abbreviation of each address as a string of six numbers (e.g., second column of Table 2 infra). The concept of a 24-mer address designed from a unique set of 36 tetramers (Table 1) allows a huge number of possible structures, $36^6$=2,176,782,336.

Figure 17:
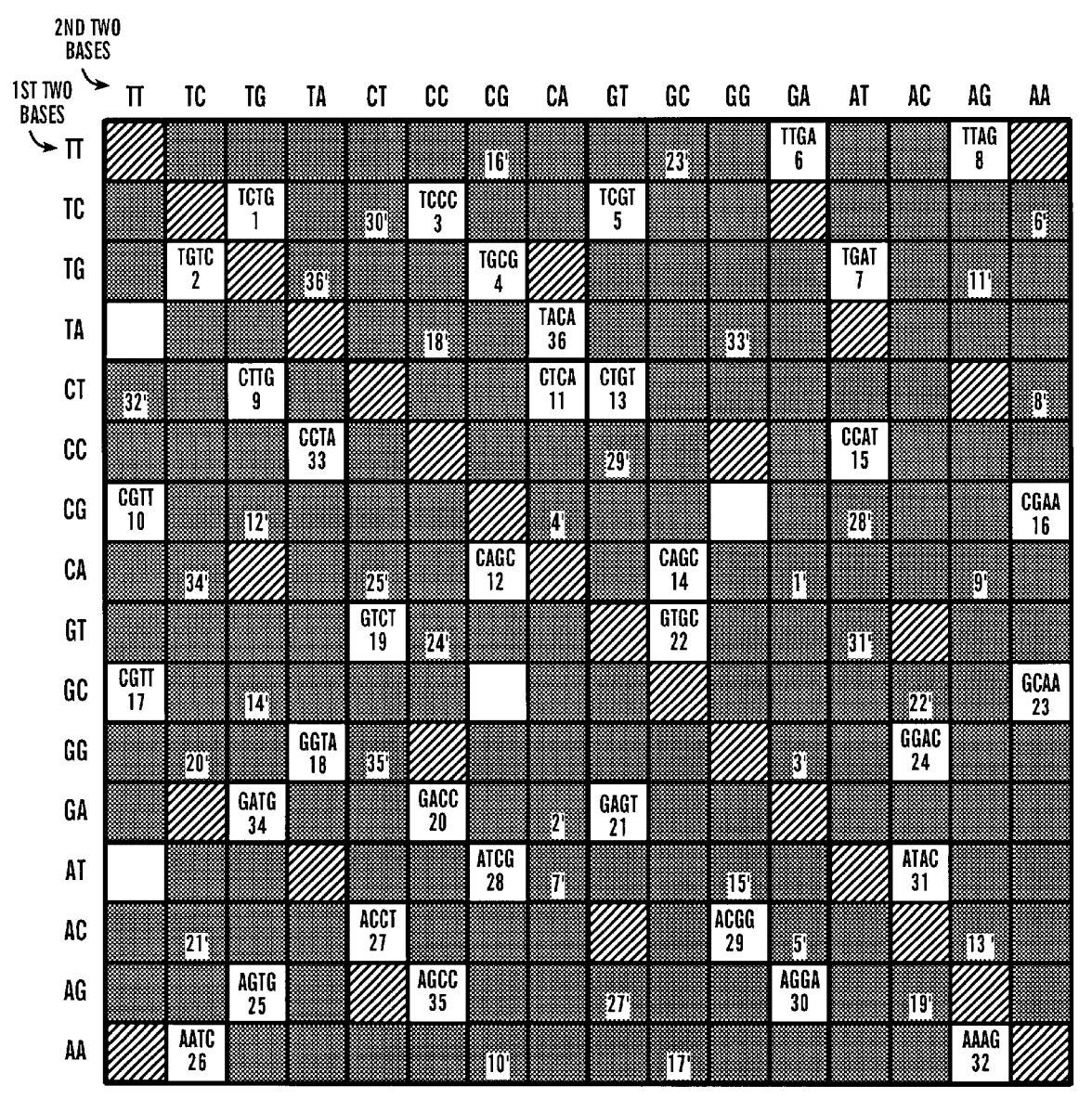

FIG. 17 shows one of the many possible designs of 36 tetramers which differ from each other by at least 2 bases. The checkerboard pattern shows all 256 possible tetramers. A given square represents the first two bases on the left followed by the two bases on the top of the checkerboard. Each tetramer must differ from each other by at least two bases, and should be non-complementary. The tetramers are shown in the white boxes, while their complements are listed as (number)'. Thus, the complementary sequences GACC (20) and GGTC (20') are mutually exclusive in this scheme. In addition, tetramers must be non-palindromic, e.g., TCGA (darker diagonal line boxes), and non-repetitive, e.g., CACA (darker diagonal line boxes from upper left to lower right). All other sequences which differ from the 36 tetramers by only 1 base are shaded in light gray. Four potential tetramers (white box) were not chosen as they are either all A.T or G.C bases. However, as shown below, the $T_m$ values of A.T bases can be raised to almost the level of G.C bases. Thus, all A.T or G.C base tetramers (including the ones in white boxes)

could potentially be used in a tetramer design. In addition, thymine can be replaced by 5-propynyl uridine when used within capture oligonucleotide address sequences as well as in the oligonucleotide probe addressable array-specific portions. This would increase the $T_m$ of an A.T base pair by ~1.7° C. Thus, $T_m$ values of individual tetramers should be approximately 15.1° C. to 15.7° C. $T_m$ values for the full length 24-mers should be 95° C. or higher.

To illustrate the concept, a subset of six of the 36 tetramer sequences were used to construct arrays: 1=TGCG; 2=ATCG; 3=CAGC; 4=GGTA; 5=GACC; and 6=ACCT. This unique set of tetramers can be used as design modules for the required 24-mer addressable array-specific portion and 24-mer complementary capture oligonucleotide address sequences. This embodiment involves synthesis of five addressable array-specific portion (sequences listed in Table 2). Note that the numbering scheme for tetramers allows abbreviation of each portion (referred to as "Zip #") as a string of six numbers (referred to as "zip code").

TABLE 2

List of all 5 DNA/PNA oligonucleotide address sequences.

| Zip # | Zip code | Sequence (5' → 3' or NH$_2$ → COOH) | G + C |
|---|---|---|---|
| Zip 11 | 1-4-3-6-6-1 | TGCG-GGTA-CAGC-ACCT-ACCT-TGCG (SEQ. ID. No. 1) | 15 |
| Zip 12 | 2-4-4-6-1-1 | ATCG-GGTA-GGTA-ACCT-TGCG-TGCG (SEQ. ID. No. 2) | 14 |
| Zip 13 | 3-4-5-6-2-1 | CAGC-GGTA-GACC-ACCT-ATCG-TGCG (SEQ. ID. No. 3) | 15 |
| Zip 14 | 4-4-6-6-3-1 | GGTA-GGTA-ACCT-ACCT-CAGC-TGCG (SEQ. ID. No. 4) | 14 |
| Zip 15 | 5-4-1-6-4-1 | GACC-GGTA-TGCG-ACCT-GGTA-TGCG (SEQ. ID. No. 5) | 15 |

Each of these oligomers contains a hexaethylene oxide linker arm on their 5' termini [P. Grossman, et al., *Nucl. Acids Res.*, 22:4527–4534 (1994), which is hereby incorporated by reference], and ultimate amino-functions suitable for attachment onto the surfaces of glass slides, or alternative materials. Conjugation methods will depend on the free surface functional groups [Y. Zhang, et al., *Nucleic Acids Res.*, 19:3929–3933 (1991) and Z. Guo, et al., *Nucleic Acids Res.*, 34:5456–5465 (1994), which are hereby incorporated by reference].

Synthetic oligonucleotides (normal and complementary directions, either for capture hybridization or hybridization/ligation) are prepared as either DNA or PNA, with either natural bases or nucleotide analogues. Such analogues pair with perfect complementarity to the natural bases but increase $T_m$ values (e.g., 5-propynyl-uracil).

Each of the capture oligonucleotides have substantial sequence differences to minimize any chances of cross-reactivity—see FIG. 17 and Table 1. Rather than carrying out stepwise synthesis to introduce bases one at a time, protected PNA tetramers can be used as building blocks. These are easy to prepare; the corresponding protected oligonucleotide intermediates require additional protection of the internucleotide phosphate linkages. Construction of the 24-mer at any given address requires only six synthetic steps with a likely improvement in overall yield by comparison to stepwise synthesis. This approach eliminates totally the presence of failure sequences on the support, which could occur when monomers are added one-at-a-time to the surface. Hence, in contrast to previous technologies, the possibilities for false signals are reduced. Moreover, since failure sequences at each address are shorter and lacking at least four bases, there is no risk that these will interfere with correct hybridization or lead to incorrect hybridizations. This insight also means that "capping" steps will not be necessary.

Masking technology will allow several addresses to be built up simultaneously, as is explained below. As direct consequences of the manufacturing process for the arrays, several further advantages are noted. Each 24-mer address differs from its nearest 24-mer neighbor by three tetramers, or at least 6 bases. At low salt, each base mismatch in PNA/DNA hybrids decreases the melting temperature by 8° C. Thus, the $T_m$ for the correct PNA/DNA hybridization is at least 48° C. higher than any incorrect hybridization. Also, neighboring 24-mers are separated by 12-mers, which do not hybridize with anything and represent "dead" zones in the detection profile. PNA addresses yield rugged, reusable arrays.

The following description discloses the preparation of 36 unique PNA tetramers and shows the mechanical/chemical strategy to prepare the arrays. This technique can be used to create a 5×5 array with 25 addresses of PNA 24-mers. Alternatively, all 36 tetramers can be incorporated to generate full-size arrays of 1,296 addresses.

FIGS. 18A–G are schematic diagrams showing addition of PNA tetramers to generate a 5×5 array of unique 24 mer addresses. The manufacturing device is able to add PNA tetramers in either columns, or in rows, by rotating the multi-chamber device or surface 90°. A circular manifold allows circular permutation of tetramer addition. Thus, complex unique addresses may be built by using a simple algorithm. In the first tetramer addition, PNA tetramers 1, 2, 3, 4, and 5 are linked to the surface in each of the 5 columns, respectively as shown in FIG. 18A. After rotating the chamber 90°, PNA tetramers 6, 5, 4, 3, and 2 are added in adjacent rows, as shown in FIG. 18B. In the third step, as shown in FIG. 18C, tetramers 3, 4, 5, 6, and 1 (note circular permutation) are added in columns. In the 4th step, as shown in FIG. 18D, tetramers 2, 1, 6, 5, and 4 are added in adjacent rows, etc. This process continues in the manner shown in FIG. 23E–G described infra. The bottom of the diagram depicts tetramer sequences which generate unique 24 mers at each position. The middle row of sequences 1-4-3-6-6-1; 2-4-4-6-1-1; 3-4-5-6-2-1; 4-4-6-6-3 and 5-4-1-6-4-1 are shown in full length in Table 2. The addition of tetramers in a circularly permuted fashion can be used to generate larger arrays. Tetramer addition need not be limited to circular patterns and can be added in many other combinations to form unique addresses which differ from each other by at least 3 tetramers, which translates to at least 6 bases.

The present invention has greater specificity than existing mutation detection methods which use allele-specific PCR, differential hybridization, or sequencing-by-hybridization. These methods rely on hybridization alone to distinguish single-base differences in two otherwise identical oligonucleotides. The signal-to-noise ratios for such hybridization are markedly lower than those that can be achieved even with the two most closely-related capture oligonucleotides in an array. Since each address is designed by alternating tetramer addition in three rows and three columns, a given address will differ by at least three tetramers from its neighbor. Since each tetramer differs from every other tetramer by at least 2 bases, a given address will differ from another address by at least 6 bases. However, in practice, most addresses will differ from most other addresses by considerably more bases.

This concept is illustrated below using the two addresses, Zip 12 and Zip 14. These two addresses are the most related among the 25 addresses schematically represented in FIGS. 18 and 20 (discussed infra). These two addresses have in common tetramers on every alternating position (shown as underlined):

Zip 12 (2-4-4-6-1-1)=24 mer
5'- ATCG GGTA GGTA ACCT TGCG TGCG-3' (SEQ. ID. No. 6)
Zip 14 (4-4-6-6-3-1)=24 mer
5'- GGTA GGTA ACCT ACCT CAGC TGCG-3' (SEQ. ID. No. 7)

In addition, they have in common a string of 12 nucleotides, as well as the last four in common (shown as underlined):

Zip 12 (2-4-4-6-1-1)=24 mer
5'-ATCG GGTA GGTA ACCT TGCG TGCG-3' (SEQ. ID. No. 8)
Zip 14 (4-4-6-6-3-1)=24 mer
5'-GGTA GGTA ACCT ACCT CAGC TGCG-3' (SEQ. ID. No. 9)

Either representation has at least 8 differences between the oligonucleotides. Although an oligonucleotide complementary to Zip 12 or Zip 14 at the underlined nucleotides could hybridize to both of these addresses at a lower temperature (e.g., 37° C.), only the fully complementary oligonucleotide would hybridize at elevated temperature (e.g., 70° C.).

Furthermore, for other capture oligonucleotides, such as Zip 3, the number of shared nucleotides is much lower (shown as underlined):

Zip 12 (2-4-4-6-1-1)=24 mer
5'- ATCG GGTA GGTA ACCT TGCG TGCG-3' (SEQ. ID. No. 10)
Zip 3 (3-6-5-2-2-3)=24 mer
5'- CAGC ACCT GACC ATCG ATCG CAGC-3' (SEQ. ID. No. 11)

Therefore, the ability to discriminate Zip 12 from Zip 3 during hybridization is significantly greater than can be achieved using any of the existing methods.

Figure 19A:
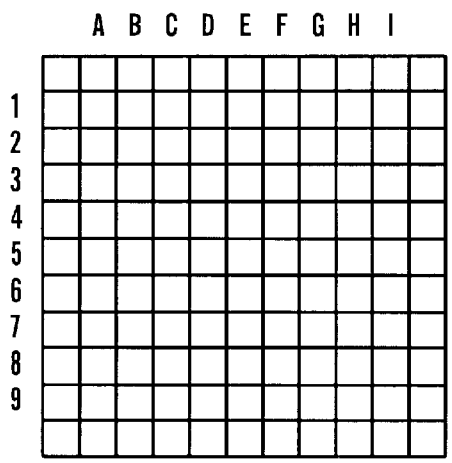
FIGS. 19A–E depict a protocol for constructing an 8×8 array of 24-mers by sequentially coupling 6 tetramers.
Figure 19B:
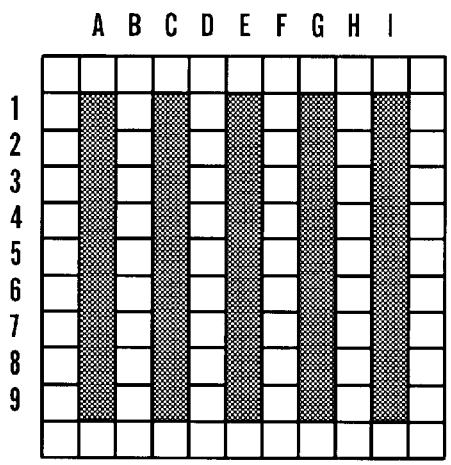
Figure 19C:
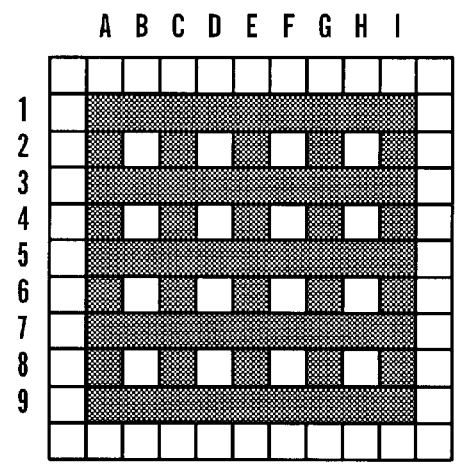

A multi-chamber device with alternating chambers and walls (each 200 μm thick) will be pressed onto the modified glass or silicon surface of FIG. 19A prior to delivery of PNA tetramers into either columns or rows. The surface will be etched to produce 10 μm ridges (black lines) to eliminate leaking between chambers. Initially, a flexible spacer (linker) is attached to the array surface. In the first step, as shown in FIG. 19B, PNA tetramers, 1, 2, 3, 4, and 5 are linked to the surface in each of the five columns, respectively. The multi-chamber device is then rotated 90°. Tetramers 6, 5, 4, 3, and 2 are added in adjacent rows, as shown in FIG. 19C. The process is repeated a total of three times to synthesize 24-mer PNA oligomers. Each completed 24-mer within a given row and column represents a unique PNA sequence, hence achieving the desired addressable array. Smaller oligonucleotide sequences represent half-size 12-mers which result from 3 rounds of synthesis in the same direction. Since each 24-mer differs from its neighbor by three tetramers and each tetramer differs from another by at least 2 bases, then each 24-mer differs from the next by at least 6 bases (i.e., 25% of the nucleotides differ). Thus, a wrong address would have 6 mismatches in just 24 bases and, therefore, would not be captured at the wrong address, especially under 75-80° C. hybridization conditions. In addition, while a particular smaller 12-mer sequence may be found within a 24-mer sequence elsewhere on the grid, an addressable array-specific portion will not hybridize to the 12-mer sequence at temperatures above 50° C.

The starting surfaces will contain free amino groups, a non-cleavable amide linkage will connect the C-terminus of PNA to the support, and orthogonal side-chain deprotection must be carried out upon completion of segment condensation assembly in a way that PNA chains are retained at their addresses. A simple masking device has been designed that contains 200 μm spaces and 200 μm barriers, to allow each of 5 tetramers to couple to the solid support in distinct rows (FIG. 20A). After addition of the first set of tetramers, the masking device is rotated 90°, and a second set of 5 tetramers are added (FIG. 20B). This can be compared to putting icing on a cake as rows, followed by icing as columns. The intersections between the rows and columns will contain more icing, likewise, each intersection will contain an octamer of unique sequence. Repeating this procedure for a total of 6 cycles generates 25 squares containing unique 24-mers, and the remaining squares containing common 12-mers (FIGS. 20C and 21A–F). The silicon or glass surface will contain 10 μm ridges to assure a tight seal, and chambers will be filled under vacuum. A circular manifold (FIG. 26) will allow for circular permutation of the six tetramers prior to delivery into the five rows (or columns). This design generates unique 24-mers which always differ from each other by at least 3 tetramers, even though some sequences contain the same 3 tetramers in a contiguous sequence. This masking device is conceptually similar to the masking technique disclosed in Southern, et al., *Genomics*, 13:1008–1017 (1992) and Maskos, et al., *Nucleic Acids Res.*, 21:2267–2268 (1993), which are hereby incorporated by reference, with the exception that the array is built with tetramers as opposed to monomers.

Figure 19D:
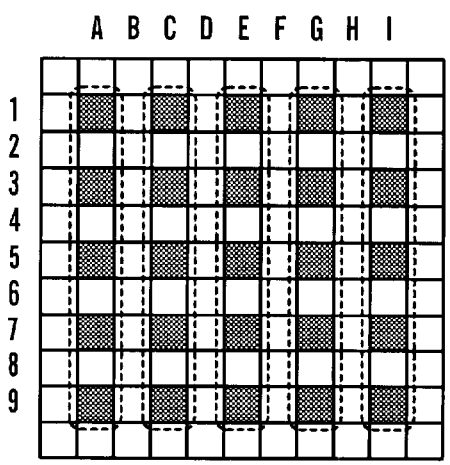
Figure 19E:
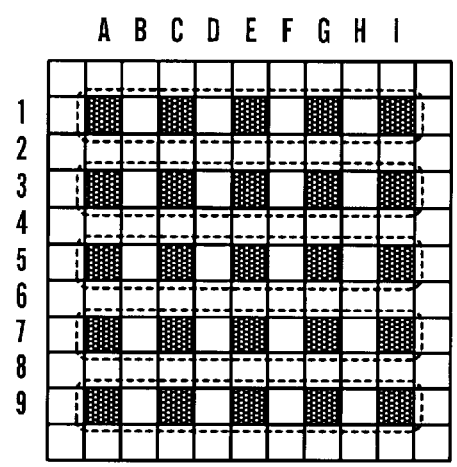

Alternatively, the production of the incomplete 12-mer sequences can be eliminated if a mask which isolates each location is used. In the first step (as shown in FIG. 19D), PNA tetramers 1, 2, 3, 4, and 5 are linked to the surface in each of the five columns respectively. The multi-chamber device is then rotated 90°. Tetramers 6, 5, 4, 3, and 2 are added in adjacent rows, as shown in FIG. 19E. The process is repeated a total of three times to synthesize 24-mer PNA oligomers. Each completed 24-mer within a given row and column represents a unique PNA sequence, hence achieving the desired addressable array. In addition, each 24-mer will be separated from adjacent oligomers by a 200 μm region free of PNA oligomers.

A silicon or glass surface will be photochemically etched to produce a crosshatched grid of 10 μm raised ridges in a checkerboard pattern (see FIG. 20). Alternate squares (200 μm×200 μm) will be activated, allowing for the attachment of $C_{18}$ alkyl spacers and PEG hydrophilic linkers (MW 400–4,000), such that each square is separated by at least one blank square and two ridges on all sides.

An example of a universal array using PNA tetramers can be formed by adding 36 different tetramers to either 36 columns or rows at the same time. The simplest way to add any tetramer to any row is to have all 36 tetramer solutions attached by tubings to minivalves to a circular manifold which has only one opening. The other side of the circular manifold can be attached to any of 36 minivalves which go to individual rows (or columns). So by rotating the manifold and minivalves to the chambers (rows), one can pump any tetramer into any row, one at a time. This can be either a mechanical device requiring physical rotation or, alternatively, can be accomplished by using electronic microvalves along a series of import (tetramers) and export (rows) channels. This process can occur quite rapidly (5 seconds, including rinsing out the manifold for its next use), so that it would take about 36×5=180 sec. to add all 36 rows.

A potentially more rapid way of filling the rows or columns, would be to fill all of them simultaneously. This is illustrated in FIG. 20 for a 5×5 array. The silicon or glass surface will contain 10 μm ridges to assure a tight seal, and chambers will be filled using the vacuum technique described above. A circular manifold will allow for circular permutation of the six tetramers prior to delivery into the five rows (or columns). In FIG. 20, the first step is 5, 4, 3, 2, 1. When rotating the multi-chamber device, one could continue to add in either numerical, or reverse numerical order. In the example, a numerical order of 2, 3, 4, 5, 6 for the second step is used. In the third step, the circular permutation (reverse) gives 1, 6, 5, 4, 3. Fourth step (forward) 4, 5, 6, 1, 2. Fifth step (reverse) 4, 3, 2, 1, 6. Sixth step (forward) 5, 6, 1, 2, 3. This can be expanded to 36 tetramers into 36 rows (or columns). This approach limits the potential variations in making the address for the array from $36^6=2,176,782,336$ in every position to $36^6=2,176,782,336$ in one position, with the other 1,295 positions now defined by the first address. This is still a vast excess of the number of different addresses needed. Furthermore, each address will still differ from every other address by at least 6 nucleotides.

Note that all of these arrays can be manufactured in groups, just as several silicon chips can be produced on the same wafer. This is especially true of the tetramer concept, because this requires adding the same tetramer in a given row or column. Thus, one row could cover a line of ten arrays, so that a 10×10 grid=100 arrays could be manufactured at one time.

Alternatively, the process described with reference to FIG. 20 can be carried out with one less cycle to make a 20 mer oligonucleotide. The capture oligonucleotide should be sufficiently long to capture its complementary addressable array-specific portion under the selected hybridization conditions.

Figure 21A:
FIGS. 21A–F show a schematic cross-sectional view of the synthesis of an addressable array, in accordance with FIGS. 19B–C.
Figure 21B:
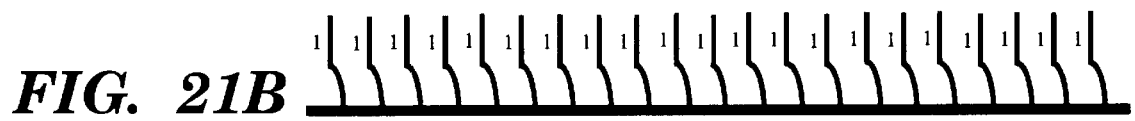
Figure 21C:
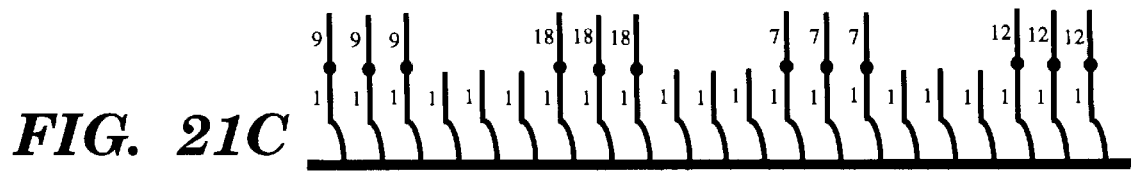
Figure 21D:
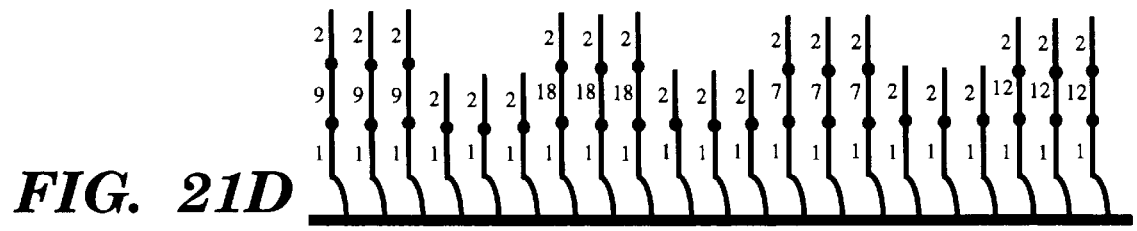
Figure 21E:
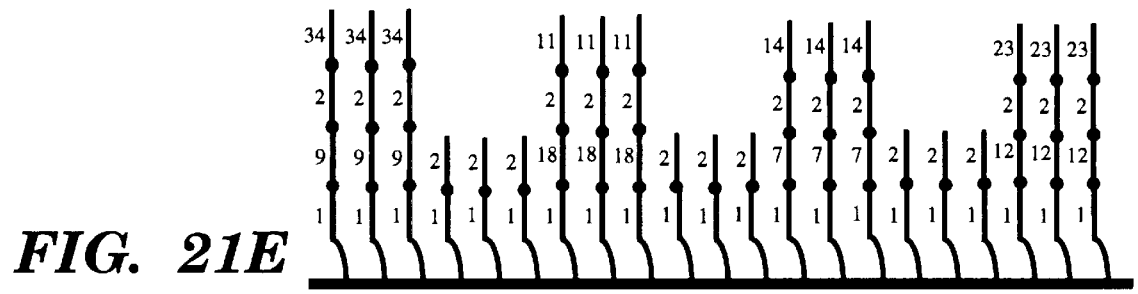
Figure 21F:
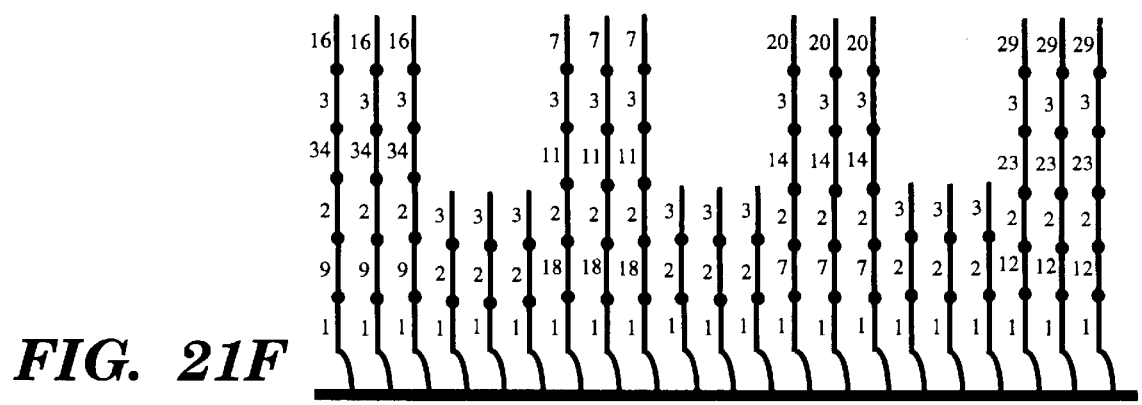

FIGS. 21A–F show a schematic cross-sectional view of the synthesis of an addressable array (legend). FIG. 21A shows attachment of a flexible spacer (linker) to surface of array. FIG. 21B shows the synthesis of the first rows of oligonucleotide tetramers. Only the first row, containing tetramer 1, is visible. A multi-chamber device is placed so that additional rows, each containing a different tetramer, are behind the first row. FIG. 21C shows the synthesis of the first columns of oligonucleotide tetramers. The multi-chamber device or surface has been rotated 90°. Tetramers 9, 18, 7, and 12 were added in adjacent chambers. FIG. 21D shows the second round synthesis of the oligonucleotide rows. The first row contains tetramer 2. FIG. 21E shows the second round of synthesis of oligonucleotides. Tetramers 34, 11, 14, and 23 are added in adjacent chambers during the second round. FIG. 21F shows the third round synthesis of PNA rows. The first row contains tetramer 3 to which tetramers 16, 7, 20, and 29 and are added. Note that all 24-mer oligonucleotides within a given row or column are unique, hence achieving the desired addressable array. Since each 24-mer differs from its neighbor by three tetramers, and tetramers differ from each other by at least 2 bases, then each 24-mer differs from the next by at least 6 bases. Each mismatch significantly lowers $T_m$, and the presence of 6 mismatches in just 24 bases would make cross hybridization unlikely even at 35° C. Note that the smaller 12-mer sequences are identical with one another, but are not at all common with the 24-mer sequences. Even though the particular 12-mer sequence may be found within a 24-mer elsewhere on the grid, for example 17-1-2-3-28-5, an oligonucleotide will not hybridize to the 12-mer at temperatures above 50° C.

FIGS. 22A-C present a design for a masking device 2 capable of constructing an array grid G as described in FIGS. 19–21. FIG. 22A is a top view of the arrangement of device 2 and array grid G, while side views FIGS. 22B–22C are, respectively, taken along line 22B–22B and line 22C–22C of FIG. 22A. The masking device contains 200 μm spaces and 200 μm barriers, to allow each of five tetramers to be coupled to the solid support in distinct rows. After addition of the first set of tetramers, the masking device is rotated 90°, and a second set of 5 tetramers are added. This can be compared to putting icing on a cake as rows, followed by icing as columns. The intersections between the rows and columns will contain more icing, likewise, each intersection will contain an octamer of unique sequence. Repeating this procedure for a total of 6 cycles generates 25 spatially separated squares containing unique 24-mers, and the remaining squares containing common 12-mers. The silicon or glass surface will contain 10 μm ridges R to assure a tight seal, and chambers 4 will be filled by opening valves 8 to a vacuum line 12 to create negative pressure in the chamber. The multi-chamber device is pressed onto the membrane or activated solid surface, forming tight seals. The barriers may be coated with rubber or another material to avoid cross contamination from one chamber to the next. One must also make sure the membrane or support surface is properly wetted by the solvents. After closing valves 8 to vacuum line 12, one proceeds by activating the surface, deprotecting, and adding a tetramer to a chamber 4 through lines 10 by opening valves 6. The chamber is unclamped, the membrane is rotated 90°, and reclamped. A second round of tetramers are added by the above-described vacuum and tetramer application steps. A valve block assembly (FIG. 25A–C) will route each tetramer to the appropriate row. Alternatively, a cylindrical manifold (FIGS. 26A–D) will allow circular permutation of the six tetramers prior to delivery into the five rows (or columns). This design generates unique 24-mers which always differ from each other by at least 3 tetramers, even though some sequences contain the same 3 tetramers in a contiguous sequence.

FIGS. 23A–C represent a perspective view of the array construction process described in FIG. 19 (FIGS. 19D–19E). In the first step, as shown in FIG. 23A, PNA tetramers 1, 2, 3, 4, and 5 are linked to the surface in each of the five columns, respectively. Each of the 5 locations in the columns are isolated, and there is a 200 μm gap between them where no oligonucleotides are coupled. The multi-chamber device is then rotated 90°, as shown in FIG. 23B. Tetramers 6, 5, 4, 3, and 2 are added in adjacent rows. Each of the 5 locations in the rows are isolated, and there is a 200 μm gap between them where no oligonucleotides are coupled. Each completed 24-mer, as shown in FIG. 23C, within a given row and column represents a unique PNA sequence. Unlike the design presented in FIGS. 19–22, this array design will not contain the half-size 12-mers between each complete 24-mer, because a mask with isolated locations will be used.

FIGS. 24A–C present a design for a masking device 2 capable of constructing an array grid G as described in FIG. 23. FIG. 24A is a top view of the arrangement of device 2 and array grid G, while side views FIG. 24B and 24C are, respectively, taken along line 24B–24B and line 24C–24C of FIG. 24A. The masking device contains 200 μm spaces and 200 μm barriers, to allow each of five tetramers to be coupled to the solid support in distinct locations on the array grid G. After addition of the first set of tetramers, the masking device or surface is rotated 90°, and a second set of 5 tetramers are added. Repeating this procedure for a total of 6 cycles generates 25 spatially separated squares containing unique 24-mers, and the remaining squares containing common 12-mers. The silicon or glass surface will contain 10 μm ridges R to assure a tight seal, and chambers 4 will be filled by a procedure initiated by using a vacuum to create negative pressure in the chamber 2. This vacuum is created by opening valves 8 to vacuum line 12. The multi-chamber device is pressed onto the membrane or activated solid surface, forming tight seals. The barriers may be coated with rubber or another material to avoid cross contamination from one chamber to the next. One must also make sure the membrane or solid support surface is properly wetted by the solvents. After closing valves 8 to vacuum line 12, one proceeds by activating the surface, deprotecting, and adding a tetramer to chamber 4 through lines 10 by opening valves 6. The chamber is unclamped, the membrane is rotated 90°, and reclamped. A second round of tetramers are added by the above-described vacuum and tetramer application steps. A valve block assembly (FIG. 25A–C) will route each tetramer to the appropriate row. Alternatively, a cylindrical manifold (FIG. 26A–D) will allow circular permutation of the six tetramers prior to delivery into the five rows (or columns). This design generates unique 24-mers which are separated from each other by a region free of any oligonucleotides.

FIGS. 25A–C show a valve block assembly 14 which connects six input ports 10 to five output ports 16 via a common chamber 18. Each of the 6 input ports 10 and 5 output ports 16 contains a valve 6 and a valve 20, respectively, which control the flow of fluids. The 6 input tubes 10 contain different solutions, and the valve block assembly 14 is capable of routing any one of the input fluids to one of the 5 output ports 16 at a time. This is accomplished by opening the valve 6 of one of the input ports 10 and one of the valves 20 of the output ports 16 simultaneously and allowing fluid to fill the chamber 18 and exit via the output port 16 connected to the open valve 20. The valve block assembly 14 is connected to a source of solvent 22 and a source of vacuum 12 via valves 24 and 8, respectively, in order to allow cleaning of the central chamber 18 in between fluid transfers. The solvent fills the chamber 18, and the vacuum is used to remove all fluid from the chamber. This prepares the chamber 18 for the next fluid transfer step and prevents cross-contamination of the fluids.

FIGS. 26A–D depict a cylindrical manifold assembly 114 which transfers 6 different tubes of input fluids to 5 different output tubes. The manifold itself contains two separate halves 114A and 114B which are joined by a common, central spoke 134 around which both halves can independently rotate. The bottom portion 114B is a cylindrical block with 6 channels 130 drilled through it (see FIG. 26C, which is a bottom view of FIG. 26B taken along line 26C—26C of FIG. 26B). Each of the 6 channels 130 are attached to 6 different input tubes 110. The input tubes 110 contain valves 106 which connect the input channels 130 to either reagents, solvent, or a vacuum via lines 138 having valves 136 leading to vacuum line 112 having valve 108 and solvent line 122 having valve 124. This allows different fluids to enter the channels 130 and 132 of the manifold and allows clearing of the channels 130 and 132 of excess fluid between fluid transfers. The upper portion of the manifold (see FIG. 26A, which is a top view of FIG. 26B taken along line 26A–26A of FIG. 26B) is also a cylindrical block with 5 channels 132 drilled through it. The 5 channels 132 are each connected to a different output tube 116. The two halves of manifold 114A and 114B can be independently rotated so that different input channels 130 will line up with different output channels 132. This allows the 6 tubes of input fluids to be transferred to the 5 output tubes simultaneously. The bottom half of the manifold 114B can be rotated 60 degrees in order to align each input port 110 with the next output port 116. In this way, each input port 110 can be aligned with any of the output ports 116. The circular manifold of FIGS. 26A–D differs from the valve block assembly of FIGS. 26A–C in that the former can simultaneously transfer five of the six input fluids to the five output ports, because it has 5 channels connecting input ports to the output ports. This concept could be easily expanded to deliver 36 tetramers simultaneously to 36 locations.

The present invention contains a number of advantages over prior art systems.

The solid support containing DNA arrays, in accordance with the present invention, detects sequences by hybridization of ligated product sequences to specific locations on the array so that the position of the signal emanating from captured labels identifies the presence of the sequence. For high throughput detection of specific multiplexed LDR products, addressable array-specific portions guide each LDR product to a designated address on the solid support. While other DNA chip approaches try to distinguish closely related sequences by subtle differences in melting temperatures during solution-to-surface hybridization, the present invention achieves the required specificity prior to hybridization in solution-based LDR reactions. Thus, the present invention allows for the design of arrays of capture oligonucleotides with sequences which are very different from each other. Each LDR product will have a unique addressable array-specific portion, which is captured selectively by a capture oligonucleotide at a specific address on the solid support. When the complementary capture oligonucleotides on the solid support are either modified DNA or PNA, LDR products can be captured at higher temperatures. This provides the added advantages of shorter hybridization times and reduced non-specific binding. As a result, there is improved signal-to-noise ratios.

Another advantage of the present invention is that PCR/LDR allows detection of closely-clustered mutations, single-base changes, and short repeats and deletions. These are not amenable to detection by allele-specific PCR or hybridization.

In accordance with the present invention, false hybridization signals from DNA synthesis errors are avoided. Addresses can be designed so there are very large differences in hybridization $T_m$ values to incorrect address. In contrast, the direct hybridization approaches depend on subtle differences. The present invention also eliminates problems of false data interpretation with gel electrophoresis or capillary electrophoresis resulting from either DNA synthesis errors, band broadening, or false band migration.

The use of a capture oligonucleotide to detect the presence of ligation products, eliminates the need to detect single-base differences in oligonucleotides using differential hybridization. Other existing methods in the prior art relying on allele-specific PCR, differential hybridization, or sequencing-by-hybridization methods must have hybridization conditions optimized individually for each new sequence being analyzed. When attempting to detect multiple mutations simultaneously, it becomes difficult or impossible to optimize hybridization conditions. In contrast, the present invention is a general method for high specificity detection of correct signal, independent of the target sequence, and under uniform hybridization conditions. The present invention yields a flexible method for discriminating between different oligonucleotide sequences with significantly greater fidelity than by any methods currently available within the prior art.

The array of the present invention will be universal, making it useful for detection of cancer mutations, inherited (germline) mutations, and infectious diseases. Further benefit is obtained from being able to reuse the array, lowering the cost per sample.

The present invention also affords great flexibility in the synthesis of oligonucleotides and their attachment to supports. Oligonucleotides can be synthesized off of the support and then attached to unique surfaces on the support. Segments of multimers of oligonucleotides, which do not require intermediate backbone protection (e.g., PNA), can be synthesized and linked onto to the solid support. Added benefit is achieved by being able to integrate these synthetic approaches with design of the capture oligonucleotide addresses. Such production of solid supports is amenable to automated manufacture, obviating the need for human intervention and resulting contamination concerns.

An important advantage of the array of the present invention is the ability to reuse it with the previously attached capture oligonucleotides. In order to prepare the solid support for such reuse, the captured oligonucleotides must be removed without removing the linking components connecting the captured oligonucleotides to the solid support. A variety of procedures can be used to achieve this objective. For example, the solid support can be treated in distilled water at 95–100° C., subjected to 0.01 N NaOH at room temperature, contacted with 50% dimethylformamide at 90–95° C., or treated with 50% formamide at 90–95° C. Generally, this procedure can be used to remove captured oligonucleotides in about 5 minutes. These conditions are suitable for disrupting DNA-DNA hybridizations; DNA-PNA hybridizations require other disrupting conditions.

The present invention is illustrated, but not limited, by the following examples.

EXAMPLES

Example 1

Immobilization of Capture Oligonucleotides to Solid Supports

The solid support for immobilization was glass, in particular microscope slides. The immobilization to glass (e.g., microscope slides), or other supports such as silicon (e.g., chips), membranes (e.g., nylon membranes), beads (e.g., paramagnetic or agarose beads), or plastics supports (e.g., polyethylene sheets) of capture oligonucleotides in spatially addressable arrays is comprised of 5 steps:

A. Silanization of support

The silanization reagent was 3-aminopropyl triethoxysilane ("APTS"). Alternatively, 3-glycidoxypropyltrimethoxysilane (K. L. Beattie, et al., "Advances in Genosensor Research," *Clin. Chem.,* 41:700–706 (1995); U. Maskos, et al., "Oligonucleotide Hybridizations on Glass Supports: a Novel Linker for Oligonucleotide Synthesis and Hybridization Properties of Oligonucleotides Synthesized in situ," *Nucleic Acids Res.,* 20:1679–1684 (1992); C. F. Mandenius, et al., "Coupling of Biomolecules to Silicon Surfaces for Use in Ellipsometry and Other Related Techniques," *Methods Enzymol., pp.* 388–394 (1988), which are hereby incorporated by reference) or 3-(trimethoxysilyl)propyl methacrylate (M. Glad, et al., "Use of Silane Monomers for Molecular Imprinting and Enzyme Entrapment in Polysiloxane-coated Porous Silica," *J. Chromatogr.* 347:11–23 (1985); E. Hedborg, et al., "Some Studies of Molecularly-imprinted Polymer Membranes in Combination with Field-effect Devices," *Sensors and Actuators A* 37–38:796–799 (1993); and M. Kempe, et al., "An Approach Towards Surface Imprinting Using the Enzyme Ribonuclease A," *J. Mol. Recogn.* 8:35–39 (1995), which are hereby incorporated by reference) can be used as an initial silanization reagent. Prior to silanization, the support was cleansed and the surface of the support was rendered hydrophobic. Glass slides (Fisher Scientific, Extra thick microslides, frosted cat.# 12-550-11) were incubated in conc. aq. $NH_4OH$—$H_2O_2$-$H_2O$ (1:1:5, v/v/v) at 80° C. for 5 min and rinsed in distilled water. The support was then washed with distilled water, ethanol and acetone as described in the literature (C. F. Mandenius, et al., "Coupling of Biomolecules to Silicon Surfaces for Use in Ellipsometry and Other Related Techniques," *Methods Enzymol., pp.* 388–394 (1988); Graham, et al., "Gene Probe Assays on a Fibre-Optic Evanescent Wave Biosensor," *Biosensors & Bioelectronics,* 7: 487–493 (1992); Jönsson, et al., "Adsorption Behavior of Fibronectin on Well Characterized Silica Surfaces," *J. Colloid Interface Sci.,* 90:148–163 (1982), which are hereby incorporated by reference). The support was silanized overnight at room temperature in a solution of 2% (v/v) 3-aminopropyl triethoxysilane (Sigma, St. Louis, Mo.) in dry acetone (99.7%) (modified after Z. Guo, et. al., "Direct Fluorescence Analysis of Genetic Polymorphisms by Hybridization with Oligonucleotide Arrays on Glass Supports," *Nucl. Acids Res.* 22:5456–65 (1994), which is hereby incorporated by reference). The support was then thoroughly washed in dry acetone and dried at 80° C. in a vacuum desiccator.

B. Derivatization of silanized solid support with functional groups (e.g., carboxyl or amino groups)

When the silanization reagent was APTS, the desired amino functionality was introduced directly. Other functional groups can be introduced, either by choosing an appropriate silanization reagent primer that already contains the functional group (e.g., 3-(trimethoxysilyl)propyl methacrylate to functionalize the surface with a polymerizable acrylate, (M. Glad, et al., "Use of Silane Monomers Imprinting and Enzyme Entrapment in Polysiloxane-coated Porous Silica," *J. Chromatogr.* 347:11–23 (1985); E. Hedborg, et al., "Some Studies of Molecularly-imprinted Polymer Membranes in Combination with Field-effect Devices," *Sensors and Actuators A* 37–38:796–799 (1993); and M. Kempe, et al., "An Approach Towards Surface Imprinting Using the Enzyme Ribonuclease A," *J. Mol. Recogn.* 8:35–39 (1995), which are hereby incorporated by reference), or by reacting the amino-functionalized surface with a reagent that contains the desired functional group (e.g., after localized light-directed photodeprotection of protected amino groups used in photolithography, (Fodor, et al., "Light-Directed, Spatially Addressable Parallel Chemical Synthesis," *Science,* 251:767–773 (1991); Fodor, et al., "Multiplexed Biochemical Assays with Biological Chips," *Nature,* 364:555–556 (1993), which are hereby incorporated by reference)).

C. Activation of functional groups

The functional group on the solid support was an amino group. Using a prefabricated mask with a 5×5 array of dots that have a diameter of 1 mm, and that are 3.25 mm apart, small amounts (typically 0.2 to 1.0 μl) of a solution containing 70 mg/ml disuccinimidyl adipate ester (Hill, et al., "Disuccinimidyl Esters as Bifunctional Crosslinking Reagents for Proteins," *FEBS Lett,* 102:282–286 (1979); Horton, et al., "Covalent Immobilization of Proteins by Techniques which Permit Subsequent Release," *Methods Enzmol., pp.*130–141(1987), which are hereby incorporated by reference) in anhydrous dimethylformamide ("DMF"); Aldrich, Milwaukee, Wis.), amended with 1-2% triethylamine (to scavenge the acid that is generated), were manually applied to the solid support using a Gilson P-10 pipette. After application, the reaction was allowed to proceed for 30 min at room temperature in a hood, after which another loading of disuccinimidyl adipate ester was applied. After a total reaction time of 1 hour, the support was washed with anhydrous DMF and dried at room temperature in a vacuum desiccator.

In case the functional group is a carboxyl group, the solid support can be reacted with 1-ethyl-3-(3-dimethylaminopropyl) carbodiimide hydrochloride ("EDC"). Frank, et al., "Simultaneous Multiple Peptide Synthesis Under Continuous Flow Conditions on Cellulose Paper Discs as Segmental Solid Support," *Tetrahedron*, 44:6031–6040 (1988), which is hereby incorporated by reference. Prior to this reaction, the surface of the solid support was protonated by a brief treatment with 0.1 N HCl. Using the above described prefabricated mask, small amounts (0.2 to 1.0 μl) of a fresh solution containing 1 M EDC (Sigma, St. Louis, Mo.), 1 mM of 5' amino-modified oligonucleotide and 20 mM $KH_2PO_4$, pH=8.3, was manually applied to the solid support. The reaction was allowed to proceed for 1 hour, after which the support was washed with distilled water and dried at room temperature in a vacuum desiccator.

D. Coupling of amino-functionalized capture oligonucleotides to the preactivated solid support For supports other than EDC-activated solid supports, small amounts (0.2 to 1.0 μl) of 1 nmol/μl 5' amino-modified oligonucleotides (i.e. the sequences in Table 2) in 20 mM $KH_2PO_4$, pH 8.3, were manually applied to the activated support, again using the prefabricated mask described above. The reaction was allowed to proceed for 1 hour at room temperature.

E. Quenching of remaining reactive groups on the solid support

In order to prevent the reaction products from being nonspecifically captured on the solid support in a capture probe-independent way, it may be necessary to quench any remaining reactive groups on the surface of the solid support after capture of the complementary oligonucleotide probes. Hereto, the support was incubated for 5 min at room temperature in 0.1 N sodium hydroxide. Alternatively, quenching can be performed in 0.2 M lysine, pH=9.0. After quenching, the support was washed with 0.1 N sodium phosphate buffer, pH 7.2, to neutralize the surface of the support. After a final wash in distilled water, the support was dried and stored at room temperature in a vacuum desiccator.

Example 2
Design of the Assay System

Figure 27:
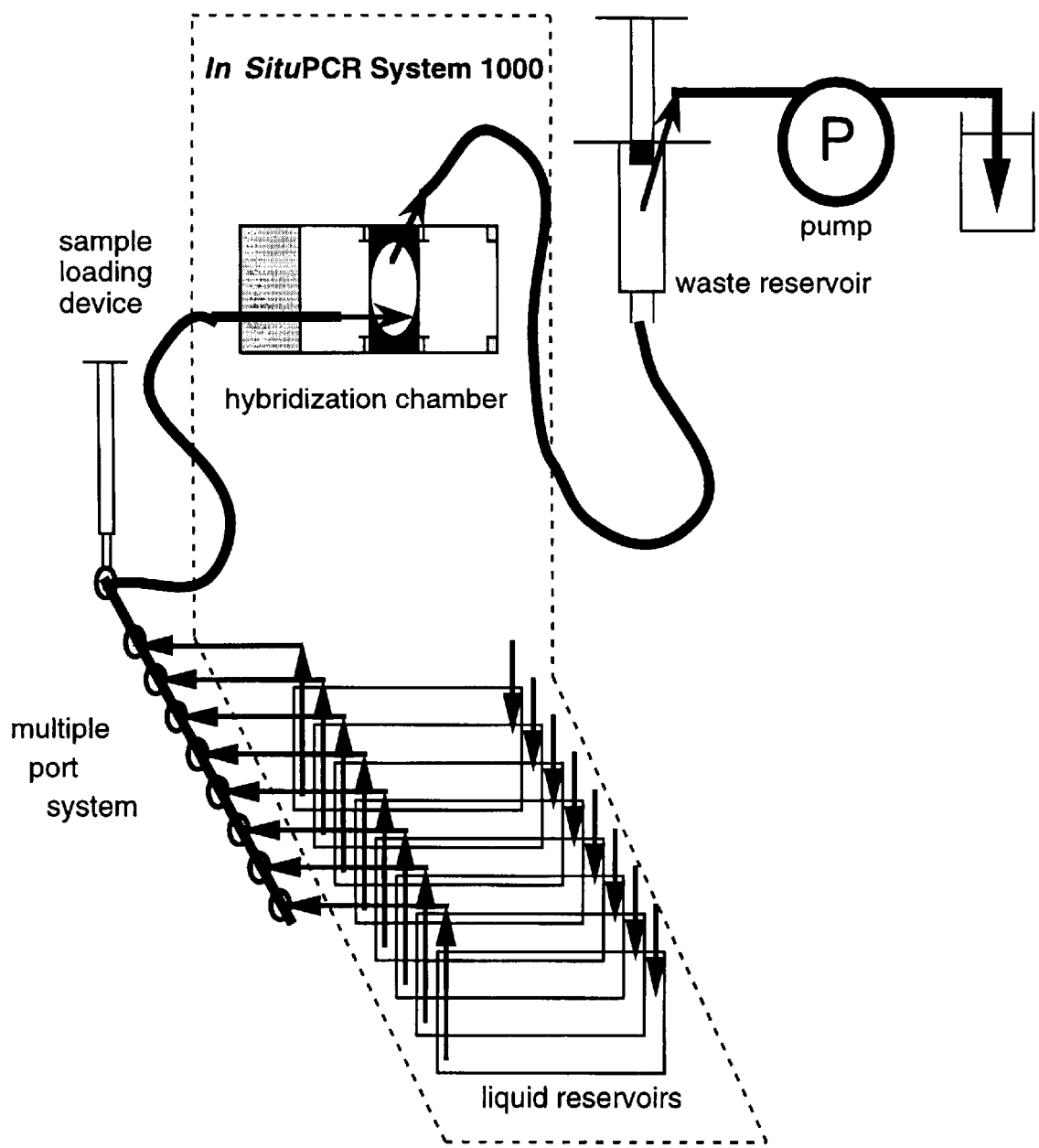
FIG. 27 is a schematic drawing of an assay system for carrying out the process of the present invention.

A semi-automated custom-designed assay system was made for testing hybridizations and subsequent washings of captured oligonucleotide probe-capture oligonucleotide hybrids in a high-throughput format using the GeneAmp In Situ PCR System 1000™ (Perkin Elmer, Applied Biosystems Division, Foster City, Calif.) (G. J. Nuovo, *PCR in situ Hybridization*, New York: Raven Press (2nd ed. 1994), which is hereby incorporated by reference). A general flowchart of the system is shown in FIG. 27. The system consists of a flow-through hybridization chamber which is connected via a sample loading device and a multiple port system to a battery of liquid reservoirs, and to a waste reservoir. The fluid delivery is controlled by a pump. The pump was placed at the end of the assembly line and operated under conditions to maintain a light vacuum to prevent leakage and contamination of the system. Since the hybridization chamber and the liquid reservoirs were designed to fit precisely within the GeneAmp In Situ PCR System 1000™, temperatures can be accurately controlled and maintained during the hybridization and washing steps of the assay.

The individual parts of the system are described in detail in the following section:

A. Hybridization chamber

The hybridization chamber is an in situ PCR reagent containment system that has been modified to accommodate flow-through characteristics. The containment system is comprised of a glass microscope slide (76×25×1.2±0.02 mm) and a silicone rubber diaphragm, which has been clamped to the slide by a thin stainless steel clip. The inside oval rim of the metal clip compresses the edges of the silicon disc against the slide with enough force to create a water and gas-tight seal ensuring the containment of hybridization probes and washing liquids. The volume of the containment is approximately 50 μl. The array of immobilized capture oligonucleotides is contained in the central area of the slide (approximately 13 mm×15 mm) which is covered by the silicon disc. The assembly of the different parts is facilitated by an assembly tool which is provided by the manufacturer of the in situ PCR system. Once assembled, an inlet and outlet of the hybridization chamber is created by insertion of two 25G3/4 needles with 12" tubing and multiple sample luer adapter (Becton Dickinson, Rutherford, N.J.). The needles are inserted in a diagonal manner to assure an up-and-across flow pattern during washing of the probe-target hybrids.

B. Liquid reservoirs

Reservoirs containing different washing solutions were custom-designed to fit into the vertical slots of the thermal block of the GeneAmp In Situ PCR System 1000™. Each reservoir consists of two glass microscope chamber slides (25×75×1 mm) containing prefabricated silicone gaskets (Nunc, Inc., Napierville, Ill.), which were glued to each other using silicone sealant (Dow Corning, Midland, Mich.). An outlet was created by insertion of a 21G ¾" needle with 12" long tubing and multiple sample luer adapter (Becton Dickinson, Rutherford, N.J.) through the silicone gasket. A second 21G ¾" needle without tubing (Becton Dickinson, Franklin Lakes, N.J.) was inserted through the silicone gasket to create an air inlet. The liquid reservoirs are leak-free and fit precisely within the slots of the thermal block, where they are clamped against the metal fins to assure good heat transfer to the contained liquid. The volume of each reservoir is approximately 2 ml.

C. Multi port system and sample loading device

Liquid reservoirs, sample loading device and hybridization chamber are connected through a multiple port system that enables a manually controlled unidirectional flow of liquids. The system consists of a series of 3-way nylon stopcocks with luer adapters (Kontes Scientific Glassware/Instruments, Vineland, N.J.) that are connected to each other through male-female connections. The female luer adapters from the liquid reservoirs are connected to the multi port female luer adapters via a male-to-male luer adapter coupler (Biorad, Richmond, Calif.). The sample loading device is placed in between the ports connected to the liquid reservoirs and the port connected to the hybridization chamber. It consists of a 1 ml syringe (Becton Dickinson, Franklin Lakes, N.J.) that is directly connected via a luer adapter to the multi port system. The flow of liquids can be controlled manually by turning the handles on the stopcocks in the desired direction.

D. Waste reservoir

The outlet tubing from the hybridization chamber is connected to a waste reservoir which consists of a 20 ml syringe with luer adapter (Becton Dickinson, Franklin Lakes, N.J.) in which the plunger has been secured at a fixed position. A connection to the pump is established by insertion of a 21G ¾" needle with 12" long tubing and multiple sample luer adapter through the rubber gasket of the plunger. When the pump is activated, a slight vacuum is built up in the syringe which drives the flow of liquids from the liquid reservoirs through the hybridization chamber to the waste reservoir.

E. Pump

A peristaltic pump P-1 (Pharmacia, Piscataway, N.J.) was used to control the flow of liquids through the system. It was placed at the end of the assembly line in order to maintain a slight vacuum within the system. The inlet tubing of the pump was connected to the outlet tubing of the waste reservoir via a 3-way nylon stopcock. By this construction, release of the vacuum within the waste reservoir is established, enabling its draining by gravity.

Example 3

Hybridization and Washing Conditions

In order to assess the capture specificity of different capture oligonucleotides, hybridization experiments were carried out using two capture oligonucleotide probes that had 3 out of 6 tetramers (i.e., 12 out of 24 nucleotides) in common. This example represents the most difficult case to distinguish between different capture oligonucleotides. In general, other capture oligonucleotides would be selected that would have fewer tetramers in common to separate different amplification products on an addressable array.

Typically, 10 pmol of each of the oligonucleotides comp 12 and comp 14 (see Table 3) were 5' end labeled in a volume of 20 µl containing 10 units of T4 polynucleotide kinase (New England Biolabs, Beverly, Mass.), 2.22 MBq (60 µCi) [γ-$^{32}$P] ATP, 50 mM Tris-HCl, pH 8, 10 mM MgCl$_2$, 1 mM EDTA, and 10 mM dithiothreitol, according to a slightly modified standard procedure described in the literature. Unincorporated radioactive nucleotides were removed by filtration over a column containing superfine DNA grade Sephadex G-25 (Pharmacia, Piscataway, N.J.). The Sephadex was preswollen overnight at 4° C. in 10 mM ammonium acetate. The labeled oligonucleotide probes were dried in vacuum and dissolved in hybridization solution (0.5 M Na$_2$HPO$_4$ [pH 7.2], 1% crystalline grade BSA, 1 mM EDTA, 7% SDS). The specific activity of the labeled oligonucleotide probes comp 12 and comp 14 was 2.86×10$^6$ cpm/pmol and 2.43×10$^6$ cpm/pmol, respectively.

TABLE 3

| | Oligonucleotides used (5' to 3') |
|---|---|
| 12 | Aminolink-spacer 18-ATC GGG TAG GTA ACC TTG CGT GCG (SEQ. ID. No. 12) |
| 14 | Aminolink-spacer 18-GGT AGG TAA CCT ACC TCA GCT GCG (SEQ. ID. No. 13) |

TABLE 3-continued

| | Oligonucleotides used (5' to 3') |
|---|---|
| comp 12 | CGC ACG CAA GGT TAC CTA CCC GAT (SEQ. ID. No. 14) |
| comp 14 | CGC AGC TGA GGT AGG TTA CCT ACC (SEQ. ID. No. 15) |

Four hundred picomoles of amino-linked capture oligonucleotides 12 and 14 (see Table 3) were deposited and reacted both on carboxyl derivatized and amino derivatized glass microscope slides as described in the previous section. The capture oligonucleotides were immobilized in a 2×2 matrix array, in such a way that hybridization with the complementary oligonucleotide probe comp 12 would result in a positive signal for the top-left and bottom-right diagonal positions, while hybridization with the complementary oligonucleotide probe comp 14 would result in a positive signal for the bottom-left and top-right diagonal positions.

Radiolabeled oligonucleotide probes comp 12 and comp 14 (see Table 3) were dissolved in hybridization solution at a concentration of 2.5 pmol/100 µl and 4.1 pmol/100 µl, respectively. The hybridization solutions were amended with 5 µl of a 2% bromophenol blue marker to facilitate the visual monitoring of the probes during their transport through the assay system. One hundred microliters of radiolabeled probe was then injected and pumped into the hybridization chamber. Hybridizations were performed for 15 min at 70° C.

After hybridization, the hybridization chamber was sequentially washed with 2×2 ml of low stringency wash buffer (2×SSC buffer contains 300 mM sodium chloride and 30 mM sodium citrate), 0.1% sodium dodecylsulfate ("SDS")) and 2×2 ml of high stringency wash buffer (0.2× SSC, 0.1% SDS) at 70° C. (1×SSC buffer contains 150 mM sodium chloride and 15 mM sodium citrate).

Example 4

Detection of Captured Oligonucleotide Probes

After washing, the capture oligonucleotide-oligonucleotide probe hybrids, silicon discs, needles and metal cover clips were removed from the glass microscope slides, and remaining liquid was absorbed using Kimwipes (Kimberly-Clark, Roswell, Ga.). The captured oligonucleotide probes were visualized and quantified using a phosphorimager (Molecular Dynamics, Sunnyvale, Calif.). After 21 hours of exposure of the glass microscope slide to a phosphorimager screen, data were collected for the different solid supports that were tested. The images that were obtained are shown in FIG. 28. Quantitative data are shown in Tables 4A and 4B.

Under the conditions that were used, the signals and cross-reactivity data that were obtained for the NH$_2$-functionalized slides were better than those obtained for the COOH-functionalized slides.

TABLE 4A

Quantification of captured oligonucleotide probe 12

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (amol) | (pic)* | (amol) | |
| —COOH | 12 | 105,333 | 9.0 | | | 0.37 |
| —COOH | 12 | 55,957 | 4.8 | | | |

TABLE 4A-continued

Quantification of captured oligonucleotide probe 12

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (amol) | (pic)* | (amol) | |
| —COOH | 12 | | | 36,534 | 3.1 | |
| —COOH | 12 | | | 23,707 | 2.0 | |
| —NH$_2$ | 12 | 353,569 | 30 | | | 0.015 |
| —NH$_2$ | 12 | 10,421,092 | 889 | | | |
| —NH$_2$ | 12 | | | 64,999 | 5.5 | |
| —NH$_2$ | 12 | | | 95,414 | 8.1 | |

*pic = relative phosphorimager counts

TABLE 4B

Quantification of captured oligonueleotide probe 14

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (amol) | (pic)* | (amol) | |
| —COOH | 14 | | | 35,610 | 4.0 | 0.19 |
| —COOH | 14 | | | 43,362 | 4.9 | |
| —COOH | 14 | 5,587 | 0.6 | | | |
| —COOH | 14 | 9,379 | 1.1 | | | |
| —NH$_2$ | 14 | | | 245,973 | 28 | 0.049 |
| —NH$_2$ | 14 | | | 115,529 | 13 | |
| —NH$_2$ | 14 | 9,775 | 1.1 | | | |
| —NH$_2$ | 14 | 8,065 | 0.9 | | | |

*pic = relative phosphorimager counts

Example 5
Optimizing Immobilization Parameters of Capture Oligonucleotides

Polymer was deposited on slides using a literature procedure. Barnard, et al., "A Fibre-optic Sensor With Discrete Sensing Sites," Nature 353:338–40 (1991); Bonk, et al., "Fabrication of Patterned Sensor Arrays With Aryl Azides on a Polymer-coated Imaging Optical Fiber Bundle," Anal. Chem. 66:3319–20 (1994); Smith, et al., "Poly-N-acrylylpyrrolidone—A New Resin in Peptide Chemistry," Int. J. Peptide Protein Res. 13:109–12 (1979), which are hereby incorporated by reference.

Four hundred picomoles of amino-linked capture oligonucleotides 12 and 14 (see Table 3) were deposited and reacted in a 2×2 pattern to a glass microscope slide that contained 4 identical photo-deposited polymer spots. The oligonucleotides were spotted in such a way that hybridization with the complementary oligonucleotide probe comp 12 would result in a positive signal for the top and bottom positions, while hybridization with the complementary oligonucleotide probe comp 14 would result in a positive signal for the left and right positions.

Radiolabeled oligonucleotide probe comp 12 (see Table 3) was dissolved in hybridization solution at a concentration of 2.4 pmol/100 μl.
Bromophenol Blue Marker
(5 μl of a 2% solution) was added to the hybridization solution to facilitate the monitoring of the probe during its transport through the system.

One hundred microliters of radiolabeled probe comp 12 was pumped into the hybridization chamber. Hybridization was performed for 15 min at 70° C. After hybridization, the hybridization chamber was sequentially washed with 3×1 ml of low stringency wash buffer (2×SSC, 0.1% SDS) and 3×1 ml of high stringency wash buffer (0.2×SSC, 0.1% SDS) at 70° C.

Figure 29:
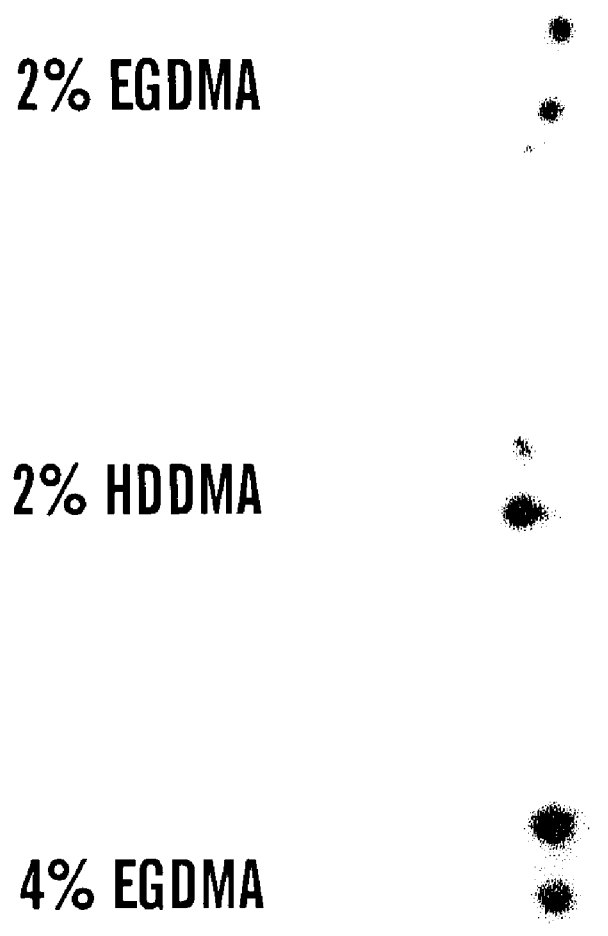

After 24 hours of exposure of the glass microscope slide to a phosphorimager screen, data were collected for all the different slides that were tested. The images that were obtained are shown in FIG. 29. Quantitative data are shown in Table 5.

TABLE 5

Quantification of captured oligonucleotide probes

| Crosslinker | Percentage crosslinker | probe 12 (pic)* | probe 12 (amol) |
|---|---|---|---|
| EGDMA | 2 | 1,055,100 | 80 |
| | | 1,390,499 | 106 |
| HDDMA | 2 | 633,208 | 48 |
| | | 286,9371 | 218 |
| EGDMA | 4 | 4,449,001 | 338 |
| | | 2,778,414 | 211 |

EGDMA = ethylene glycol dimethacrylate
HDDMA = hexane diol dimethacrylate
*pic = relative phosphorimager counts The immobilization chemistry allows for the use of tailor-made specialty polymer matrices that provide the appropriate physical properties that are required for efficient capture of nucleic acid amplification products. The specificity of the immobilized capture oligonucleotides has been relatively good compared to current strategies in which single mismatches, deletions, and insertions are distinguished by differential hybridization (K. L. Beattie, et. al. "Advances in Genosensor Research," Clin. Chem. 41:700–06 (1995), which is hereby incorporated by reference). Finally, it has been demonstrated that the assay system of the present invention enables the universal identification of nucleic acid oligomers.

Example 6

Capture of Addressable Oligonucleotide Probes to Solid Support

Polymer-coated slides were tested for their capture capacity of addressable oligonucleotide probes following different procedures for immobilization of capture oligonucleotides. After being silanized with 3-(trimethoxysilyl) propyl methacrylate, monomers were then polymerized on the slides. In one case, a polymer layer having COOH functional groups was formed with a polyethylene glycol-containing crosslinker. In the other case, a polyethylene glycol-methacrylate monomer was polymerized onto the slide to form OH functional groups. The slides with the COOH functional groups were activated using the EDC-activation procedure of Example 1.

The slide with OH functional groups was activated overnight at room temperature by incubation in a tightly closed 50 ml plastic disposable tube (Corning Inc., Corning, N.Y.) containing 0.2 M 1,1'-carbonyldiimidazole ("CDI") (Sigma Chemical Co., St. Louis, Mo.) in "low water" acetone (J. T. Baker, Phillipsburg, N.J.). The slide was then washed with "low water" acetone, and dried in vacuum at room temperature.

Amino-linked capture oligonucleotide 14 was manually spotted on premarked locations on both sides (4 dots per slide). The reactions were performed in a hood, and the amount of oligonucleotide that was spotted was 2×0.2 µl (0.8 nmol/µl). The total reaction time was 1 hr. The slides were then quenched for 15 min by the application of few drops of propylamine on each of the premarked dots. After quenching, the slides were incubated for 5 min in 0.1 N sodium phosphate buffer, pH 7.2, washed in double distilled $H_2O$, and dried in vacuum.

The complementary capture oligonucleotides on the slides were hybridized with radioactively labeled oligonucleotide probe comp 14 (Table 3). One hundred microliters radiolabeled oligonucleotide probe comp 14 (2.8 pmol; 6,440,000 cpm/pmol) were pumped into the hybridization chamber. Hybridization was performed for 15 min at 70° C. in 0.5 M $Na_2HPO_4$ [pH 7.2], 1% crystalline grade BSA, 1 mM EDTA, 7% SDS. After hybridization, the hybridization chamber was sequentially washed with 2×2 ml of low stringency wash buffer (2×SSC, 0.1% SDS) and 2×2 ml of high stringency wash buffer (0.2×SSC, 0.1% SDS) at 70° C. (1 SSC buffer contains 150 mM sodium chloride and 15 mM sodium citrate).

Figure 30:
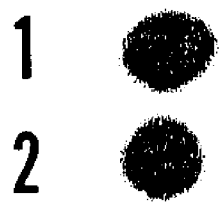
FIG. 30 shows phosphorimager data for —OH functionalized slides.

After 30 min of exposure of the glass microscope slide to a phosphorimager screen, data were collected for both slides. After 30 minutes of exposure of the glass microscope slides to a phosphorimager screen, data were collected. See Table 6 and FIG. 30.

TABLE 6

Quantification of capture oligonucleotide probe 14 on OH-functionalized slides

| Functional group on glass slide | Probe | Oligonucleotide probe at capture oligonucleotide 14 (pic)* | (fmol) |
|---|---|---|---|
| -OH | 14 | 1,864,879 | 10.9 |
| -OH | 14 | 1,769,403 | 10.3 |

*pic = relative phosphorimager counts

In this test, better results were obtained with the slide coated with the polymer containing OH functional groups than with the slide coated with the polymer containing COOH functional groups.

With previously prepared (poly HEMA)-containing polymers that were polymerized with 20% amine-containing monomers and crosslinked with 4% EGDMA or HDDMA, it was possible to capture about 275 amol of radioactively labelled ligated product sequence (which could only be visualized after 23 hours of exposure to a phosphorimager screen (Table 5)). Using the polyethylene-methacrylate polymer formulations, it was possible to capture about 10.6 fmoles of ligated product sequence. The signal could be detected after 30 min of exposure.

Example 7

Detection of Captured Oligonucleotides Using a Membrane Support

In order to assess the capture specificity of different capture oligonucleotides using a membrane support, hybridization experiments were carried out using the capture oligonucleotide probes 12 and 14 (Table 3).

Strips of OH-functionalized nylon membrane (Millipore, Bedford, Mass.) were soaked overnight in a 0.2 M solution of carbonyldiimidazole in "low water" acetone. The strips were washed in acetone and dried in vacuo. Two volumes of 0.2 µl (1mM) capture oligonucleotides 12 and 14 in 20 mM $K_2HPO_4$, pH 8.3, (Table 3) were loaded on the membrane using a special blotting device (Immunetics, Cambridge, Mass.). Complementary oligonucleotide probes were radioactively labeled as described in Example 3. The oligonucleotide probes were dried in vacuo and taken up in 200 µl hybridization buffer (0.5 M $Na_2HPO_4$ [pH 7.2], 1% crystalline grade BSA, 1 mM EDTA, 7% SDS). Membranes were prehybridized in 800 µl hybridization buffer for 15 min at 60° C. in 1. 5ml Eppendorf tubes in a Hybaid hybridization oven. The tubes were filled with 500 µl of inert carnauba wax (Strahl & Pitsch, Inc., New York, N.Y.) to reduce the total volume of the hybridization compartment. After prehybridization, 200 µl of radiolabeled probe was added. The membranes were hybridized for 15 min at 60° C. After hybridization, the membranes were washed at 60° C., twice for 15 min with 1 ml of low stringency wash buffer (2×SSC, 0.1% SDS), and twice for 15 min with 1 ml of high stringency wash buffer (0.2×SSC, 0.1% SDS). The captured oligonucleotide probes were quantified using a phosphorimager (Molecular Dynamics, Sunnyvale, Calif.). After 45 min of exposure to a phosphorimager screen, data were collected. The results are shown in Table 7, where the activities of capture oligonucleotides 12 and 14 are 112 pic/amol and 210 pic/amol, respectively.

TABLE 7

Quantification of captured oligonucleotides on membranes

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (fmol) | (pic)* | (fmol) | |
| —OH | 12 | 13,388,487 | 119.5 | 337,235 | 3.01 | 0.025 |
| —OH | 12 | 13,299,298 | 118.7 | | | |
| —OH | 14 | 179,345 | 0.85 | 1,989,876 | 9.48 | 0.071 |
| —OH | 14 | | | 3,063,387 | 14.59 | |

*pic = relative phosphorimager counts

Hybridization temperatures and hybridization times were further explored in a series of similar experiments. The data shown in Table 8 (where the activities of capture oligonucleotides 12 and 14 are 251 pic/amol and 268 pic/amol, respectively) represent the results obtained with the following conditions: 15 min prehybridization at 65° C. in 800 µl hybridization buffer; 15 min hybridization at 65° C. in 1 ml hybridization buffer; 2×washings for 5 min at 65° C. with 1 ml of low stringency wash buffer; and 2×washings for 5 min at 65° C. with 1 ml of high stringency wash buffer.

TABLE 8

Quantification of captured oligonucleotides on membranes

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (fmol) | (pic)* | (fmol) | |
| —OH | 12 | 41,023,467 | 163.4 | 541,483 | 2.16 | 0.015 |
| —OH | 12 | 31,868,432 | 127.0 | | | |
| —OH | 14 | 294,426 | 1.10 | 19,673,325 | 73.41 | 0.016 |
| —OH | 14 | | | 18,302,187 | 68.29 | |

*pic = relative phosphorimager counts

The data shown in Table 9 (where the activities of capture oligonucleotides 12 and 14 are 487 pic/amol and 506 pic/amol, respectively) represent the results obtained with the following conditions: 15 min prehybridization at 70° C. in 150 µl hybridization buffer; 15 min hybridization at 70° C. in 200 µl hybridization buffer; 2×washings for 5 min at 70° C. in 800 µl of low stringency wash buffer; and 2×washings for 5 min at 70° C. in 800 µl of high stringency wash buffer.

The data shown in Table 10 represent the results obtained with the following conditions: 15 min prehybridization at 70° C. in 150 µl hybridization buffer; 5 min hybridization at 70° C. in 200 µl hybridization buffer; 2×washings for 5 min at 70° C. with 800 µl of low stringency wash buffer; and 2×washings for 5 min at 70° C. with 800 µl of high stringency wash buffer.

TABLE 9

Quantification of captured oligonucleotides on membranes

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (fmol) | (pic)* | (fmol) | |
| —OH | 12 | 34,648,385 | 71.15 | 1,158,832 | 2.38 | 0.027 |
| —OH | 12 | 52,243,549 | 107.28 | | | |
| —OH | 14 | 1,441,691 | 2.85 | 56,762,990 | 112.18 | 0.028 |
| —OH | 14 | | | 45,769,158 | 90.45 | |

*pic = relative phosphorimager counts

TABLE 10

Quantification of captured oligonucleotides on membranes.

| Functional group on slide | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (fmol) | (pic)* | (fmol) | |
| —OH | 12 | 26,286,188 | 53.98 | 389,480 | 0.80 | 0.013 |
| —OH | 12 | 34,879,649 | 71.62 | | | |
| —OH | 14 | 539,486 | 1.07 | 45,197,674 | 89.32 | 0.011 |
| —OH | 14 | | | 54,409,947 | 107.53 | |

*pic = relative phosphorimager counts

The data shown in Table 11 represent the results obtained with the following conditions: 5 min prehybridization at 70° C. in 150 μl hybridization buffer; 1 min hybridization at 70° C. in 200 μl hybridization buffer; 2×washings for 2 min at 70° C. with 800 μl of low stringency wash buffer; and 2×washings for 5 min at 70° C. with 800 μl of high stringency wash buffer.

TABLE 11

Quantification of captured oligonucleotides on membranes

| Functional group on membrane | Probe | Oligonucleotide probe at capture oligonucleotide 12 | | Oligonucleotide probe at capture oligonucleotide 14 | | Average cross reactivity |
|---|---|---|---|---|---|---|
| | | (pic)* | (fmol) | (pic)* | (fmol) | |
| —OH | 12 | 5,032,835 | 10.33 | 56,777 | 0.12 | 0.012 |
| —OH | 12 | 4,569,483 | 9.38 | | | |
| —OH | 14 | 540,166 | 1.07 | 41,988,355 | 82.98 | 0.017 |
| —OH | 14 | | | 20,357,554 | 40.23 | |

*pic = relative phosphorimager counts

These data demonstrate that hybridization of the capture oligonucleotide probes to their complementary sequences was specific. In comparison with the previous experiments performed with glass slides, significantly greater amounts (i. e., fmol quantities compared to amol quantities) of oligonucleotide probes were reproducibly captured on the membrane supports. For these two very closely-related capture oligonucleotide probes, average cross-reactivity values of about 1% could be obtained. However, for other pairs of capture oligonucleotides in the array, these values would be significantly better. In general, such values cannot be achieved by using existing methods that are known in the art, i. e., by allele-specific oligonucleotide hybridization ("ASO") or by differential hybridization methods, such as sequencing by hybridization ("SBH").

Example 8
Cleaning Glass Surfaces

Glass slides (Fisher Scientific, Extra thick microslides, frosted cat.# 12-550-11) were incubated in conc. aq. $NH_4OH$—$H_2O_2$—$H_2O$ (1:1:5, v/v/v) at 80° C. for 5 min and rinsed in distilled water. A second incubation was performed in conc. aq HCl—$H_2O_2$—$H_2O$ (1:1:5, v/v/v) at 80° C. for 5 min. See U. Jönsson, et al., "Absorption Behavior of Fibronectin on Well Characterized Silica Surfaces," *J. Colloid Interface Sci.* 90:148–163 (1982), which is hereby incorporated by reference. The slides were rinsed thoroughly in distilled water, methanol, and acetone, and were air-dried at room temperature.

Example 9
Silanization with 3-methacryloyloxypropyltrimethoxysilane

Figure 31:
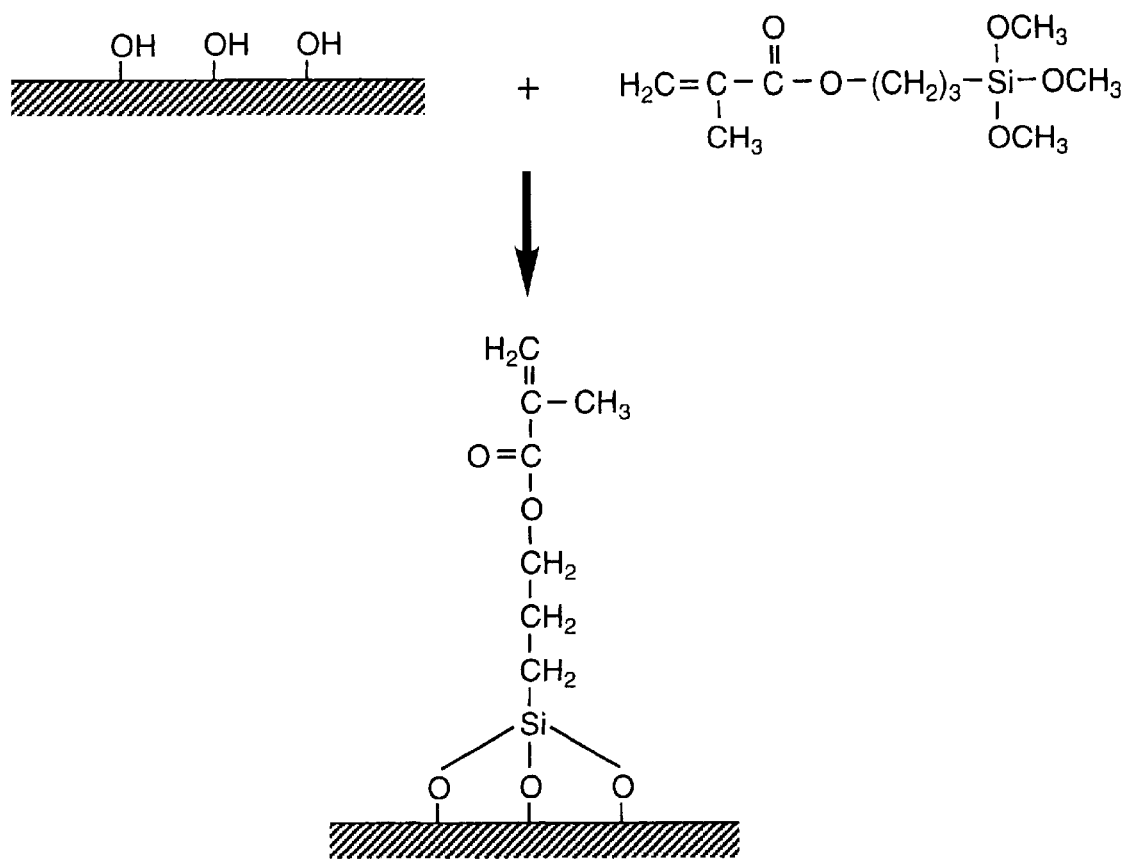
FIG. 31 shows the reaction scheme for producing a glass slide silanized with 3-methacryloyloxypropyltrimethoxysilane.

Cleaned slides, prepared according to Example 8, were incubated for 24–48 h at room temperature in a solution consisting of 2.6 ml of 3-methacryloyloxypropyltrimethoxysilane (Aldrich Chemical Company, Inc. Milwaukee, Wis. cat.# 23,579-2), 0.26 ml of triethylamine, and 130 ml of toluene. See E. Hedborg, et. al., *Sensors Actuators A,* 37–38:796–799 (1993), which is hereby incorporated by reference. The slides were rinsed thoroughly in acetone, methanol, distilled water, methanol again, and acetone again, and were air-dried at room temperature. See FIG. 31.

Example 10
Silanization with Dichlorodimethylsilane

Cleaned slides, prepared according to Example 8, were incubated for 15 min at room temperature in a solution containing 12 ml of dichlorodimethylsilane and 120 ml of toluene. The slides were rinsed thoroughly in acetone, methanol, distilled water, methanol again, and acetone again and were air-dried.

Figure 32:
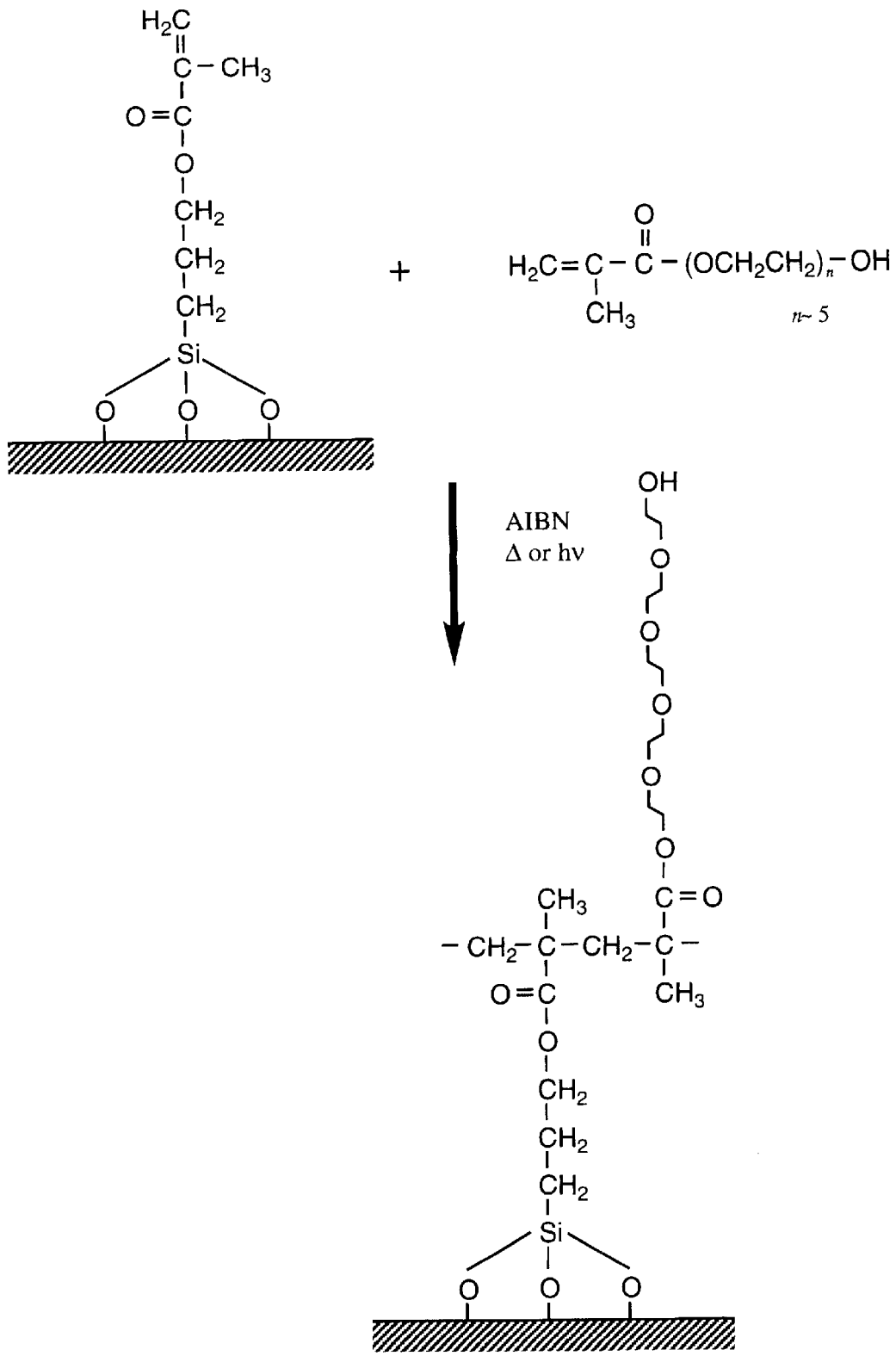
FIG. 32 shows the reaction scheme for producing polymerized poly(ethylene glycol)methacrylate on a glass slide silanized with 3-methacryloyloxypropyl-trimethoxy-silane.

Example 11
Polymerization of Poly(ethylene glycol)methacrylate with Methacrylate-derivatized Glass 2.2 g of poly(ethylene glycol)methacrylate (Aldrich Chemical Company, Inc. Milwaukee, Wis. cat.# 40,953-7) (average M~306 g/mol) and 50 mg of 2,2'-azobis(2-methylpropionitrile) in 3.5 ml of acetonitrile were cooled on ice and purged with a stream of argon for 3 min. The next steps were performed in a glove-box under argon atmosphere. 5–15 drops of the polymerization mixture were placed on a methacrylate-derivatized glass slide, prepared according to Examples 8 and 9. The methacrylate-derivatized glass slide and the polymerization mixture were covered by a second glass slide which had been silanized according to Example 10, and the two glass slides were pressed together and fixed with clips. The slides were subsequently transferred to a vacuum desiccator. The polymerization was thermolytically initiated at 55° C., or photolytically at 366 nm. See FIG. 32.

Figure 33:
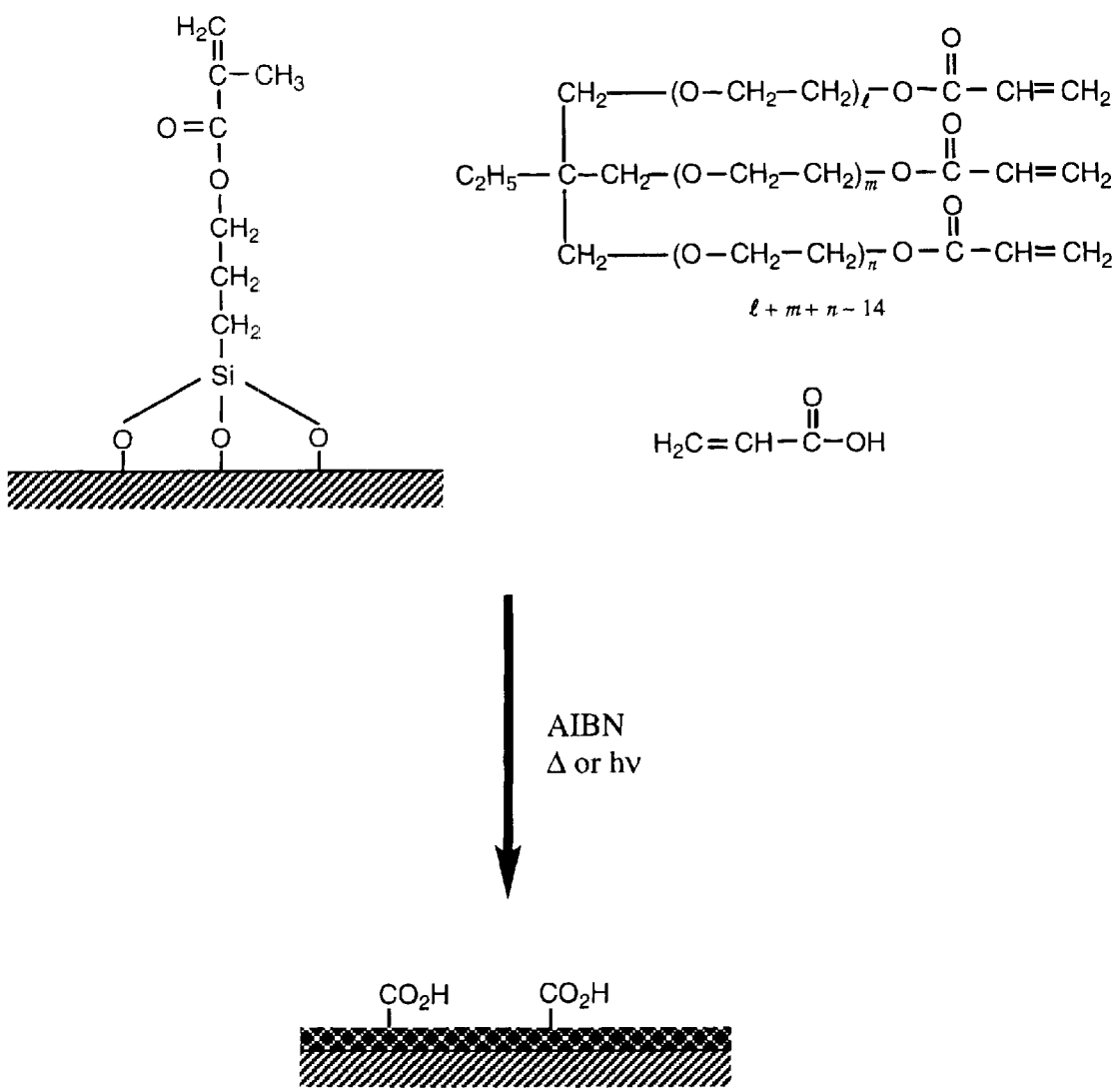
FIG. 33 shows the reaction scheme for producing polymerized acrylic acid and trimethylolpropane ethoxylate (14/3 EO/OH) triacrylate on a glass slide silanized with 3-methacryloyloxypropyltrimethoxysilane.

Example 12
Polymerization of Acrylic Acid and Trimethylolpropane Ethoxylate (14/3 EO/OH) Triacrylate with Methacrylate-Derivatized Glass 0. 5 g of acrylic acid (Aldrich Chemical Company, Inc. Milwaukee, Wis. cat.# 14,723–0), 1.83 g of trimethylolpropane ethoxylate (14/3 EO/OH) triacrylate (Aldrich Chemical Company, Inc. Milwaukee, Wis. cat.# 23,579-2), and 50 mg of 2,2'-azobis(2-methylpropionitrile) in 3. 5 ml of acetonitrile were cooled on ice and purged with a stream of argon for 3 min. The next steps were performed in a glovebox as described in Example 11. The slides were subsequently transferred to a vacuum desiccator and polymerized as described in Example 11. See FIG. 33.

Figure 34:
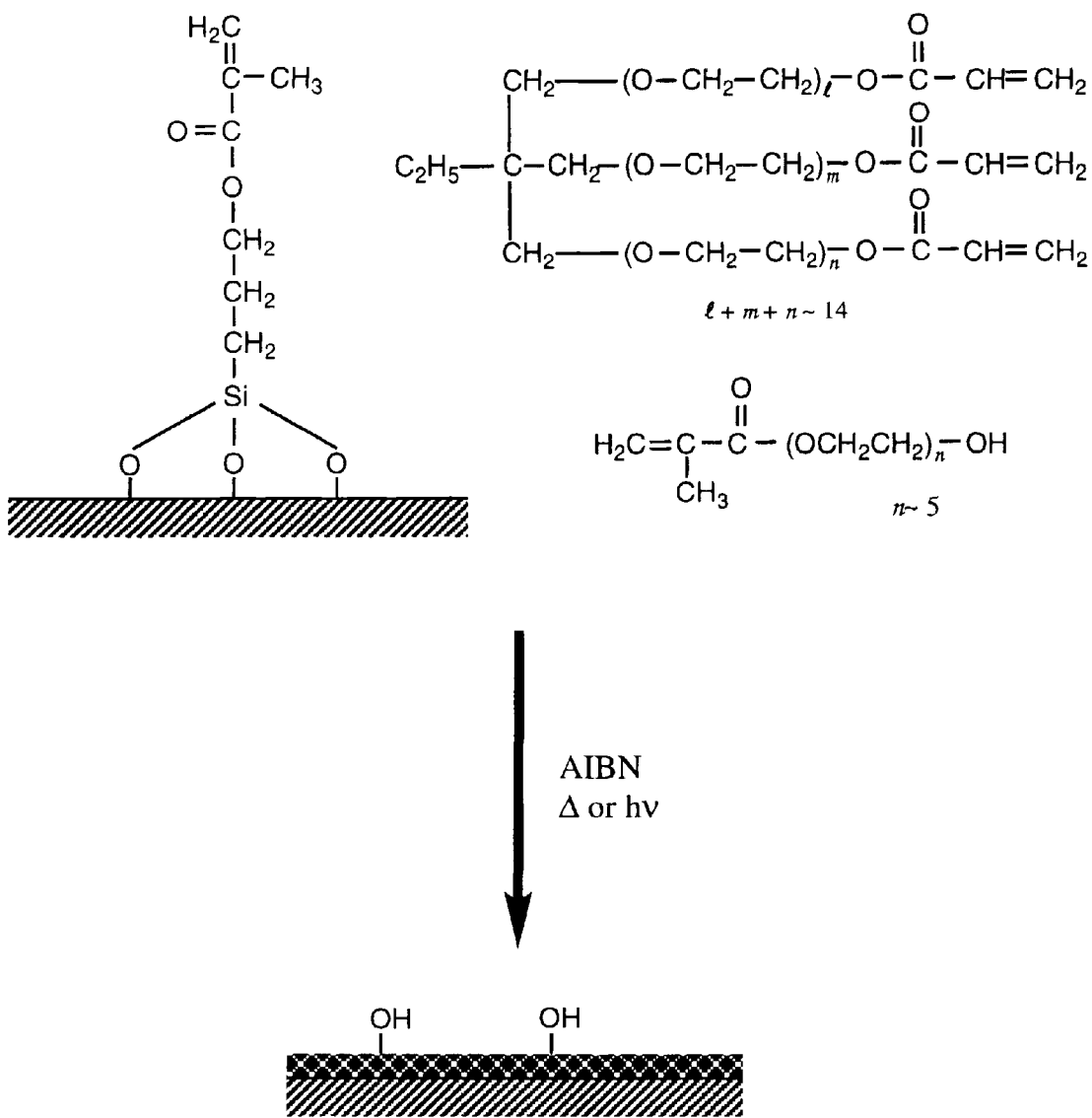
FIGS. 34A–B show the reaction scheme for producing polymerized poly(ethylene glycol)methacrylate and trimethylolpropane ethoxylate (14/3 EO/OH) triacrylate on a glass slide silanized with 3-methacryloyloxypropyltrimethoxysilane.

Example 13
Polymerization of Poly(ethylene glycol)methacrylate and Trimethylolpropane Ethoxylate (14/3 EO/OH) Triacrylate with Methacrylate-derivatized Glass 0. 55 g of poly(ethylene glycol)methacrylate (Aldrich Chemical Company, Inc. Milwaukee, Wis. cat.# 40,953,7), 1. 64 g of trimethylolpropane ethoxylate (14/3 EO/OH triacrylate (Aldrich Chemical Company, Inc. Milwaukee, Wis. cat.# 23,579-2), and 50 mg of 2,2'-azobis(2-methylpropionitrile) in 3.5 ml of acetonitrile were cooled on ice and purged with a stream of argon for 3 min. The next steps were performed in a glove-box as described in Example 11. The slides were subsequently transferred to a vacuum desiccator and polymerized as described in Example 11. See FIG. 34.

Example 14
Materials and Methods

Oligonucleotide Synthesis and Purification. Oligonucleotides were obtained as custom synthesis products from IDT, Inc. (Coralville, Iowa), or synthesized in-house on an ABI 394 DNA Synthesizer (PE Biosystems Inc.; Foster City, Calif.) using standard phosphoramidite chemistry. Spacer phosphoramidite 18, 3'-amino-modifer C3 CPG, and 3'-fluorescein CPG were purchased from Glen Research (Sterling, Va.). All other reagents were purchased from PE Biosystems. Oligonucleotides with 3'-amino modifications and/or fluorescent labels were cleaved from the supports of treatment with concentrated aqueous $NH_4OH$, 2 h at 25° C. Texas Red labeling was achieved by adding 0.2 M $NaHCO_3$ (150 $\mu L$) and oligonucleotide (200 $\mu g$) to tubes containing a solution of Texas Red-X succinimidyl ester (500 $\mu g$) (Molecular Probes; Eugene, Oreg.) in anhydrous DMF (28 $\mu L$). Following overnight stirring at 25° C., the majority of unreacted label was removed by the addition of 3 M NaCl (20 $\mu L$) and cold ethanol (500 $\mu L$), chilling in a dry ice-ethanol bath for 30 minutes, and centrifuging at 12,000 g for 30 minutes. The supernatants were removed, the pelleted oligonucleotides were washed with 70% ethanol (100 $\mu L$)), and dried. FAMcZip13-Prd, a fluorescein-labeled 70-mer that simulates a full-length LDR product containing the complementary sequence to Zip13, was synthesized on 1000 Å pore-size CPG. The sequence was: 5'-fluorescein-CGCACGATAGGTGGTCTACCGCTGATATAAACTTGT GGGGAGCTAGTGGCGTAGGCAAGAGTGCC-3' (SEQ. ID. No. 16) (the addressable array-specific portion is in bold). Both labeled and unlabeled oligonucleotides were purified by electrophoresis on 12% denaturing polyacrylamide gels. Bands were visualized by UV shadowing, excised from the gel, and eluted overnight in 0. 5 M NaCl, 5 mM EDTA, pH 8. 0 at 37° C. Oligonucleotide solutions were desalted on C18 Sep-Paks (Waters Corporation; Milford, Ma.) according to the manufacturer's instructions, following which the oligonucleotides were concentrated to dryness (Speed-Vac) and stored at −20° C.

Polymer Coated Slides. Microscope slides (Fisher Scientific, precleaned, 3 in.×1 in.×1.2 mm) were immersed in 2%—methacryloxypropyltrimethoxysilane—0.2% triethylamine in $CHCl_3$ for 30 min at 25° C., and then washed with $CHCl_3$ (2×15 min). A monomer solution [20 L: 8% acrylamide—2% acrylic acid—0.02% N,N'-methylenebisacrylamide (500:1 ratio of monomers:crosslinker)—0.8% ammonium persulfate radical polymerization initiator] was deposited on one end of the slides and spread out with the aid of a cover slip (24×50 mm) that had been previously silanized [5% $(CH_3)_2SiCl_2$ in $CHCl_3$]. Polymerization was achieved by heating the slides on a 70° C. hotplate for 4.5 min. Upon removal of the slides from the hot plate, the cover slips were immediately peeled off with aid of a single-edge razor blade. The coated slides were rinsed with deionized water, allowed to dry in open atmosphere, and stored under ambient conditions.

Addressable Arrays. Polymer-coated slides were pre-activated by immersing them for 30 min at 25° C. in a solution of 0.1 M 1-[3-(dimethylamino)propyl]-3-ethylcarbodiimide hydrochloride plus 20 mM N-hydroxysuccinimide in 0.1 M $K_2HPO_4/KH_2PO_4$, pH 6.0. The activated slides were rinsed with water, and then dried in a 65° C. oven; they were stable upon storage for 6 months or longer at 25° C. in a desiccator over Drierite.

For manual spotting, 0.2 $\mu L$ aliquots were taken with a Rainin Pipetman from stock solutions (500 $\mu M$) of capture oligonucleotides in 0.2 M $K_2HPO_4/KH_2PO_4$, pH 8.3, and deposited in a 3×3 array onto the pre-activated polymeric surfaces. The resulting arrays were incubated for 1 h at 65° C. in humidified chambers containing water-formamide (1:1). For robotic spotting, 10–50 nL aliquots of capture oligonucleotides (1.5 mM in the same buffer) were deposited at 25° C. on the pre-activated surfaces by using a robot equipped with a quill-type spotter in a controlled atmosphere chamber. Two pairs of 3×3 arrays were spotted on each slide, with addresses consisting of groups of four spots. Following spotting using either method, uncoupled oligonucleotides were removed from the polymer surfaces by soaking the slides in 300 mM bicine, pH 8.0—300 mM NaCl—0.1% SDS, for 30 min at 65° C., rinsing with water, and drying. The arrays were stored at 25° C. in slide boxes until needed.

PCR Amplification of K-ras DNA Samples. PCR amplifications were carried out under paraffin oil in 20 L reaction mixtures containing 10 mM Tris.HCl, pH 8.3—1.5 mM $MgCl_2$—50 mM KCl, 800 $\mu M$ dNTPs, 2. 5 $\mu M$ forward and reverse primers (12.5 pmol of each primer; see Table 12), and 1–50 ng of genomic DNA extracted from paraffin-embedded tumors or from cell lines. Following a 2 min denaturation step at 94° C., 0.2 units of Taq DNA polymerase (PE Biosystems) was added.

TABLE 12

Primers and probes designed for K-ras mutation detection by PCR/LDR/Array Hybridization.

| Primer/Probe | Sequence (5'→3') |
|---|---|
| K-ras exon 1 forward | ATAAGGCCTGCTGAAAATGACTGAA (SEQ. ID. No. 17) |
| K-ras exon 1 reverse | CTGCACCAGTAATATGCATATTAAAACAAG (SEQ. ID. No. 18) |
| cZip1-K-ras c12.2WtG | GCTGAGGTCGATGCTGAGGTCGCAAAACTTGTGGTAGTTGGAGCTG<u>G</u> (SEQ. ID. No. 19) |
| cZip3-K-ras c12.2D | GCTGCGATCGATGGTCAGGTGCTGAAACTTGTGGTAGTTGGAGCTG<u>A</u> (SEQ. ID. No. 20) |
| cZip5-K-ras c12.2A | GCTGTACCCGATCGCAAGGTGGTCAAACTTGTGGTAGTTGGAGCTG<u>C</u> (SEQ. ID. No. 21) |
| cZip11-K-ras c12.2V | CGCAAGGTAGGTGCTGTACCCGCAAAACTTGTGGTAGTTGGAGCTG<u>T</u> (SEQ. ID. No. 22) |
| K-ras c12 Com-2 | pTGGCGTAGGCAAGAGTGCCT-fluorescein (SEQ. ID. No. 23) |
| | pTGGCGTAGGCAAGAGTGCCT-Texas Red (SEQ. ID. No. 24) |
| cZip13-K-ras c12.1S | CGCACGATAGGTGGTCTACCGCTGATATAAACTTGTGGTAGTTGGAGCT<u>A</u> (SEQ. ID. No. 25) |
| cZip15-K-ras c12.1R | CGCACGATAGGTGGTCTACCGCTGATATAAACTTGTGGTAGTTGGAGCT<u>C</u> (SEQ. ID. No. 26) |
| cZip21-K-ras c12.1C | GGTCAGGTTACCGCTGCGATCGCAATATAAACTTGTGGTAGTTGGAGCT<u>T</u> (SEQ. ID. No. 27) |
| K-ras c12 Com-1 | pGTGGCGTAGGCAAGAGTGCC-florescein (SEQ. ID. No. 28) |
| | pGTGGCGTAGGCAAGAGTGCC-Texas Red (SEQ. ID. No. 29) |
| cZip23-K-ras c13.4D | GGTCCGATTACCGGTCCGATGCTGTGTGGTAGTTGGAGCTGGTG<u>A</u> (SEQ. ID. No. 30) |
| cZip25-K-ras c13.4WtG | GGTCTACCTACCCGCACGATGGTCTGTGGTAGTTGGAGCTGGTG<u>G'</u> (SEQ. ID. No. 31) |
| K-ras c13 Com-4 | pCGTAGGCAAGAGTGCCTTGAC-fluorescein (SEQ. ID. No. 32) |
| | pCGTAGGCAAGAGTGCCTTGAC-Texas Red (SEQ. ID. No. 33) |

The PCR primers were specifically designed to amplify exon I of K-ras without co-amplifying N- and H-ras. The allele-specific LDR probes contained 24-mer addressable array specific portions on their 5'-ends (bold) and the discriminating bases on their 3'-ends (underlined). The common LDR probes contained 5'-phosphates and either a fluorescein or a Texas Red label on their 3'-ends.

Amplification was achieved by thermal cycling for 40 rounds of 94° C. for 15 sec and 60° C. for 2 min, followed by a final elongation step at 65° C. for 5 min. Following PCR, 1 µL of Proteinase K (18 mg/mL) was added, and reactions were heated to 70° C. for 10 min and then quenched at 95° C. for 15 min. One µL of each PCR product was analyzed on a 3% agarose gel to verify the presence of amplification product of the expected size.

Figure 35:
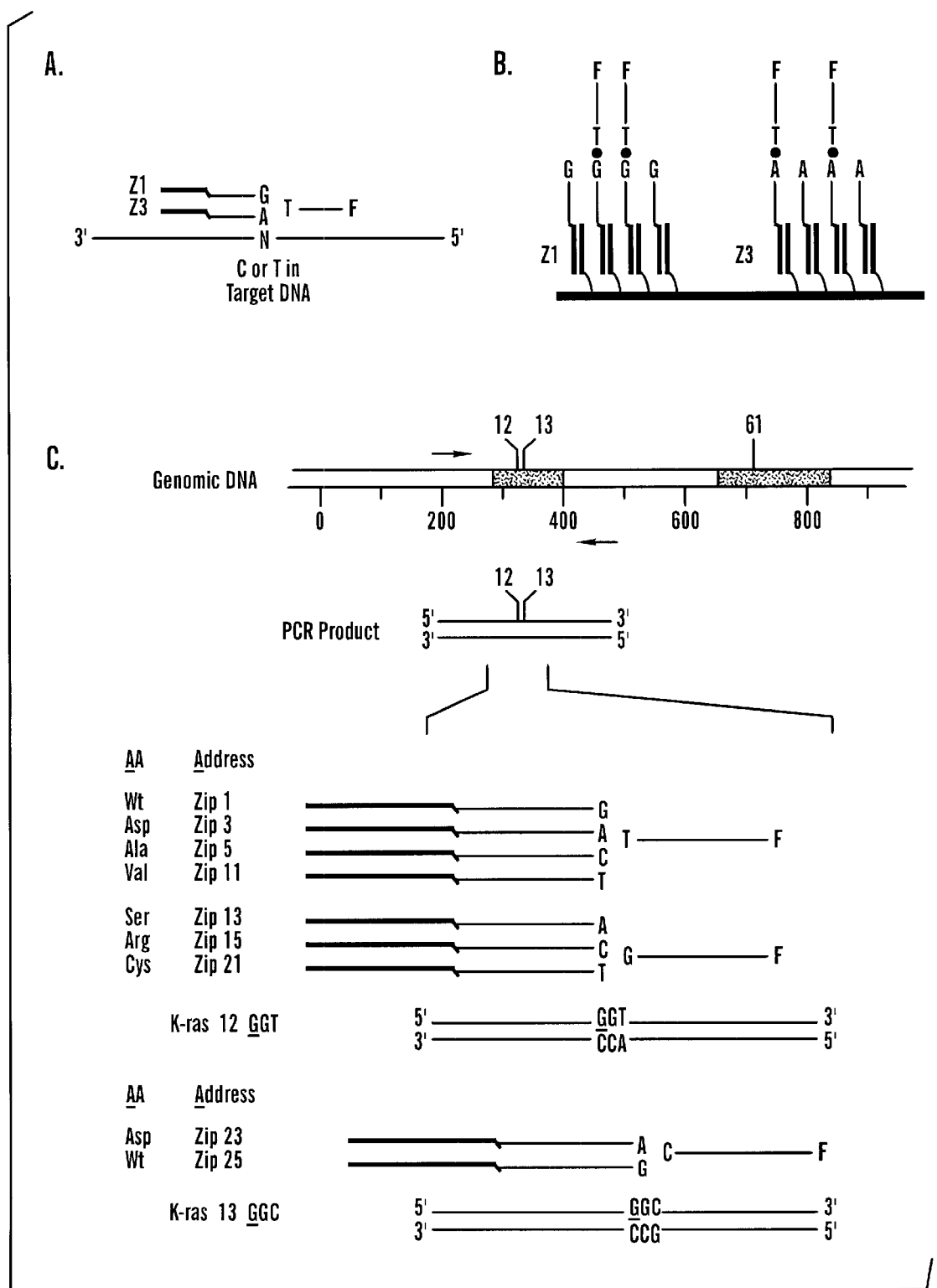
FIGS. 35A–C show a scheme for PCR/LDR detection of mutations using an addressable array.

LDR of K-ras DNA samples. LDR reactions were carried out under paraffin oil in 20 µL volumes containing 20 mM Tris.HCl, pH 8.5—5 mM $MgCl_2$ 13 100 mM KCl, 10 mM DTT, 1 mM $NAD^+$, 8 pmol total LDR probes (500 fmol each of discriminating probes+4 pmol fluorescently-labeled common probes), and 1 pmol PCR products from cell line or tumor samples. Two probe mixes were prepared, each containing the seven mutation-specific probes, the three common probes, and either the wild-type discriminating probe for codon 12 or that for codon 13 (FIG. 35C and Table 12).

The reaction mixtures were pre-heated for 2 min at 94° C., and then 25 fmol of wild-type Tth DNA ligase was added. The LDR reactions were cycled for 20 rounds of 94° C. for 15 sec and 65° C. for 4 min. An aliquot of 2 µL of each reaction was mixed with 2 L of gel loading buffer [8% blue dextran, 50 mM EDTA, pH 8.0—formamide (1:5)], denatured at 94° C. for 2 min, and chilled on ice. One µL of each mixture was loaded on a 10% denaturing polyacrylamide gel and electrophoresed on an ABI 377 DNA sequencer at 1500 volts.

Hybridization of K-ras LDR Products to DNA Arrays. The LDR reactions (17 µL) were diluted with 40 µL of 1.4×hybridization buffer to produce a final buffer concentration of 300 mM MES, pH 6.0—10 mM $MgCl_2$—0.1% SDS. Arrays were pre-incubated for 15 min at 25° C. in 1×hybridization buffer. Coverwells (Grace, Inc; Sunriver, Oreg.) were filled with the diluted LDR reactions and attached to the arrays. The arrays were placed in humidified culture tubes and incubated for 1 h at 65° C. and 20 rpm in a rotating hybridization oven. Following hybridization, the arrays were washed in 300 mM bicine, pH 8.0—10 mM $MgCl_2$—0.1% SDS for 10 min at 25° C. Fluorescent signals were measured using a microscope/CCD (see "Image Analysis").

Hybridization of Synthetic LDR Products to DNA Arrays. Quadruplicate hybridization mixtures were prepared containing 100 amol, 1 fmol, 3 fmol, 10 fmol, or 30 fmol FAMcZip 13-Prd (a synthetic 70-mer LDR product complementary to address 13) combined with 4,500 fmol total fluorescein-labeled common LDR probes and 9×500 fmol of each unlabeled, addressable array-specific portion containing discriminating LDR probe in 55 µL of 300 mM MES, pH 6.0—10 mM $MgCl_2$—0.1% SDS. Hybridizations were conducted according to the protocol described in the preceding section, and FluorImager as well as epifluorescence microscopy data were acquired and analyzed (see "Image Analysis").

LDR and Hybridization of G12V/G12 Dilution Series to DNA Arrays. These experiments were carried out in a volume of 20 µL. PCR-amplified SW620 cell line DNA containing the G12V mutation was diluted from 5 nM (100 fmol=1/20) to 0.050 nM (1 fmol=1/2,000) in LDR mixtures containing 100 nM (2,000 fmol) of wild-type (G12) DNA and 100 nM (2,000 fmol) of both G12V discriminating probe and Texas Red-labeled common probe. The LDR and hybridization proceeded as above, and imaging on the microscope/CCD were carried out as detailed in "Image Analysis".

Image Analysis. Arrays were imaged using a Molecular Dynamics FluorImager 595 (Sunnyvale, Calif.) or an Olympus AX70 epifluorescence microscope (Melville, N.Y.) equipped with a Princeton Instruments TE/CCD-512 TKBM1 camera (Trenton, N.J.). For analysis of fluorescein-labeled probes on the FluorImager, the 488 nm excitation was used with a 530/30 emission filter. The spatial resolution of scans was 100 μm per pixel. The resulting images were analyzed using ImageQuaNT software provided with the instrument. The epifluorescence microscope was equipped with a 100 W mercury lamp, a FITC filter cube (excitation 480/40, dichroic beam splitter 505, emission 535/50), a Texas Red filter cube (excitation 560/55, dichroic beam splitter 595, emission 645/75), and a 100 mm macro objective. The macro objective allows illumination of an object field up to 15 mm in diameter and projects a 7×7 mm area of the array onto the 12.3×12.3 mm matrix of the CCD. Images were collected in 16-bit mode using the Winview32 software provided with the camera. Analysis was performed using Scion Image (Scion Corporation, Frederick, Md.).

Example 15
Capture Address Design

The approach of the present invention relies on designed capture sequences of 24 bases, termed "address," which are very different from each other and also lack any homology to either the target sequence or to other sequences on the genome (Table 13).

TABLE 13

Address sequences used in prototype array.

| Zip# | Tetramer order* | Zip-code Sequence (5' → 3')† |
|---|---|---|
| Zip1 | 1-6-3-2-6-3 | TGCG-ACCT-CAGC-ATCG-ACCT-CAGC-spacer-NH₂ (SEQ. ID. No. 34) |
| Zip3 | 3-6-5-2-2-3 | CAGC-ACCT-GACC-ATCG-ATCG-CAGC-spacer-NH₂ (SEQ. ID. No. 35) |
| Zip5 | 5-6-1-2-4-3 | GACC-ACCT-TGCG-ATCG-GGTA-CAGC-spacer-NH₂ (SEQ. ID. No. 36) |
| Zip11 | 1-4-3-6-6-1 | TGCG-GGTA-CAGC-ACCT-ACCT-TGCG-spacer-NH₂ (SEQ. ID. No. 37) |
| Zip13 | 3-4-5-6-2-1 | CAGC-GGTA-GACC-ACCT-ATCG-TGCG-spacer-NH₂ (SEQ. ID. No. 38) |
| Zip15 | 5-4-1-6-4-1 | GACC-GGTA-TGCG-ACCT-GGTA-TGCG-spacer-NH₂ (SEQ. ID. No. 39) |
| Zip21 | 1-2-3-4-6-5 | TGCG-ATCG-CAGC-GGTA-ACCT-GACC-spacer-NH₂ (SEQ. ID. No. 40) |
| Zip23 | 3-2-5-4-2-5 | CAGC-ATCG-GACC-GGTA-ATCG-GACC-spacer-NH₂ (SEQ. ID. No. 41) |
| Zip25 | 5-2-1-4-4-5 | GACC-ATCG-TGCG-GGTA-GGTA-GACC-spacer-NH₂ (SEQ. ID. No. 42) |

*Order of tetramer oligonucleotide segments in the corresponding address sequence. Six tetramers, randomly chosen from a full set of thirty-six, are: 1 = TGCG; 2 = ATCG; 3 = CAGC; 4 = GGTA; 5 = GACC; 6 = ACCT. Closely related sequences, {Zip1,3, 5}, {Zip11, 13, 15} and {Zip21, 23, 25} differ at the first, third, and fifth tetramer positions, but are identical at the second, fourth, and sixth tetramer positions.
†spacer NH₂ = PO₄(CH₂CH₂O)₆PO₃(CH₂)₃NH₂

Each address sequence is a combination of six sets of tetramers such that the full length 24-mers have similar $T_m$ values ranging from 70° C.–82° C. (calculated using Oligo 6.0, Molecular Biology Insights, Inc., Plymouth Minn. and Cascade, Colo.). An initial group of thirty-six tetramers was developed where each tetramer differed from all others by at least two bases and was neither self-complementary nor complementary to any other tetramer (see Tables 1 and 13). Tetramers were combined such that each address sequence differs from all others by at least three alternating tetramer units (Table 13). This ensures that each address differs from all other addresses by at least 6 bases, thus preventing even the closest addressable array-specific portion of the oligonucleotide probe sets from cross-hybridizing ($T_m$ values of correct hybridizations are at least 24° C. higher than of any incorrect hybridization). The presence and type of each mutation is determined from the positions of those addresses at which signals are observed. Since different mutation-specific LDR probes can be appended to the same set of address complement sequences, this array is universal, and can be programmed to detect mutations in any gene.

Example 16
Array Preparation

Figure 34A:
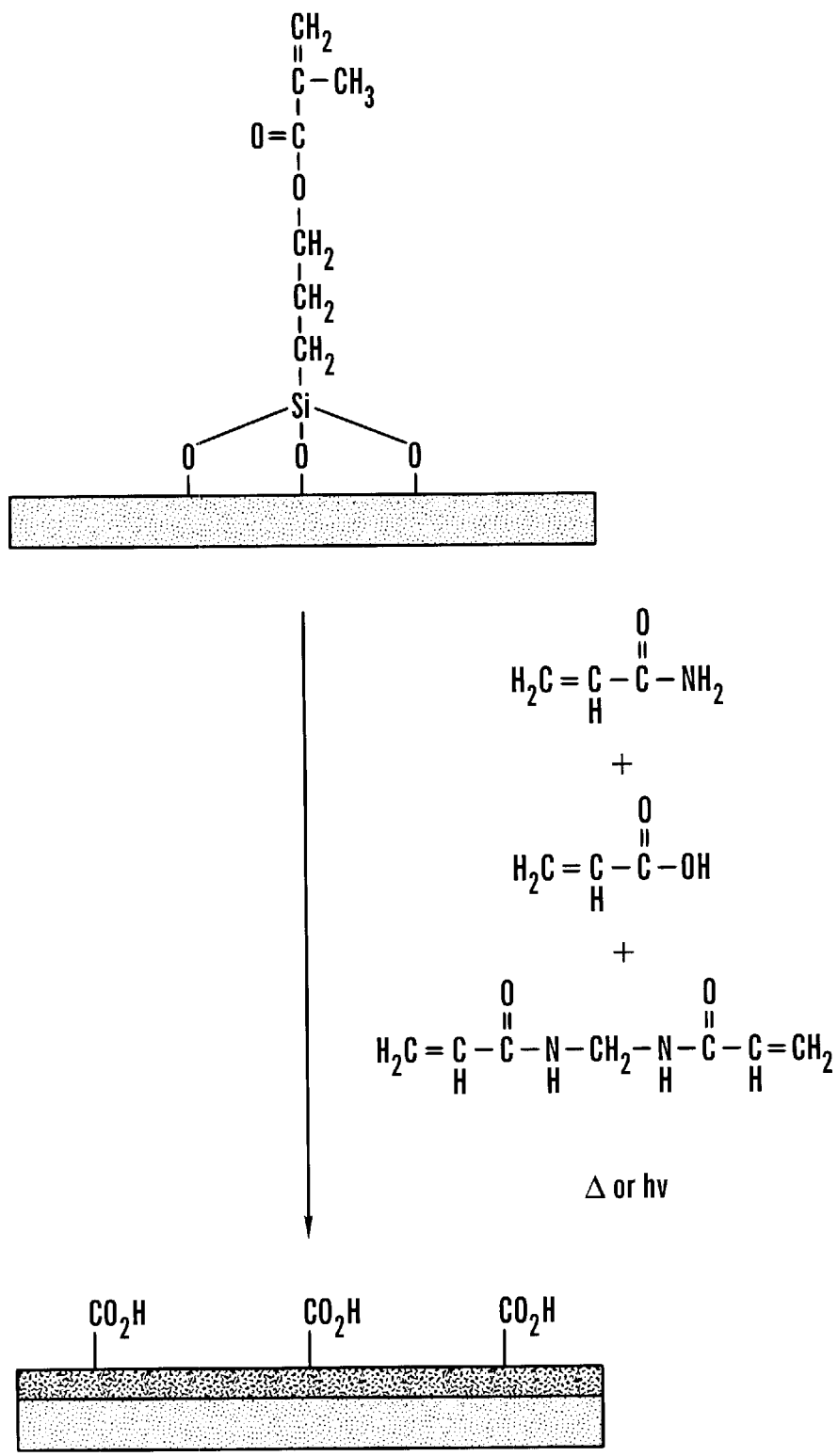
Figure 34B:
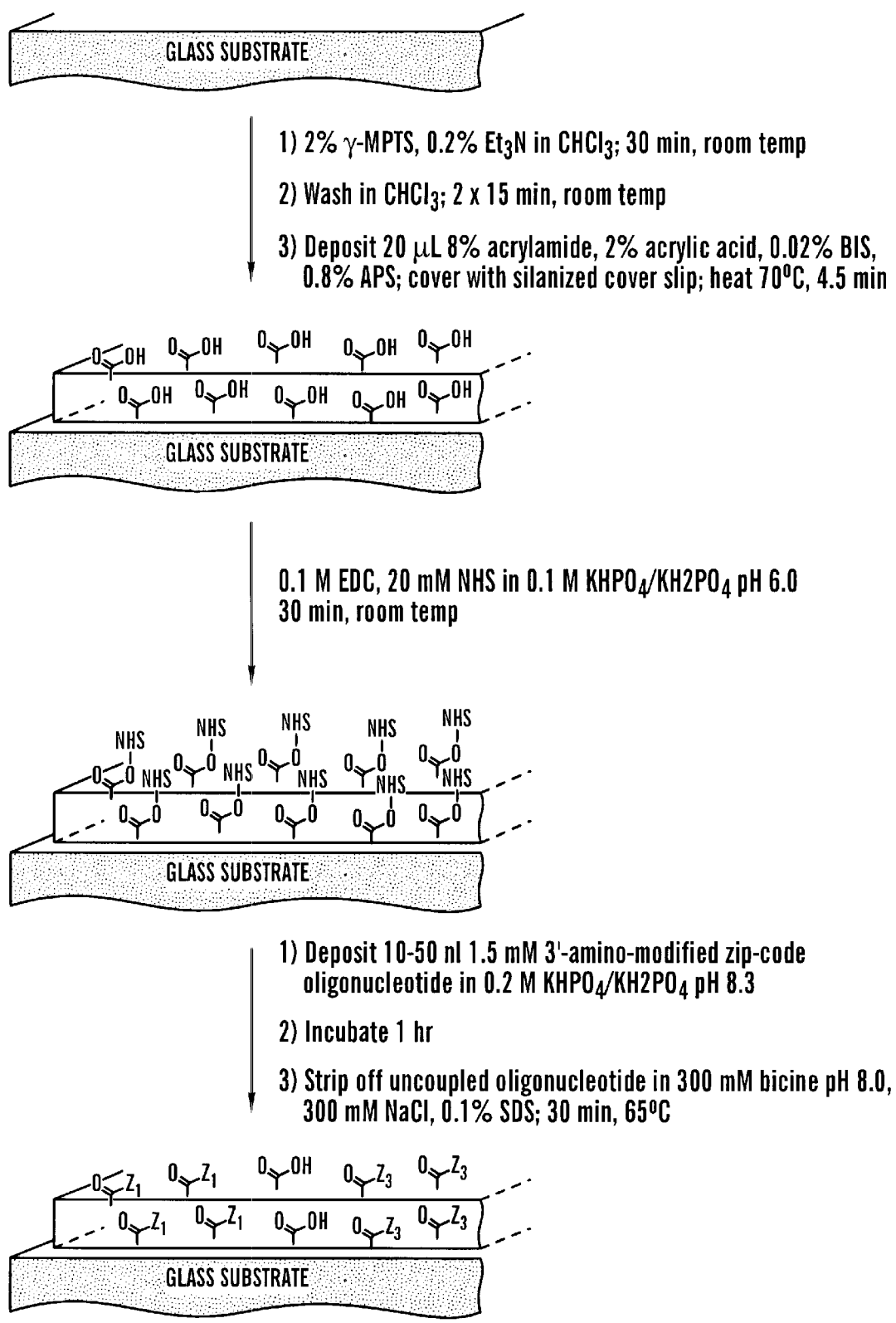
Figure 36:
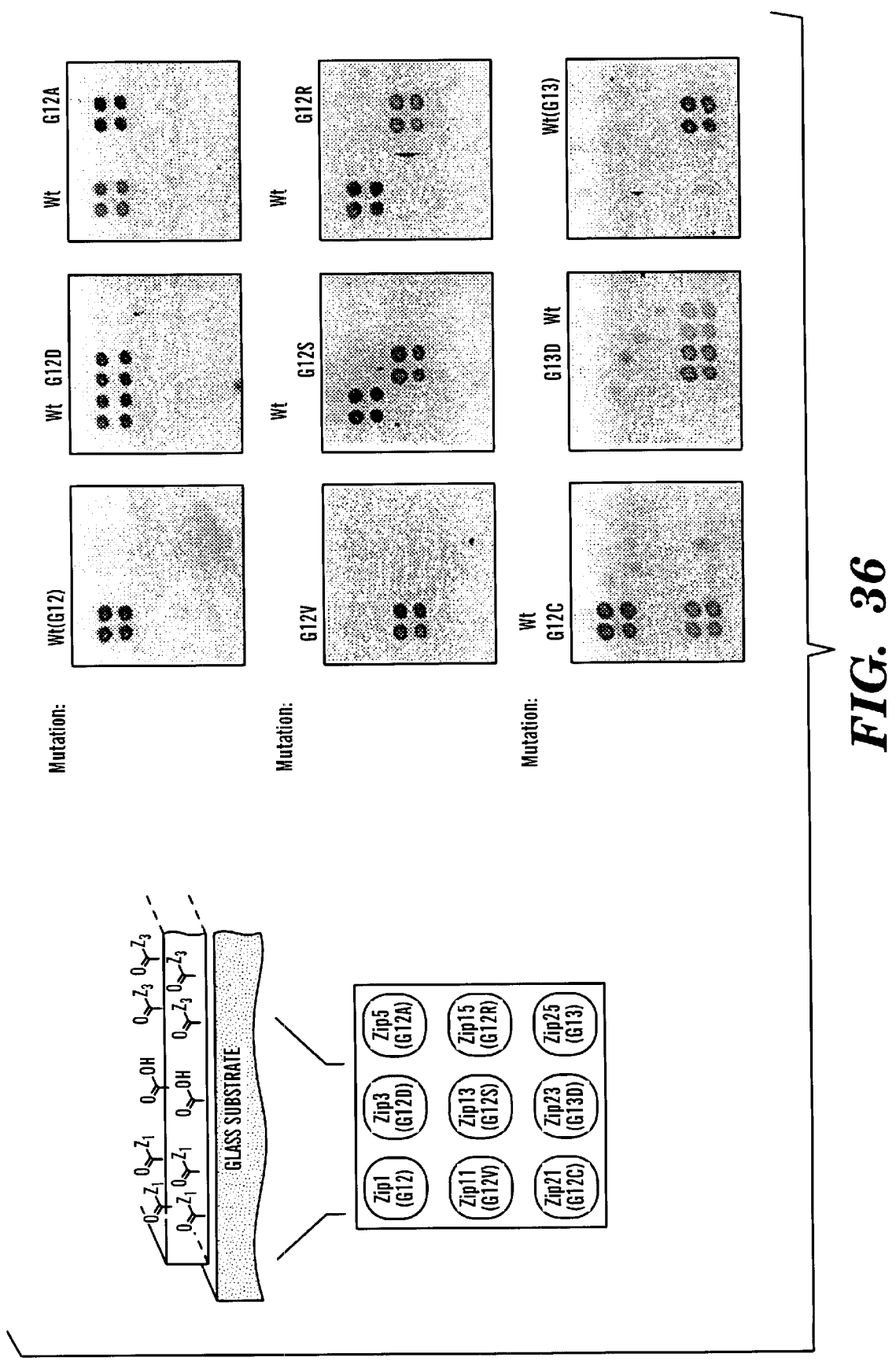
FIG. 36 shows the detection of K-ras mutations on a DNA array. This figure is a schematic representation of gel-based addressable array. Glass microscope slides treated with γ-methacryloxypropyltrimethoxy-silane are used as the substrate for the covalent attachment of an acrylamide/acrylic acid copolymer matrix. Amine-modified, capture oligonucleotides are coupled to N-hydroxysuccinimide activated surfaces at discrete locations. Each position in the 3×3 grid identifies an individual address (and corresponding K-ras mutation or wild-type sequence). This figure shows arrays hybridized with individual LDR reactions and fluorescent signal detected using a 2 sec exposure time. All nine arrays identified the correct mutant and/or wild-type for each tumor or cell line sample. The small spots seen in some of the panels, e.g., near the center of the panel containing the G13D mutant, are not incorrect hybridizations, but noise due to imperfections in the polymer.

Numerous types of two- and three-dimensional matrices were examined with respect to: (i) ease of preparation of the surface; (ii) oligonucleotide loading capacity; (iii) stability to conditions required for coupling of oligonucleotides, as well as for hybridization and washing; and (iv) compatibility with fluorescence detection. The preferred methodology to construct addressable arrays involves initial creation of a lightly crosslinked film of acrylamide/acrylic acid copolymer on a glass solid support; subsequently, the free carboxyl groups dispersed randomly throughout the polymeric surface are activated, and amine terminated capture oligonucleotides are added to form covalent amide linkages (FIGS.34A-B and 36A). The described coupling chemistry is rapid, straightforward, efficient, and amenable to both manual and robotic spotting. Both the activated surfaces and the surfaces with attached oligonucleotides are stable to long-term storage.

Example 17
Optimization of Hybridization Conditions

Figure 37:
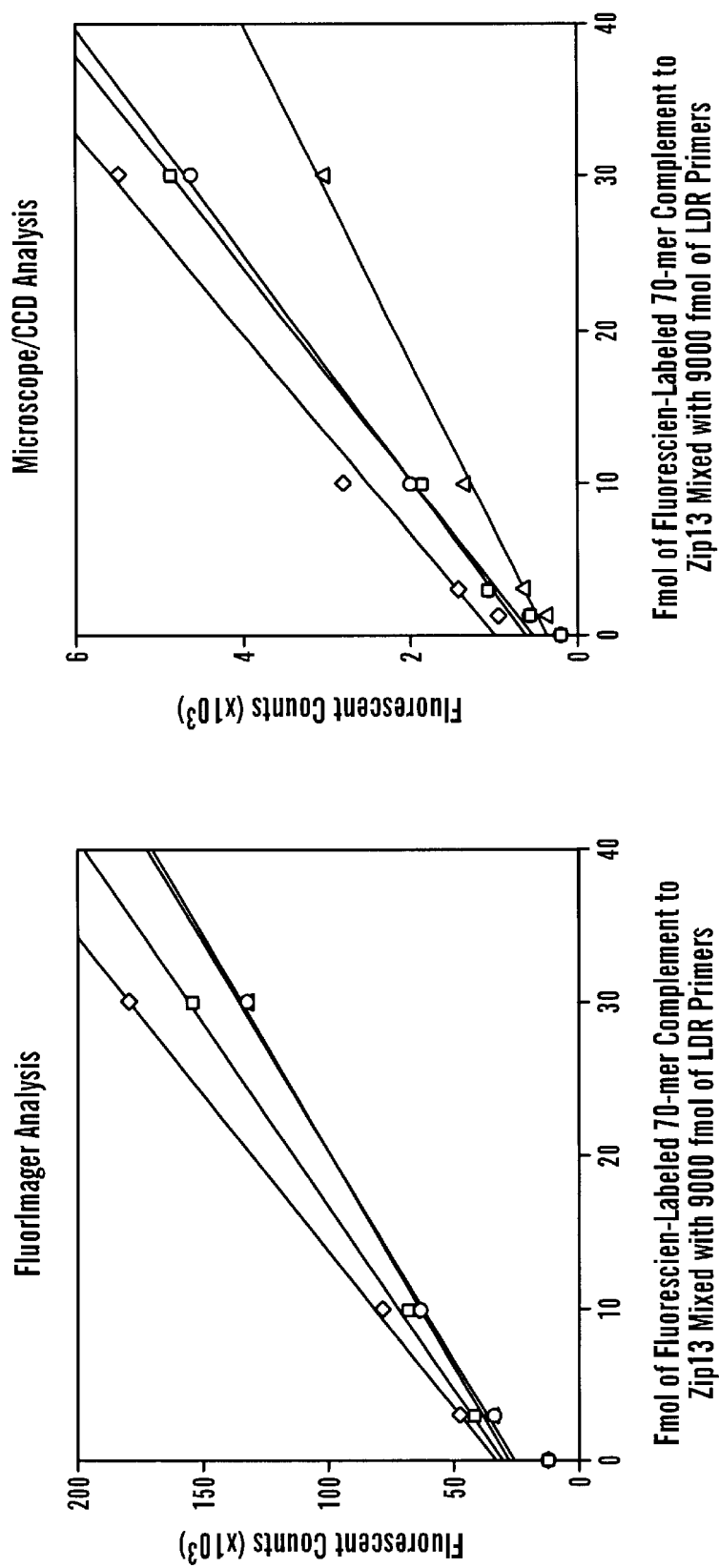
FIG. 37 shows the determination of addressable array capture sensitivity using two different detection instruments. Quadruplicate hybridizations were carried out as described infra. The graphs depict quantification of the amount of captured 70-mer complement using either a fluorimager (left) or an epifluorescence microscope/CCD (right). Each symbol represents hybridizations to an individual array.

Hybridizations of a fluorescently-labeled 70-mer probe onto model addressable arrays were measured as a function of buffer, metal cofactors, volume, pH, time, and the mechanics of mixing (Table 14). Even with closely related addresses, cross-hybridization was negligible or non-existent, with a signal-to-noise ratio of at least 50:1. These experiments suggest that different addresses undergo hybridization at approximately the same rate, i.e., the level of fluorescent signal is relatively uniform when normalized for the amount of oligonucleotide coupled per address. Magnesium ion was obligatory to achieve hybridization, and less than 1 fmol of probe could be detected in the presence of this divalent cation (Table 14; FIG. 37). The hybridization signal was doubled upon lowering the pH from 8.0 to 6.0, most likely due to masking of negative charges (hence reducing repulsive interactions with oligonucleotides) arising from uncoupled acrylic acid groups in the bulk polymer matrix. To confirm this hypothesis, the free carboxyl groups on arrays to which capture oligonucleotides had already been attached were capped with ethanolamine under standard coupling conditions. Hybridizations of the capped arrays at pH 8.0 gave results comparable to hybridizations at pH 6.0 of the same arrays without capping. Continuous mixing proved to be crucial for obtaining good hybridization, and studies of the time course led to 1 h at 65° C. being chosen as the standard. Reducing the hybridization volume improved the hybridization signal due to the relative increase in probe concentration. Further improvements may be achieved using specialized small volume hybridization chambers that allow for continuous mixing.

TABLE 14

Effect of hybridization conditions on hybridization signal.*

| Hybridization Buffer | Vol. (L) | Mixing† | Time (min) | Relative Signal |
|---|---|---|---|---|
| Buffer A | 55 | Inter. | 30 | 1 |
| Buffer A minus MgCl$_2$ | 55 | Inter. | 30 | <0.01 |
| Buffer A | 20 | Inter. | 30 | 2.5 |
| Buffer B | 55 | Inter. | 30 | 2 |
| Buffer B | 20 | Inter. | 30 | 3 |
| Buffer B | 55 | Cont. | 30 | 4 |
| Buffer B | 55 | Cont. | 60 | 8 |
| Buffer A + Capped Surface | 55 | Cont. | 60 | 8 |
| Buffer B minus MgCl$_2$ | 55 | Cont. | 60 | <0.01 |
| Buffer B | 55 | Cont. | 180 | 10 |

*Hybridizations were carried out with 1 pmol FAMcZip13-Prd and 3 × 3 manually spotted arrays. Buffers were - Buffer A: 300 mM bicine, pH 8.0–10 mM MgCl$_2$-0.1% SDS; Buffer B: 300 mM MES, pH 6.0–10 mM MgCl$_2$-0.1% SDS.
†Mixing was - Intermittent (Inter.): manual mixing of the sample once every ten min; Continuous (Cont.): mixing of sample at 20 rpm in a hybridization oven.

Example 18
Array Hybridization of K-ras LDR Products

PCR/LDR amplification coupled with detection on an addressable array was tested with the K-ras gene as a model system. Exon-specific PCR primers were used to selectively amplify K-ras DNA flanking codons 12 and 13. LDR probes were designed to detect the seven most common mutations found in the K-ras gene in colorectal cancer (FIG. 35C, Table 14). For example, the second position in codon 12, GGT, may mutate to GAT, coding for aspartate, which is detected by ligation of the allele-specific probe containing an addressable array-specific portion complement, cZip3, on its 5'-end, and a discriminating base, A, on its 3'-end to a fluorescently labeled common probe (FIG. 35C).

Figure 39:
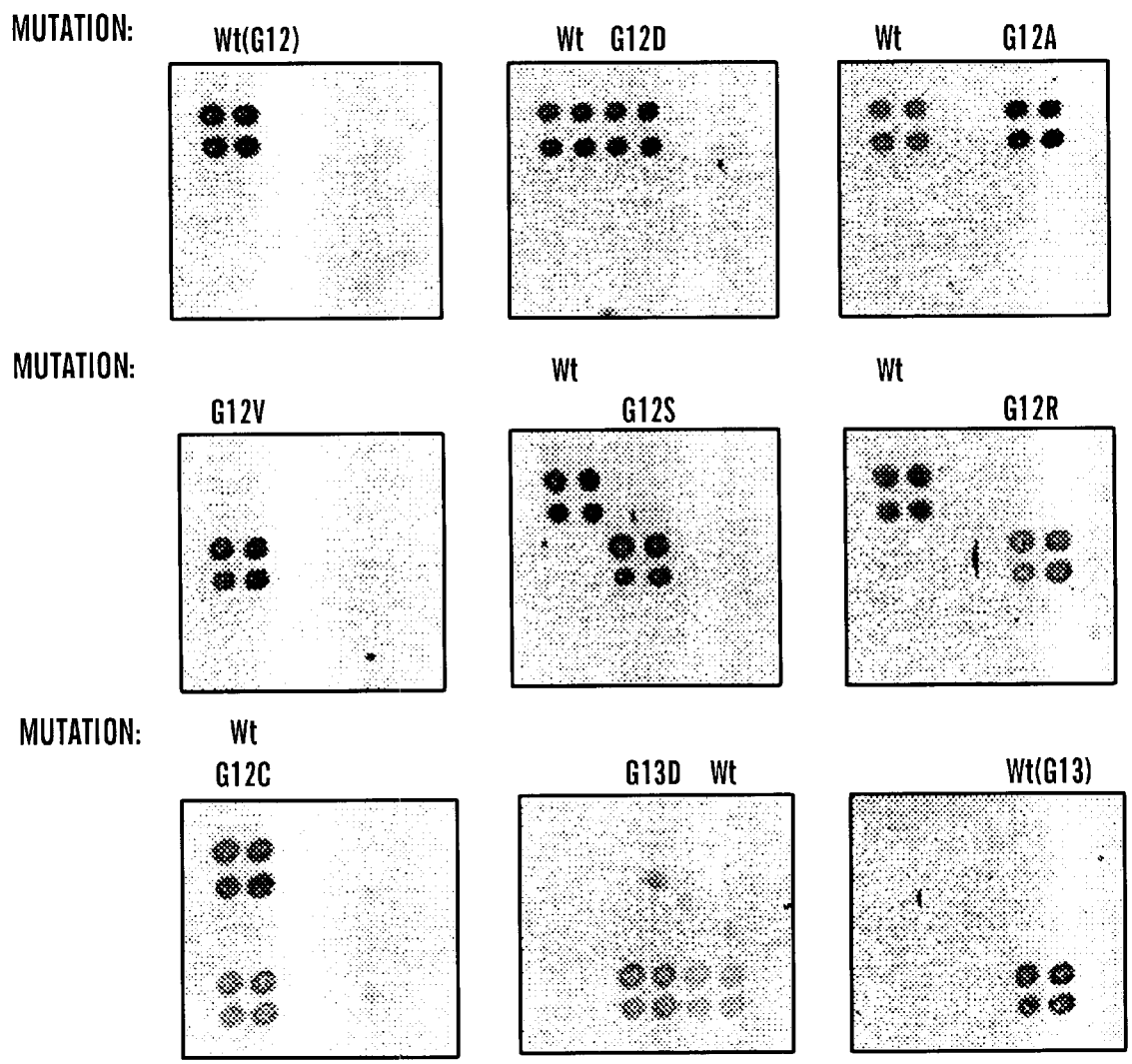
FIG. 39 shows the PCR/LDR detection of K-ras mutations using addressable array capture.
Figure 42:
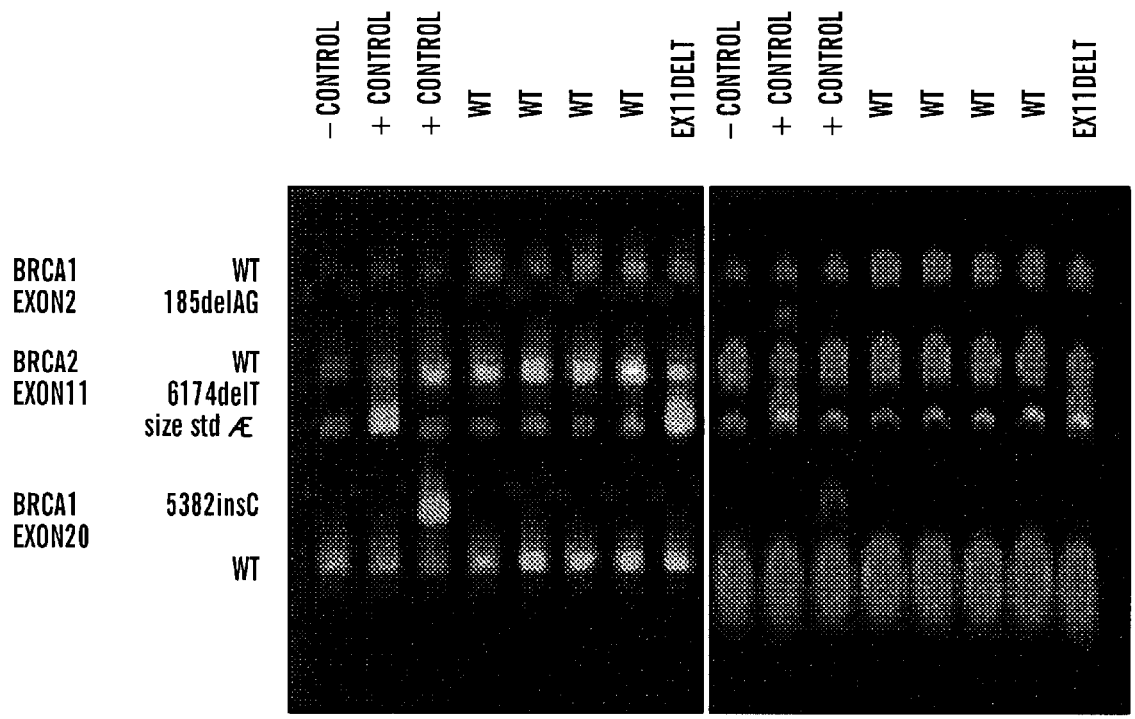
FIG. 42 shows the gel-based identification of 3 specific mutations in BRCA 1 and BRCA 2 genes detected by LDR.

PCR/LDR reactions were carried out on nine individual DNA samples derived from cell lines or paraffin-embedded tumors containing known K-ras mutations. An aliquot (2 μL) was taken from each reaction and electrophoresed on a sequencing apparatus to confirm that LDR was successful. Next, the different mutations were distinguished by hybridizing the LDR product mixtures on 3×3 addressable DNA arrays (each address was spotted in quadruplicate), and detecting the positions of fluorescent spots (FIG. 36B and FIG. 39). The wild-type samples, Wt(G12) and Wt(G13), each displayed four equal hybridization signals at Zip1 and Zip25, respectively, as expected. The mutant samples each displayed hybridization signals corresponding to the mutant, as well as for the wild-type DNA present in the cell line or tumor. The sole exception to this was the G12V sample, which was derived from a cell line (SW620) homozygous for the G12V K-ras allele. The experiment was repeated several times, using both manually and robotically spotted arrays, and LDR probes labeled with either fluorescein or Texas Red. False-positive or false-negative signals were not encountered in any of these experiments. A minimal amount of noise seen on the arrays can be attributed to dust, scratches, and/or small bubbles in the polymer. These flaws are readily recognized, because they are weak and sporadic, rather than reproducing the quadruplicate spotting pattern; such noise will be minimized with more stringent manufacturing conditions.

Example 19
Array Capture Sensitivity

After an LDR reaction, an excess of unligated discriminating probe competes with the successfully ligated and fluorescently-labeled LDR product for hybridization to the correct address on the array. To determine capture sensitivity, DNA arrays were hybridized in quadruplicate, under standard conditions, with from 100 amol (=1/90,000) to 30 (=1/300) fmol of a labeled synthetic 70-mer, FAMc-Zip13 -Prd (this simulates a full-length LDR product; see Materials and Methods for sequence), in the presence of a full set of K-ras LDR probes (combined total of 9,000 fmol of discriminating and common probes). Array analyses with a FluorImager (FIG. 37, left side) indicate that a signal-to-noise ratio of greater than 3:1 can be achieved when starting with a minimum of 3 fmol (=1/3,000) of FAMcZip13-Prd labeled probe in the presence of 4,500 fmol FAM-labeled LDR probes and 4,500 fmol of probes containing an addressable array-specific portion in the hybridization solution. Results using microscope/CCD instrumentation to quantify fluorescence were even more striking: a 3:1 signal-to-noise ratio can be maintained starting with 1 fmol (=1/9,000) labeled product (FIG. 37, right side), and it is expected that the limit can be extended to 100 amol after further optimization. For a given array, with fluorescence quantified by either instrument, the captured counts varied linearly with the amount of labeled FAMcZip13-Prd added. Rehybridization of the same probe, at the same concentration, to the same array, was reproducible within ±5%. Variations in fluorescent signal between arrays may reflect variations in the amount of capture oligonucleotide coupled, due to the inherent inaccuracies of manual spotting and/or variations in polymer uniformity.

Figure 38:
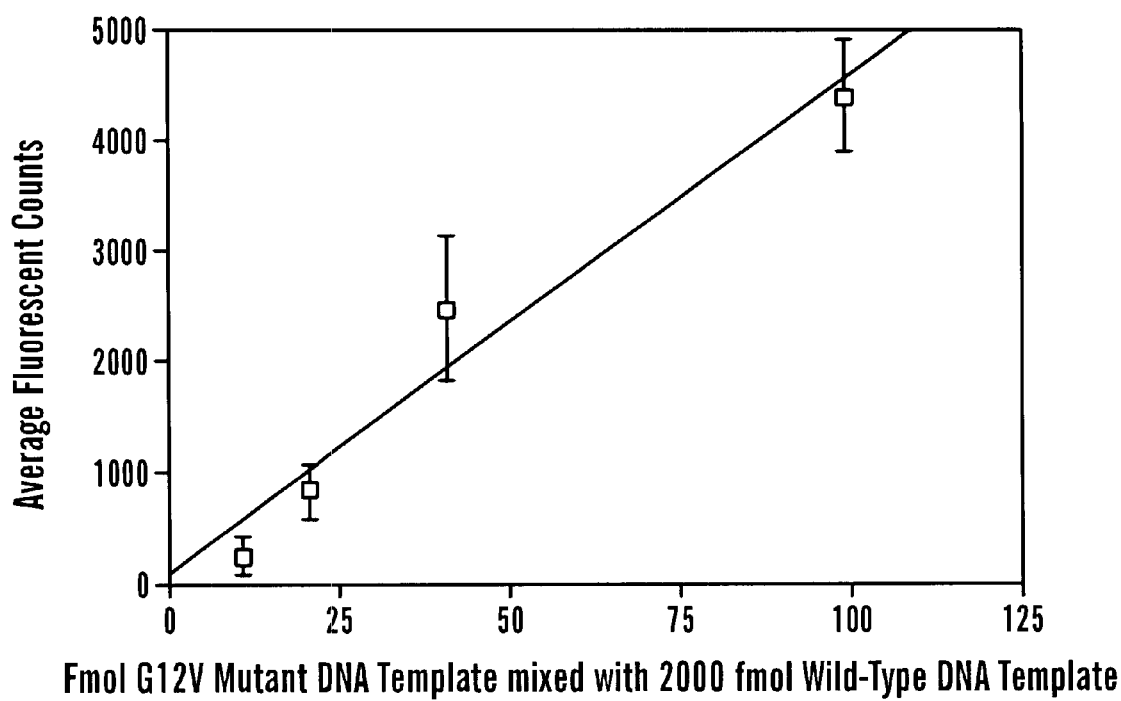
FIG. 38 shows the detection of minority K-ras mutant DNA in a majority of wild-type DNA using PCR/LDR with addressable array capture. DNA from cell line SW620, containing the G12V mutation, and DNA from normal lymphocytes were PCR amplified in exon 1 of the K-ras gene. Mixtures containing 10, 20, 40, or 100 fmol of G12V amplified fragment plus 2,000 fmol of PCR amplified wild-type fragment were prepared, and the presence of mutant DNA determined by LDR using probes specific for the G12V mutation (2,000 fmol each of discriminating and common primer). Images were collected by CCD using exposure times from 5 to 25 sec. Data was normalized by dividing fluorescent signal intensity by acquisition time. Each data point represents the average signal minus average background signal from hybridizations of four independent DNA arrays.

Example 20
Detection of Low Abundance Mutations by PCR/LDR/Array Hybridization To determine the limit of detection of low level mutations in wild-type DNA using PCR/LDR/array hybridization, a dilution series was set up and analyzed. PCR-amplified pure G12V DNA was diluted into wild-type K-ras DNA in ratios ranging from 1:20 to 1:500. Duplicate LDR reactions were carried out on 2,000 fmol total DNA, using a two-probe set consisting of 2,000 fmol each of the discriminating and common probes for the G12V mutation. It proved possible to quantify a positive hybridization signal at a dilution of 1:200 (FIG. 38); signal was distinguishable even at a dilution of 1:500, although noise levels due to dust or bubbles in the polymer prevented accurate quantification of the results in the latter case. A control of pure wild-type DNA showed no hybridization signal. These results indicate clearly that addressable array hybridization, when coupled with PCD/LDR, may detect polymorphisms present at less than 1% of the total DNA. These results are consistent with earlier work showing that PCR/LDR, using a 26-probe set and analyses based on gel electrophoreses of products, can detect any K-ras mutation in the presence of up to a 500-fold excess of wild-type, with a signal to noise ratio of at least 3:1.

Example 21
Polymerization of an Acrylamide-Acrylic Acid Polymer on the Surface of a Glass Slide Coated with γ-methacryloxypropyltrimethoxysilane 100 mg of bis-acryloylcystamine (Sigma) was added to 10 ml of 19% acrylamide—1% bisacrylamide (w/v) solution in water to produce a 1% (v/v) concentration of acrylic acid. The mixture was polymerized after adding 33 μl of 2% (w/v) ammonium persulfate (Biorad), and 1 μl of TEMED per 100 μl aliquot. 25 μl of the TEMED activated solution was applied to a γ-methacryloyloxypropyltrimethoxysilane coated glass slide, as described in Example 9, and allowed to polymerize under a glass coverslip coated with dichlorodimethylsilane, as described in Example 10.

Example 22
Attachment of Dye and Dye-labeled Oligonucleotide to an Acrylamide-Bisacrylamide-Acrylic Acid Copolymer A wedge gel composed of acrylamide-bisacrylamide-acrylic acid copolymer was prepared on a solid support, silanized with γ-methacryloxypropyltrimethoxysilane as described in Example 9. 33 μl of 2% ammonium persulfate was added to 1 ml of acrylamide-bisacrylamide-acrylic acid (9.5%: 0.5%: 1% w/v) solution. 1 μl of TEMED was added to a 100 μl aliquot and 20 μl of this mixture applied to the silanized solid support.

0.1 M Fluoresceinamine (Research Organics), 0.1 M Bodipy-FL-NHS (Molecular Probes) with 0.1 M putrescein, and an amino-derivatized fluorescein labeled oligonucleotide each in 0.1 M phosphate buffer pH 7 and 50 mM EDC (Pierce) were applied to the wedge gel. Coupling was allowed to proceed for 30 min in a humidified chamber at room temperature. Relative fluorescence units were measured on a Molecular Dynamics 595 Fluorimager with 488 nm excitation, 513 nm emission and 700 V potential on the photomultiplier tube. Table 15 shows relative fluorescence for dyes attached to the surface. In areas of comparable depth on the gel, Bodipy-FL had the highest RFU despite being linked to the matrix via putrescein, whereas fluorescein-amine had lower signal despite direct attachment to the matrix. Bodipy-FL is known to be less pH sensitive than fluorescein which may account for the nearly 5-fold RFU difference. The fluorescein labeled oligonucleotide coupled to the surface with over 5-fold lower RFUs than fluorescein. The lowest signal was observed with the fluorescein labeled amino-oligonucleotide. Dye appeared to more efficiently attach to the matrix than the oligonucleotide, likely because it can more readily penetrate the matrix. The ability of the dye to penetrate the matrix was shown, as in FIG. 40, through measuring relative fluorescence units (RFU) of the dye along the maximal depth gradient of a wedge gel. Fluorescein amine RFUs increase as the thickness of the gel increases.

TABLE 15

Quantification of relative fluorescence of dye and oligonucleotides attached to an acrylamide/acrylic acid copolymer

| Dye | attachment | integrated signal (total RFU*) | Standard Deviation |
|---|---|---|---|
| Bodipy-FL-NHS | putrescein | 3895940 | 701 |
| Fluorescein | amine | 825186 | 239 |
| Fluorescein | amino-oligonucleotide | 144178 | 326 |

*RFU = relative fluorescence units

Example 23

Amplification of BRCA1 and BRCA2 Exons for PCR/LDR Detection of Wild-type and Mutant Alleles Amplification from genomic DNA was performed starting with a 20 μl reaction mixture containing 50 ng of DNA, 2.5 mM of each dNTP, 1×TCK buffer (20 mM tricine, 200 μg/ml bovine serum albumin, and 50 mM potassium acetate), and 0.25 UTaq polymerase. To amplify BRCA1 exon 20 and BRCA2 exon 11, 4 pmol of each forward and reverse primer were used, with 8 pmol each of BRCA1 exon 2 primers. The tube was overlaid with mineral oil and preincubated for 1.5 min. at 94° C. A hot start was performed by adding 1 μl of polymerase diluted in 1×buffer to introduce the required units of polymerase. Each segment was amplified for 40 cycles. Each cycle consisted of a melting step 94° C. for 15 sec, and a combined anneal—extension step at 55° C. for 2 min. After the last cycle, the reactions were held at 55° C. for an additional 5 min. After PCR, the reactions were treated with proteinase K for 10 min at 70° C. and 15 min at 90° C.

The PCR products were used as templates for competitive LDR designed to distinguish wild-type from mutant alleles, detectable on a gel as bands of distinct size with different fluorescent dyes for each allele. The common probes are 5' phosphorylated and blocked (Bk) at the 3' terminus with a C3 spacer. Ligation reactions used 500 fmol of each discrimination probe and 750 fmol of each common probe, with 15 sec of denaturation at 94° C. and 2 min of ligation at 65° C. for 10 cycles. LDR products were separated by electrophoresis using a 10% acrylamide gel and detected on an ABI 373 fluorecence sequencer. ABI TAMRA-350 size standards were added to LDR samples.

LDR probes were redesigned to include addressable array-specific portions for capture to specific complement addresses on an array. Two approaches were developed. In the first, one address was on the array per LDR target with different dyes to identify each allele (Table 16).

TABLE 16

Probes for detecting 3 specific mutations in BRCA 1 and BRCA 2. Capture by hybridization to one address on the array per LDR target, and signal from different fluorescent dyes to discriminate between each allele.

| Mutation | Probe | Sequence |
|---|---|---|
| BRCA1 exon2 185delAG | common | Phos-TGTCCCATCTGGTAAGTCAGCACAAAC- |
| | BC1X2PZip1R | GCTGAGGTCGATGCTGAGGTGCGA-Block (SEQ. ID.No.43) |
| | wild-type BC1X2F1WT | Fluor-AACATTAATGCTATGCAGAAAATCTTAGAG (SEQ. ID. No. 44) |
| | mutant BC1X2TetMT | Tet-GTCATTAATGCTATGCAGAAAATCTTAG (SEQ. ID. No. 45) |
| BRCA1 exon20 5382insC | common | Phos-AGGACAGAAAGGTAAAGCTCCCTCC- |
| | BC1X20PZip3R | GCTGCGATCGATGGTCAGGTGCTG-Block (SEQ. ID. No. 46) |
| | wild-type BC1X20F1WT | Fluor-CAAAGCGAGCAAGAGAATCCC (SEQ. ID. No. 47) |
| | mutant BC1X20TetMT | Tet-ACAAAGCGAGCAAGAGAATCCCC (SEQ. ID. No. 48) |

TABLE 16-continued

Probes for detecting 3 specific mutations in BRCA 1 and BRCA 2. Capture by hybridization to one address on the array per LDR target, and signal from different fluorescent dyes to discriminate between each allele.

| Mutation | Probe | Sequence |
|---|---|---|
| BRCA2 exon11 6174delT | common | Phos-GGAAAATCTGTCCAGGTATCAGAT- |
| | BC2X11PZ5R | GCTGTACCCGATGCGAAGGTGGTC-Block (SEQ. ID. No. 49) |
| | wild-type BC2X11F1WT | Fluor-CAACTTGTGGGATTTTTAGCACAGCAAGT (SEQ. ID. No. 50) |
| | mutant BC2X11EMT | Tet-TACTTGTGGGATTTTTAGCACAGCAAG (SEQ. ID. No. 51) |

The probes hybridize to wild-type and mutant PCR products, but ligate only when both probes are perfectly matched with no gaps or overlaps (FIG. 41). Each addressable array-specific portion of the discriminating probe directs the LDR products to a specific address on the array. In the second approach, all LDR probes that discriminate between the presence and absence of a mutation have unique addressable array-specific portions which direct each LDR product to individual addresses (Table 17).

screened by LDR for mutations in parallel using both the single and double dye probe approaches. Both gels were loaded with LDR products from the same samples and both show comparable levels of each LDR product. The dual dye approach makes it easier to visually discriminate mutant versus wild-type product on the gel since the products may not fully separate on the gel. However, addressable array-specific portion hybridization on an array allows complete physical separation on the array and a single dye is sufficient

TABLE 17

Probes for detecting 3 specific mutations in BRCA 1 and BRCA 2. Capture on array by hybridization to one unique array address per Allele Signal derived from a single fluorescent dye.

| Mutation | Probe | Sequence |
|---|---|---|
| BRCA1 exon2 185delAG | common BC1X2PF | Phos-TGTCCCATCTGGTAAGTCAGCACAAAC-Fluor (SEQ ID No. 52) |
| | wild-type BC1X2WTZip2R | GCTGGCGACGATTACCAGGTCGAT-AACATTAATGCTATGCAGAAAATCTTAGAG (SEQ. ID. No. 53) |
| | mutant BC1X2MTZip4R | GCTGGCTGCGATAGGTAGGTTACC-GTCATTAATGCTATGCAGAAAATCTTAG (SEQ. ID. No. 54) |
| BRCAI exon20 5382insC | common BC1X20PF | Phos-AGGACAGAAAGGTAAAGCTCCCTCC-Fluor (SEQ. ID. No. 55) |
| | wild-type BC1X20WTZip12R | GCGAGCGAAGGTTACCTACCCGAT-CAAAGCGAGCAAGAGAATCCC (SEQ. ID. No. 56) |
| | mutant BC1X20MTZip13R | GCGACGATAGGTGGTCTACCGCTG-ACAAAGCGAGCAAGAGAATCCCC (SEQ. ID. No. 57) |
| BRCA2 exon11 6174delT | common BC2X11PF | Phos-GGAAAATCTGTCCAGGTATCAGAT-Fluor (SEQ. ID. No. 58) |
| | wild-type BC2X11WTZip14R | GCGAGCTGAGGTAGGTTACCTACC-CAACTTGTGGGATTUTAGCACAGCAAGT (SEQ. ID. No. 59) |
| | mutant BC2X11MTZ15R | GCGATACCAGGTGCGATACCGGTC-TACTTGTGGGATTTTTAGCACAGCAAG (SEQ. ID. No. 60) |

Figure 43:
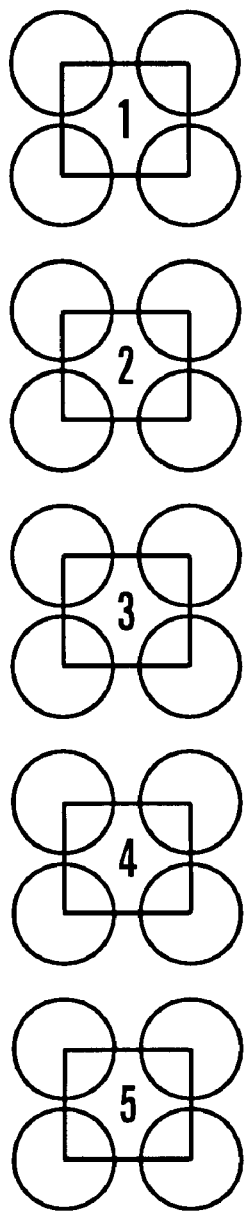
FIG. 43 shows oligonucleotides coupled on array addresses. Labels indicate oligonucleotides spotted as indicated in Table 16.
Figure 44:
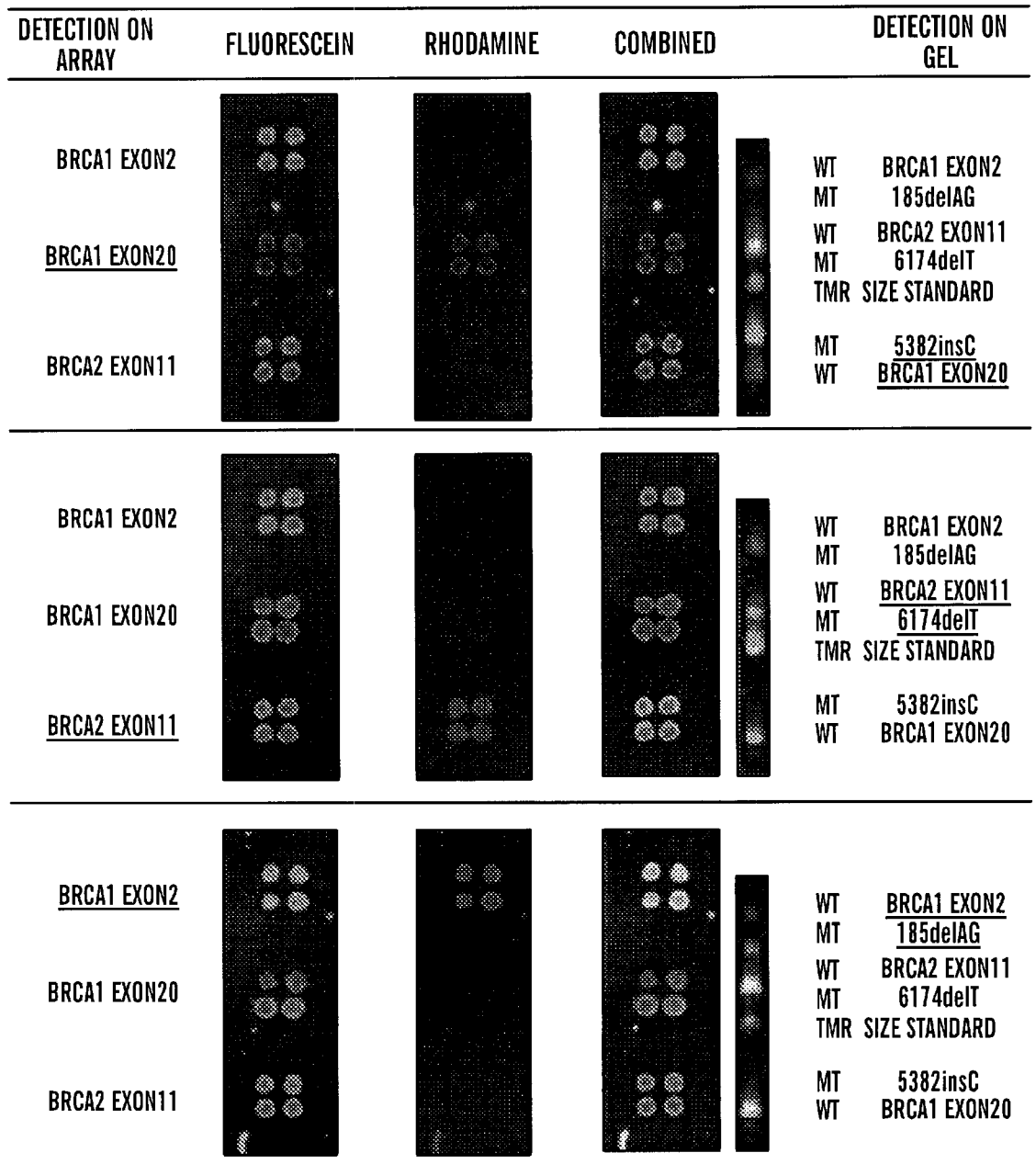
FIG. 44 shows the LDR detection of 3 specific mutations in BRCA 1 and BRCA 2 genes.

Only one dye is required (FIG. 43). These products can be separated by size on a gel to determine the presence or absence of mutations (FIG. 44). PCR products 10 were in this case. The array was made with multiple addresses (Table 18), four of each spotted as a group to test reproducibility (FIG. 44).

TABLE 18

Capture probes coupled to array.

| Probes | | Sequence | |
|---|---|---|---|
| 1 | AmSpZip1 | AminolinkerSpacerTCGCACCTCAGCATCGACCTCAGC | (SEQ: ID. No. 61) |
| 2 | AmSpZip2 | AminolinkerSpacerATCGACCTGGTAATCGTCGCCAGC | (SEQ. ID. No. 62) |
| 3 | AmSpZip3 | AminolinkerSpacerCAGCACCTGACCATCGATCGCAGC | (SEQ. ID. No. 63) |
| 4 | AmSpZip4 | AminolinkerSpacerGGTAACCTACCTATCGCAGCCAGC | (SEQ. ID. No. 64) |
| 5 | AmSpZip5 | AminolinkerSpacerGACCACCTTCGCATCGGGTACAGC | (SEQ. ID. No. 65) |

The array was imaged on an Olympus Provis AX70 microscope using 100 W mercury burner, fluorescein and rhodamine filter cubes and a Princeton Instruments TEK512/CCD camera.

The FAM labeled LDR products were imaged independently from the TET labeled LDR products. The 16-bit greyscale images were rescaled to more narrowly bracket the LDR signal before conversion to 8-bit greyscale. The 8-bit images were colored using Photoshop, where FAM (wild-type) was rendered green, and TET (mutant) was rendered red (FIG. 45). Finally these images were overlaid in register to produce the combined image where the presence of both wild-type and mutant alleles at an address appears yellow. Wild-type alleles were present in each sample, and only the addresses complementary to LDR product addressable array-specific portions had detectable signal. Thus, addressable array hybridization is very specific. The gel lanes for each sample hybridized on arrays are shown. The presence of a mutation in each sample is indicated by underlining the corresponding description of the array address and the gel band. In each case, the array reproduced the result of the gel. The dual label approach is capable of identifying the presence of wild-type and mutant alleles on the same array address, and this method can identify homozygous or heterozygous individuals

Example 24
Array Preparation and Use in Hybridization Reactions

When compared to monolayer coverage of a support, a polymer coating on a glass microscope slide offers increased coupling capacity of the capture probes. Toward this end, a support was prepared with a layer of neutral polymer up to 20 microns thick. The polymer was an acrylamide based material doped with glycerol monomethacrylate. When oxidized, the vicinol diols of the glycerol monomethacrylate were converted to aldehydes which served as anchor points for the amine-terminated oligonucleotide capture probes.

To anchor the polymer to the surface, the glass is first silanized with 3-(trimethoxysilyl)propyl methacrylate according to the procedure of S. Savard, et al., "Hydrolysis and Condensation of Silanes in Aqueous Solutions," *Polym Compos* 5:242–249 (1984), which is hereby incorporated by reference. A dilute aqueous HCl solution, pH 2–4, of 3-(trimethoxysilyl)propyl methacrylate (0.04 M) is vigorously stirred at 25° C. for 30 minutes. Clean 3×1' microscope slides (prepared according to Example 8) are incubated with occasional agitation in this solution for 30 minutes at 25° C., rinsed in deionized water, blown dry with nitrogen, and used within 24 hours.

One and one-thousandth inch stainless steel shims are positioned on three sides between the methacrylate treated slide and a second microscope slide which has been rendered hydrophobic (10% v/v dichlorodimethylsilane in toluene). E. N. Timofeev, et al., "Regioselective Immobilization of Short Oligonucleotides to Acrylic Copolymer Gels," *Nucleic Acids Res.* 24:3142–3148 (1996), which is hereby incorporated by reference. The three edges supported by the shims are held in place with clamps leaving a one 1 inch edge of the microscope slide open. The cavity thus formed is filled with a polymerizable solution containing N,N-dimethylacrylamide (0.9 M), glycerol monomethacrylate (0.1 M) (Polysciences, Inc. Warrington, Pa.), N,N-methylene-bisacrylamide crosslinker (0.0027 M), with N,N,N'N'-tetramethylethylenediamine (0.2% v/v) and freshly prepared 10% ammonium persulfate (2% v/v) to initiate polymerization. The polymerization proceed for 30 min at 25° C., and the "sandwich" is disassembled. The polymeric film is rinsed in deionized water, allowed to dry, and stored at 4° C. until further use.

As practiced in the aforementioned reference, a conventional protocol is used, employing oxidation with NaIO4 to generate an aldehyde in its gel form, a custom designed precursor copolymerized with N,N-dimethylacrylamide. The aldehyde in the present invention is generated by treatment of the vicinol diol of glycerol monomethacrylate with NaIO4 (0.1 M, 25° C., 1 hour). The aldehyde containing matrix is soaked in deionized water (1 hour, 25° C.). The slides are removed from the bath, and excess water is blown off the hydrated surface with a stream of nitrogen. The polymer is allowed to dry (30 minutes, 25° C.). Using a 0.5 $\mu$l capacity syringe, 0.1 $\mu$l of a fluorescently labeled 24-mer capture oligonucleotide probe (500 $\mu$M in 0.2 M sodium acetate buffer at pH ~5) containing a primary, terminal amine is deposited onto the aldehydic surface. One-tenth microliter of sodium cyanoborohydride (0.1 M) is deposited directly on top of the liquid containing the address. The reductive amination is allowed to proceed for 24 hours in a humidity chamber (25° C.). After the coupling reaction, the matrix is soaked in bicine buffer (300 mM, pH 8), containing 300 mM NaCl and 0.1% sodium dodecylsulfate for 30 min at 65° C. The slides are rinsed in deionized water, blown dry with nitrogen and stored in a desiccator.

Hybridization are run according to Example 14.

Fluorescent images are obtained with a Spot Camera from Universal Imaging using a mercury vapor lamp at a magnification of 4×. The exposure time for a rhodamine labeled complement is 10 seconds. Metamorph is used to quantify the amount of light signal above background. The original image is reduced to 50% and a circle with a 400 pixel diameter is integrated.

Table 19 shows capture performance of slides prepared in the above manner.

TABLE 19

Fluorescent Quantification of captured probe

| | Probe | Fluorescent counts at capture oligonucleotide 11 | Fluorescent counts at capture oligonucleotide 13 |
|---|---|---|---|
| Slide 1 | 11 | $3.92 \times 10^6$ | no detectable reading |
| Slide 2 | 11 | $2.04 \times 10^6$ | no detectable reading |
| Slide 3 | 11 | $2.55 \times 10^6$ | no detectable reading |
| Slide 1 | 13 | no detectable reading | $5.86 \times 10^6$ |
| Slide 2 | 13 | no detectable reading | $2.66 \times 10^6$ |
| Slide 3 | 13 | no detectable reading | $7.25 \times 10^6$ |

The present approach to mutation detection has three orthogonal components: (i) primary PCR amplification; (ii) solution-phase LDR detection; and (iii) solid-phase hybridization capture. Therefore, background signal from each step can be minimized, and, consequently, the overall sensitivity and accuracy of the present method are significantly enhanced over those provided by other strategies. For example, "sequencing by hybridization" methods require: (i) multiple rounds of PCR or PCR/T7 transcription; (ii) processing of PCR amplified products to fragment them or render them single-stranded; and (iii) lengthy hybridization periods (10 h or more) which limit their throughput (Guo, et al., *Nucleic Acids Res.,* 22:5456–5465 (1994); Hacia, et. al., *Nat. Genet.* 14441–447 (1996); Chee, et al., *Science,* 274:610–614 (1996); Cronin, et al., *Human Mutation.* 7:244–255 (1996); Wang, et al., *Science,* 280:1077–1082 (1998); Schena, et al., *Proc. Natl. Acad. Sci. USA,* 93:10614–10619 (1996); and Shalon, et al., *Genome Res.,* 6:639–645 (1996), which are hereby incorporated by reference). Additionally, since the immobilized probes on these arrays have a wide range of $T_m$'s, it is necessary to perform the hybridizations at temperatures from 0° C. to 44° C. The result is increased background noise and false signals due to mismatch hybridization and non-specific binding, for example on small insertions and deletions in repeat sequences (Hacia, et. al., *Nat. Genet.,* 14441–447 (1996); Cronin, et al., *Human Mutation.* 7:244–255 (1996); Wang, et al., *Science,* 280:1077–1082 (1998); and Southern, E. M., *Trends in Genet.,* 12:110–115 (1996), which are hereby incorporated by reference). In contrast, the approach of the present invention allows multiplexed PCR in a single reaction (Belgrader, et al., *Genome Sci. Technol.,* 1:77–87 (1996), which is hereby incorporated by reference), does not require an additional step to convert product into single-stranded form, and can readily distinguish all point mutations including slippage in repeat sequences (Day, et al., *Genomics,* 29:152–162 (1995), which is hereby incorporated by reference). Alternative DNA arrays suffer from differential hybridization efficiencies due to either sequence variation or to the amount of target present in the sample. By using the present approach of designing divergent address sequences with similar thermodynamic properties, hybridizations can be carried out at 65° C., resulting in a more stringent and rapid hybridization. The decoupling of the hybridization step from the mutation detection stage offers the prospect of quantification of LDR products, as has already been achieved using gel-based LDR detection.

Arrays spotted on polymer surfaces provide substantial improvements in signal capture, as compared with arrays spotted or synthesized in situ directly on glass surfaces (Drobyshev, et al., *Gene,* 188:45–52 (1997); Yershov, et al., *Proc. Natl. Acad. Sci. USA,* 93:4913–4918 (1996); and Parinov, et al., *Nucleic Acids Res.,* 24:2998–3004 (1996), which are hereby incorporated by reference). However, the polymers described by others are limited to using 8- to 10-mer addresses while the polymeric surface of the present invention readily allows 24-mer capture oligonucleotides to penetrate and couple covalently. Moreover, LDR products of length 60 to 75 nucleotide bases are also found to penetrate and subsequently hybridize to the correct address. As additional advantages, the polymer gives little or no background fluorescence and does not exhibit non-specific binding of fluorescently-labeled oligonucleotides. Finally, capture oligonucleotides spotted and coupled covalently at a discrete address do not "bleed over" to neighboring spots, hence obviating the need to physically segregate sites, e.g., by cutting gel pads.

The present invention relates to a strategy for high-throughput mutation detection which differs substantially from other array-based detection systems presented previously in the literature. In concert with a polymerase chain reaction/ligase detection reaction (PCR/LDR) assay carried out in solution, the array of the present invention allows for accurate detection of single base mutations, whether inherited and present as 50% of the sequence for that gene, or sporadic and present at 1% or less of the wild-type sequence. This sensitivity is achieved, because thermostable DNA ligase provides the specificity of mutation discrimination, while the divergent addressable array-specific portions of the LDR probes guide each LDR product to a designated address on the DNA array. Since the address sequences remain constant and their complements can be appended to any set of LDR probes, the addressable arrays of the present invention are universal. Thus, a single array design can be programmed to detect a wide range of genetic mutations.

Robust methods for the rapid detection of mutations at numerous potential sites in multiple genes hold great promise to improve the diagnosis and treatment of cancer patients. Noninvasive tests for mutational analysis of shed cells in saliva, sputum, urine, and stool could significantly simplify and improve the surveillance of high risk populations, reduce the cost and discomfort of endoscopic testing, and lead to more effective diagnosis of cancer in its early, curable stage. Although the feasibility of detecting shed mutations has been demonstrated clearly in patients with known and genetically characterized tumors (Sidransky, et al., *Science,* 256:102–105 (1992), Nollau, et al., *Int. J. Cancer,* 66:332–336 (1996); Calas, et al., *Cancer Res.* 54:3568–73 (1994); Hasegawa, et al., *Oncogene* 10:1413–16 (1995); and Wu et al., *Early Detection of Cancer Molecular Markers* (Lippman, et al. ed.) (1994), which are hereby incorporated by reference), effective presymptomatic screening will require that a myriad of potential low frequency mutations be identified with minimal false-positive and false-negative signals. Furthermore, the integration of technologies for determining the genetic changes within a tumor with clinical information about the likelihood of response to therapy could radically alter how patients with more advanced tumors are selected for treatment. Identification and validation of reliable genetic markers will require that many candidate genes be tested in large scale clinical trials. While costly microfabricated chips can be manufactured with over 100,000 addresses, none of them have demonstrated a capability to detect low abundance mutations (Hacia, et. al., *Nat. Genet.* 14441–447 (1996); Chee, et al., *Science,* 274:610–614 (1996); Kozal, et al., *Nat. Med.,* 2:753–759 (1996); and Wang, et al., *Science,* 280:1077–1082 (1998), which are hereby incorporated by reference), as required to accurately score mutation profiles in such clinical trials. The universal addressable array approach of the present invention has the potential to allow rapid and reliable identification of low abundance mutations in multiple codons in numerous genes, as well as quantification of multiple gene deletions and amplifications associated with tumor progression. In addition, for MRNA expression profiling, the LDR-universal array can differentiate highly homologous genes, such as K-, N-, and H-ras. Moreover, as new therapies targeted to specific genes or specific mutant proteins are developed, the importance of rapid and accurate high-throughput genetic testing will undoubtedly increase.

Although the invention has been described in detail for the purpose of illustration, it is understood that such details are solely for that purpose and variations can be made therein by those skilled in the art without departing from the spirit and scope of the invention which is defined by the following claims.

What is claimed:

1. A method for identifying one or more of a plurality of sequences differing by one or more single-base changes, insertions, deletions, or translocations in a plurality of target nucleotide sequences comprising:

providing a sample potentially containing one or more target nucleotide sequences with a plurality of sequence differences;

providing a plurality of oligonucleotide probe sets, each set characterized by (a) a first oligonucleotide probe, having a target-specific portion and an addressable array-specific portion, and (b) a second oligonucleotide probe, having a target-specific portion and a detectable reporter label, wherein the oligonucleotide probes in a particular set are suitable for ligation together when hybridized adjacent to one another on a corresponding target nucleotide sequence, but have a mismatch which interferes with such ligation when hybridized to any other nucleotide sequence present in the sample;

providing a ligase, blending the sample, the plurality of oligonucleotide probe sets, and the ligase to form a mixture;

subjecting the mixture to one or more ligase detection reaction cycles comprising a denaturation treatment, wherein any hybridized oligonucleotides are separated from the target nucleotide sequences, and a hybridization treatment, wherein the oligonucleotide probe sets hybridize at adjacent positions in a base-specific manner to their respective target nucleotide sequences, if present in the sample, and ligate to one another to form a ligated product sequence containing (a) the addressable array-specific portion, (b) the target-specific portions connected together, and (c) the detectable reporter label, and, wherein the oligonucleotide probe sets may hybridize to nucleotide sequences in the sample other than their respective target nucleotide sequences but do not ligate together due to a presence of one or more mismatches and individually separate during the denaturation treatment;

providing a solid support with different capture oligonucleotides immobilized at particular sites, wherein the capture oligonucleotides have nucleotide sequences complementary to the addressable array-specific portions and form an addressable array;

contacting the mixture, after said subjecting the mixture to one or more ligase detection reaction cycles, with the solid support under conditions effective to mask negative charges and to hybridize the addressable array-specific portions to the capture oligonucleotides in a base-specific manner, thereby capturing the addressable array-specific portions on the solid support at the site with the complementary capture oligonucleotide; and detecting the reporter labels of ligated product sequences captured to the solid support at particular sites, thereby indicating the presence of one or more target nucleotide sequences in the sample.

2. A method according to claim 1, wherein the oligonucleotide probes in a set are suitable for ligation together at a ligation junction when hybridized adjacent to one another on a corresponding target nucleotide sequence due to perfect complementarity at the ligation junction, but, when the oligonucleotide probes in the set are hybridized to any other nucleotide sequence present in the sample, have a mismatch at a base at the ligation junction which interferes with such ligation.

3. A method according to claim 1, wherein the mismatch is at the 3' base at the ligation junction.

4. A method according to claim 1, wherein the oligonucleotide probes in a set are suitable for ligation together at a ligation junction when hybridized adjacent to one another on a corresponding target nucleotide sequence due to perfect complementarity at the ligation junction, but, when the oligonucleotide probes in the set are hybridized to any other nucleotide sequence present in the sample, there is a mismatch at a base adjacent to a base at the ligation junction which interferes with such ligation.

5. A method according to claim 4, wherein the mismatch is at the base adjacent to the 3' base at the ligation junction.

6. A method according to claim 1, wherein the sample potentially contains unknown amounts of one or more of a plurality of target sequences with a plurality of sequence differences, said method further comprising:

quantifying, after said detecting, the amount of the target nucleotide sequences in the sample by comparing the amount of captured ligated product sequences generated from the sample with a calibration curve of captured ligated product sequences generated from samples with known amounts of the target nucleotide sequence.

7. A method according to claim 1, wherein the sample potentially contains unknown amounts of one or more of a plurality of target nucleotide sequences with a plurality of sequence differences, said method further comprising:

providing a known amount of one or more marker target nucleotide sequences;

providing a plurality of marker-specific oligonucleotide probe sets, each set characterized by (a) a first oligonucleotide probe, having a target-specific portion complementary to the marker target nucleotide sequence and an addressable array-specific portion complementary to capture oligonucleotides on the solid support, and (b) a second oligonucleotide probe, having a target-specific portion complementary to the marker target nucleotide sequence and a detectable reporter label, wherein the oligonucleotide probes in a particular marker-specific oligonucleotide set are suitable for ligation together when hybridized adjacent to one another on a corresponding marker target nucleotide sequence, but, when hybridize to any other nucleotide sequence present in the sample or added marker sequences, there is a mismatch which interferes with such ligation, wherein said blending comprises blending the sample, the marker target nucleotide sequences, the plurality of oligonucleotide probe sets, the plurality of marker-specific oligonucleotide probe sets, and the ligase to form a mixture;

detecting the reporter labels of the ligated marker-specific oligonucleotide sets captured on the solid support at particular sites, thereby indicating the presence of one or more marker target nucleotide sequences in the sample; and quantifying the amount of target nucleotide sequences in the sample by comparing the amount of captured ligated product generated from the known amount of marker target nucleotide sequences with the amount of captured other ligated product.

8. A method according to claim 7, wherein the one or more marker target nucleotide sequences differ from the target nucleotide sequences in the sample at one or more single nucleotide positions.

9. A method according to claim 8, wherein the oligonucleotide probe sets and the marker-specific oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, the first oligonucleotide probes have a common target-specific portion, and the second oligonucleotide probes have a differing target-specific portion which hybridize to a given allele or a marker nucleotide sequence in a base-specific manner.

10. A method according to claim 8, wherein the oligonucleotide probe sets and the marker-specific oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, the second oligonucleotide probes have a common target-specific portion and the first oligonucleotide probe have differing target-specific portions, which hybridize to a given allele or a marker nucleotide sequence in a base-specific manner.

11. A method according to claim 1, wherein the sample potentially contains unknown amounts of two or more of a plurality of target nucleotide sequences with a plurality of sequence differences, said method further comprising:

quantifying, after said detecting, the relative amount of each of the plurality of target nucleotide sequences in the sample by comparing the relative amount of captured ligated product sequences generated by each of the plurality of target sequences within the sample, thereby providing a quantitative measure of the relative level of two or more target nucleotide sequences in the sample.

12. A method according to claim 1, wherein multiple allele differences at two or more adjacent nucleotide positions, or at nucleotide positions which require overlapping oligonucleotide probe sets, in a single target nucleotide sequence or multiple allele differences at two or more adjacent nucleotide positions, or at nucleotide positions which require overlapping oligonucleotide probe sets, in multiple target nucleotide sequences are distinguished with oligonucleotide probe sets having oligonucleotide probes with target-specific portions which overlap.

13. A method according to claim 1, wherein the target-specific portions of the oligonucleotide probe sets have substantially the same melting temperature so that they hybridize to target nucleotide sequences under similar hybridization conditions.

14. A method according to claim 1, wherein multiple allele differences at one or more nucleotide position in a single target nucleotide sequence or multiple allele differences at one or more positions in multiple target nucleotide sequences are distinguished, the oligonucleotide probe sets forming a plurality of oligonucleotide probe groups, each group comprised of one or more oligonucleotide probe sets designed for distinguishing multiple allele differences at a single nucleotide position, wherein, in the oligonucleotide probes of each group, the second oligonucleotide probes have a common target-specific portion and the first oligonucleotide probes have differing target-specific portions which hybridize to a given allele in a base-specific manner, wherein, in said detecting, the labels of ligated product sequences of each group, captured on the solid support at different sites, are detected, thereby indicating a presence, in the sample of one or more allele at one or more nucleotide position in one or more target nucleotide sequences.

15. A method according to claim 14, wherein the oligonucleotide probes in a given set are suitable for ligation together at a ligation junction when hybridized adjacent to one another on a corresponding target nucleotide sequence due to perfect complementarity at the ligation junction, but, when hybridized to any other nucleotide sequence present in the sample, the first oligonucleotide probe has a mismatch at a base at the ligation junction which interferes with such ligation.

16. A method according to claim 14, where multiple allele differences at two or more adjacent nucleotide positions, or at nucleotide positions which require overlapping oligonucleotide probe sets, in a single target nucleotide sequence or multiple allele differences at two or more adjacent nucleotide positions, or at nucleotide positions which require overlapping oligonucleotide probe sets, in multiple target nucleotide sequences are distinguished with oligonucleotide probe groups having oligonucleotide probes with target-specific portions which overlap.

17. A method according to claim 16, wherein the oligonucleotide probes in a set are suitable for ligation together at a ligation junction when hybridized adjacent to one another on a corresponding target nucleotide sequence due to perfect complementarity at the ligation junction, but, when the oligonucleotide probes in the set are hybridized to any other nucleotide sequence present in the sample, there is a mismatch at a base at the ligation junction which interferes with such ligation.

18. A method according to claim 1, wherein multiple allele differences consisting of insertions, deletions, microsatellite repeats, translocations, or other DNA rearrangements at one or more nucleotide positions which require overlapping oligonucleotide probe sets in a single target nucleotide sequence or multiple allele differences consisting of insertions, deletions, microsatellite repeats, translocations, or other DNA rearrangements at one or more nucleotide positions which require overlapping oligonucleotide probe sets in multiple target nucleotide sequences are distinguished, the oligonucleotide probe sets forming a plurality of oligonucleotide probe groups, each group comprised of one or more oligonucleotide probe sets designed for distinguishing multiple allele differences selected from the group consisting of insertions, deletions, microsatellite repeats, translocations, and other DNA rearrangements at one or more nucleotide positions which require overlapping oligonucleotide probe sets, wherein, in the oligonucleotide probe sets of each group, the second oligonucleotide probes have a common target-specific portion and the first oligonucleotide probes have differing target-specific portions which hybridize to a given allele in a base-specific manner, wherein, in said detecting, the labels of ligated product sequences of each group, captured on the solid support at different sites, are detected, thereby indicating a presence, in the sample, of one or more allele differences selected from the group consisting of insertions, deletions, microsatellite repeats, translocations, and other DNA rearrangements in one or more target nucleotide sequences.

19. A method according to claim 1, wherein the oligonucleotide probe sets are designed for distinguishing multiple allele differences selected from the group consisting of insertions, deletions, and microsatellite repeats, at one or more nucleotide positions which require overlapping oligonucleotide probe sets, wherein, in the oligonucleotide probe sets of each group, the second oligonucleotide probes have a common target-specific portion, and the first oligonucleotide probes have differing target-specific portions which contain repetitive sequences of different lengths to hybridize to a given allele in a base-specific manner.

20. A method according to claim 1, wherein a low abundance of multiple allele differences at multiple adjacent nucleotide positions, or at nucleotide positions which require overlapping oligonucleotide probe sets, in a single target nucleotide sequence, in the presence of an excess of normal sequence, or a low abundance of multiple allele differences at multiple nucleotide positions which require overlapping oligonucleotide probe sets, in multiple target nucleotide sequences, in the presence of an excess of normal sequence, are distinguished, the oligonucleotide probe sets forming a plurality of oligonucleotide probe groups, each group comprised of one or more oligonucleotide probe sets designed for distinguishing multiple allele differences at a single nucleotide position, wherein one or more sets within a group share common second oligonucleotide probes and the first oligonucleotide probes have differing target-specific portions which hybridize to a given allele excluding the normal allele in a base-specific manner, wherein, in said detecting, the labels of ligated product sequences of each group captured on the solid support at different sites, are detected, thereby indicating a presence, in the sample, of one or more low abundance alleles at one or more nucleotide positions in one or more target nucleotide sequences.

21. A method according to claim 20, wherein the oligonucleotide probes in a set are suitable for ligation together at a ligation junction when hybridized adjacent to one another on a corresponding target nucleotide sequence due to perfect complementarity at the ligation junction, but, when the oligonucleotide probes in the set are hybridized to any-other nucleotide sequence present in the sample, the first oligonucleotide probes have a mismatch at a base at the ligation junction which interferes with such ligation.

22. A method according to claim 21, wherein a low abundance of multiple allele differences at multiple adjacent nucleotide positions, or at nucleotide positions which require overlapping oligonucleotide probe sets, in a single target nucleotide sequence, in the presence of an excess of normal sequence, or a low abundance of multiple allele differences at multiple nucleotide positions which require overlapping oligonucleotide probe sets in multiple target nucleotide sequences, in the presence of an excess of normal sequence, are quantified in a sample, said method further comprising:

providing a known amount of one or more marker target nucleotide sequences;

providing a plurality of marker-specific oligonucleotide probe sets, each set characterized by (a) a first oligonucleotide probe having a target-specific portion complementary to the marker target nucleotide sequence and an addressable array-specific portion, and (b) a second oligonucleotide probe, having a target-specific portion complementary to the marker target nucleotide sequence and a detectable reporter label, wherein the oligonucleotide probes in a particular marker-specific oligonucleotide set are suitable for ligation together when hybridized adjacent to one another on a corresponding marker target nucleotide sequence, but, when hybridized to any other nucleotide sequence present in the sample or added marker sequences, have a mismatch which interferes with such ligation;

providing a plurality of oligonucleotide probe groups, each group comprised of one or more oligonucleotide probe sets or marker-specific oligonucleotide probe sets designed for distinguishing multiple allele differences at a single nucleotide position, including marker nucleotide sequences, wherein one or more sets within a group share a common second oligonucleotide probe and the first oligonucleotide probes have different target-specific probe portions which hybridize to a given allele or a marker nucleotide sequence excluding the normal allele, in a base-specific manner, wherein said blending comprises blending the sample, the marker target nucleotide sequences, the plurality of oligonucleotide probe sets, the plurality of marker-specific oligonucleotide probe sets, and the ligase to form a mixture;

detecting the reporter labels of the ligated marker-specific oligonucleotide sets captured on the solid support at particular sites, thereby indicating the presence of one or more marker target nucleotide sequences in the sample; and quantifying the amount of target nucleotide sequences in the sample by comparing the amount of captured ligated products generated from the known amount of marker target nucleotide sequences with the amount of other captured ligated product generated from the low abundance unknown sample.

23. A method according to claim 22, wherein the oligonucleotide probes in a set are suitable for ligation together at a ligation junction when hybridized adjacent to one another on a corresponding target nucleotide sequence under selected conditions due to perfect complementarity at the ligation junction, but, when the oligonucleotide probes in the set are hybridized to any other nucleotide sequence present in the sample, the first oligonucleotide probes have a mismatch at a base at the ligation junction which interferes with such ligation.

24. A method according to claim 1, wherein multiple allele differences at one or more nucleotide position in a single target nucleotide sequence or multiple allele differences at one or more positions in multiple target nucleotide sequences are distinguished, the oligonucleotide sets forming a plurality of oligonucleotide probe groups, each group comprised of one or more oligonucleotide probe sets designed for distinguishing multiple allele differences at a single nucleotide position, wherein, in the oligonucleotide probes of each group, the first oligonucleotide probes have a common target-specific portion and the second oligonucleotide probes have differing target-specific portions which hybridize to a given allele in a base-specific manner, wherein, in said detecting, different reporter labels of ligated product sequences of each group captured on the solid support at particular sites are detected, thereby indicating a presence, in the sample, of one or more allele at one or more nucleotide positions in one or more target nucleotide sequences.

25. A method according to claim 24, wherein the oligonucleotide probes in a set are suitable for ligation together at a ligation junction when hybridized adjacent to one another on a corresponding target nucleotide sequence due to perfect complementarity at the ligation junction, but, when the oligonucleotide probes in the set are hybridized to any other nucleotide sequence present in the sample, the second oligonucleotide probes have a mismatch at a base at the ligation junction which interferes with such ligation.

26. A method according to claim 24, wherein multiple allele differences at two or more adjacent nucleotide positions, or at nucleotide positions which require overlapping oligonucleotide probe sets, in a single target nucleotide sequence, or multiple allele differences at two or more adjacent nucleotide positions, or at nucleotide positions which require overlapping oligonucleotide probe sets, in multiple target nucleotide sequences are distinguished, the oligonucleotide probe groups containing oligonucleotide probes with target-specific portions which overlap.

27. A method according to claim 26, wherein the oligonucleotide probes in a set are suitable for ligation together at a ligation junction when hybridized adjacent to one another on a corresponding target nucleotide sequence due to perfect complementarity at the ligation junction, but, when the oligonucleotide probes in the set are hybridized to any other nucleotide sequence present in the sample, the second oligonucleotide probe has a mismatch at a base at the ligation junction which interferes, with such ligation.

28. A method according to claim 1, wherein multiple allele differences at one or more nucleotide position in a single target nucleotide sequence or multiple allele differences at one or more positions in multiple target nucleotide sequences are distinguished, the oligonucleotide sets forming a plurality of probe groups, each group comprised of one or more oligonucleotide probe sets designed for distinguishing multiple allele differences at a single nucleotide position, wherein, in the oligonucleotide probes of different groups, the second oligonucleotide probes have a common target-specific portion or the first oligonucleotide probes have a common target-specific portion, wherein, in said detecting, the one of a plurality of labeled ligated product sequences of each group captured on the solid support at particular sites are detected, thereby indicating a presence of one or more allele at one or more nucleotide positions in one or more target nucleotide sequences in the sample.

29. A method according to claim 28, wherein the oligonucleotide probes in a given set are suitable for ligation together at ligation junction when hybridized adjacent to one another on a corresponding target nucleotide sequence due to perfect complementarity at the ligation junction but, when the oligonucleotides in the set are hybridized to any other nucleotide sequence present in the sample, the first or second oligonucleotide probes have a mismatch at a base at the ligation junction which interferes with such ligation.

30. A method according to claim 28, wherein multiple allele differences at two or more adjacent nucleotide positions, or at nucleotide positions which require overlapping oligonucleotide probe sets, in a target nucleotide sequence or multiple allele differences at two or more adjacent nucleotide positions, or at nucleotide positions which require overlapping oligonucleotide probe sets, in multiple target nucleotide sequence are distinguished, the oligonucleotide probe groups containing probes with target-specific portions which overlap.

31. A method according to claim 30, wherein oligonucleotide probes in a set are suitable for ligation together at a ligation junction when hybridized adjacent to one another on a corresponding target nucleotide sequence due to perfect complementarity at the ligation junction, but, when the oligonucleotides in the set are hybridized to any other nucleotide sequence present in the sample, the first or second oligonucleotide probes have a mismatch at a base at the ligation junction which interferes with such ligation.

32. A method according to claim 29, wherein all possible single-base mutations for a single codon in a single target nucleotide sequence, all possible single-base mutations for multiple codons in a single target nucleotide sequence, and all possible single-base mutations for multiple codons in multiple target nucleotide sequences are distinguished, the oligonucleotide sets forming a plurality of oligonucleotide probe groups, each group comprised of one or more oligonucleotide probe sets designed for distinguishing all possible single-base mutations for a single codon, wherein, in the oligonucleotide probes of each group, the second oligonucleotide probes differ only in their 5' bases at their ligation junction and contain different reporter labels, the first oligonucleotide probes differ only in their 3' bases at their ligation junction and contain different addressable array-specific portions, or the first oligonucleotide probes differ only in their 3' bases adjacent to the base at the ligation junction and contain different addressable array-specific portions.

33. A method according to claim 29, wherein the oligonucleotide probes in a set are suitable for ligation together at a ligation junction when hybridized adjacent to one another on a corresponding target nucleotide sequence due to perfect complementarity at the ligation junction, but, when the oligonucleotides in the set are hybridized to any other nucleotide sequence present in the sample, the first oligonucleotide probes have a mismatch at the 3' base at the ligation junction or the 3' base adjacent the base at the ligation junction or the second oligonucleotide probes have a mismatch at the 5' base at the ligation junction which interferes with such ligation.

34. A method according to claim 33, wherein all possible single-base mutations for a single codon in a single target nucleotide sequence, or all possible single-base mutations for two or more adjacent codons, or at nucleotide positions which require overlapping oligonucleotide probe sets, in multiple target nucleotide sequences are distinguished, the oligonucleotide probe groups containing oligonucleotide probes with target-specific portions which overlap.

35. A method according to claim 1, wherein the denaturation treatment is at a temperature of about 80°–105° C.

36. A method according to claim 1, wherein each cycle, comprising a denaturation treatment and a hybridization treatment, is from about 30 seconds to about five minutes long.

37. A method according to claim 1, wherein said subjecting is repeated for 2 to 50 cycles.

38. A method according to claim 1, wherein total time for said subjecting is 1 to 250 minutes.

39. A method according to claim 1, wherein the ligase is selected from the group consisting of *Thermus aquaticus* ligase, *Thermus thermophilus* ligase, *E. coil* ligase, T4 ligase, Thermus sp. AK16 ligase, *Aquifex aeolicus* ligase, *Thermotoga maritima* ligase, and Pyrococcus ligase.

40. A method according to claim 1, wherein the detectable reporter label is selected from the group consisting of chromophores, fluorescent moieties, enzymes, antigens, heavy metals, magnetic probes, dyes, phosphorescent groups, radioactive materials, chemiluminescent moieties, and electrochemical detecting moieties.

41. A method according to claim 1, wherein the target-specific portions of the oligonucleotide probes each have a hybridization temperature of 40–85° C.

42. A method according to claim 1, wherein the target-specific portions of the oligonucleotide probes are 20 to 28 nucleotides long.

43. A method according to claim 1, wherein the mixture further includes a carrier DNA.

44. A method according to claim 1, wherein said subjecting the mixture to one or more ligation detection reaction cycles achieves a rate of formation of mismatched ligation products that is less than 0.005 of the rate of formation of matched ligation products for a particular oligonucleotide probe set.

45. A method according to claim 1 further comprising:
    amplifying the target nucleotide sequences in the sample prior to said blending.

46. A method according to claim 45, wherein said amplifying is carried out by subjecting the sample to a polymerase-based amplifying procedure.

47. A method according to claim 45, wherein said polymerase-based amplifying procedure is carried out with DNA polymerase.

48. A method according to claim 1, wherein the solid support is made from a material selected from the group consisting of plastic, ceramic, metal, resin, gel, glass, silicon, and composites thereof.

49. A method according to claim 1, wherein said detecting step comprises:
    scanning the solid support at the particular sites and
    identifying if ligation of the oligonucleotide probe sets occurred and correlating identified ligation to a presence or absence of the target nucleotide sequences.

50. A method according to claim 1, wherein the plurality of capture oligonucleotides each have different nucleotide sequences.

51. A method according to claim 50, wherein each capture oligonucleotide differs from its adjacent capture oligonucleotide on the array by at least one out of every four of the total number of nucleotides when the oligonucleotides are aligned at one end with one another without internal insertion or deletion.

52. A method according to claim 50, wherein each capture oligonucleotide has adjacent capture oligonucleotides separated from adjacent capture oligonucleotides by barrier oligonucleotides to which ligated oligonucleotide probe sets will not hybridize during said contacting.

53. A method according to claim 1, wherein the oligonucleotide probe sets hybridize to the target nucleotide sequences at temperatures which are less than that at which the capture oligonucleotides hybridize to the addressable array-specific portion of oligonucleotide probe sets.

54. A method according to claim 1 further comprising:
treating the mixture chemically or enzymatically, after said subjecting the mixture to a series of ligase detection reaction cycles, to destroy unligated oligonucleotide probes.

55. A method according to claim 54, wherein said treating step is carried out with an exonuclease.

56. A method according to claim 1 further comprising:
removing oligonucleotides bound to the capture oligonucleotides to permit reuse of the solid support with immobilized capture oligonucleotides.

57. A method according to claim 1, wherein the solid support includes different capture oligonucleotides immobilized at different sites with different capture oligonucleotides being complementary to different addressable array-specific portions, whereby different oligonucleotide probe sets are captured and detected at different sites on the solid support.

58. A method according to claim 1, wherein the solid support includes identical capture oligonucleotides immobilized on the solid support with the capture oligonucleotides being complementary to all the addressable array-specific portions and the labels attached to the oligonucleotide probe sets being different, whereby the different oligonucleotide probe sets are detected and distinguished by the different labels.

59. A method according to claim 1, wherein the conditions effective to mask negative charges involves carrying out said contacting step in the presence of a divalent cation-containing compound.

60. A method according to claim 59, wherein the divalent cation is selected from the group consisting of $Mg^{+2}$, $Ca^{+2}$, $Mn^{+2}$, and $CO^{+2}$.

61. A method according to claim 60, wherein the divalent cation is $Mg^{+2}$.

62. A method according to claim 1, wherein the conditions effective to mask negative charges involves carrying out said contacting step at a pH at or below 6.0.

63. A method according to claim 1, wherein the conditions effective to mask negative charges involves capping free carboxylic acid groups with a neutralizing agent.

64. A method according to claim 63, wherein the neutralizing agent is selected from the group consisting of ethanolamine, diethanolamine, propanolamine, dipropanolamine, isopropanolamine, and diisopropanolamine.

65. A method according to claim 64, wherein the neutralizing agent is ethanolamine.

66. A method according to claim 1, wherein said contacting is carried out by mixing the mixture in the presence of the solid support.

67. A method according to claim 1, wherein the addressable array-specific portions are hybridized to the capture oligonucleotides, during said contacting, at a temperature of 60° C. to 70° C.

68. A method according to claim 1, wherein said detecting step indicates the presence of ligated product in a ratio to unligated oligonucleotide probes of less than 1:300.

69. A method according to claim 68, wherein said detecting step indicates the presence of ligated product in a ratio to unligated oligonucleotide probes of less than 1:900.

70. A method according to claim 69, wherein said detecting step indicates the presence of ligated product in a ratio to unligated oligonucleotide probes of less than 1:3000.

71. A method according to claim 70, wherein said detecting step indicates the presence of ligated product in a ratio to unligated oligonucleotide probes of less than 1:9000.

72. A method according to claim 1, wherein said detecting step indicates e presence of a target nucleotide sequence, which differs from a non-target nucleotide sequence by a single base difference, in a ratio of the target nucleotide sequence to non-target nucleotide sequence of less than 1:20.

73. A method according to claim 72, wherein said detecting step indicates the presence of a target nucleotide sequence, which differs from a non-target nucleotide sequence by a single base difference, in a ratio of the target nucleotide sequence to non-target nucleotide sequence of less than 1:50.

74. A method according to claim 73, wherein said detecting step indicates the presence of a target nucleotide sequence, which differs from a non-target nucleotide sequence by a single base difference, in a ratio of the target nucleotide sequence to non-target nucleotide sequence of less than 1:100.

75. A method according to claim 74, wherein said detecting step indicates the presence of a target nucleotide sequence, which differs from a non-target nucleotide sequence by a single base difference, in a ratio of the target nucleotide sequence to non-target nucleotide sequence of less than 1:200.

* * * * *

UNITED STATES PATENT AND TRADEMARK OFFICE
CERTIFICATE OF CORRECTION

PATENT NO. : 6,506,594 B1
DATED : January 14, 2003
INVENTOR(S) : Barany et al.

It is certified that error appears in the above-identified patent and that said Letters Patent is hereby corrected as shown below:

<u>Title page,</u>
Item [73], Assignee, Missing Assignee information should be -- Cornell Research Foundation, Inc., Ithaca, NY (US); Regents of the University of Minnesota, Minneapolis, MN (US); Board of Supervisors of Louisiana State University and Agricultural and Mechanical College, Baton Rouge, LA (US) --

Signed and Sealed this

Seventh Day of October, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,506,594 B1 | Page 1 of 1 |
| APPLICATION NO. | : 09/526992 | |
| DATED | : January 14, 2003 | |
| INVENTOR(S) | : Francis Barany | |

It is certified that error appears in the above-identified patent and that said Letters Patent is hereby corrected as shown below:

Col. 1 at lines 9-13, delete "This invention was developed with government funding under National Institutes of Health Grant Nos. GM-41337-06, GM-43552-05, GM-42722-07, and GM-51628-02, and NIST Grant No. 1995-08-0006F. The U.S. Government may have certain rights." and insert --This invention was made with government support under grants GM-41337-06, GM-43552-05, GM-42722-07, and GM-51628-02 awarded by National Institutes of Health and grant 1995-08-0006F awarded by NIST. The government has certain rights in the invention-- in its place.

Signed and Sealed this

Twenty-fourth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,506,594 B1 | Page 1 of 1 |
| APPLICATION NO. | : 09/526992 | |
| DATED | : January 14, 2003 | |
| INVENTOR(S) | : Francis Barany et al. | |

It is certified that error appears in the above-identified patent and that said Letters Patent is hereby corrected as shown below:

Col. 1 at lines 9-13, delete "This invention was made with government funding under grants GM-41337-06, GM-43552-05, GM-42722-07, and GM-51628-02 awarded by the National Institutes of Health, and grant 1995-08-0006F awarded by NIST. The government has certain rights in the invention." and insert --This invention was made with government support under grant GM-41337-06 awarded by National Institutes of Health and grant 1995-08-0006F awarded by NIST. The government has certain rights in the invention-- in its place.

Signed and Sealed this

Twenty-sixth Day of January, 2010

David J. Kappos
*Director of the United States Patent and Trademark Office*

```
                          SEQUENCE LISTING

<160> NUMBER OF SEQ ID NOS: 65

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
tgcgggtaca gcacctacct tgcg                                           24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
atcgggtagg taaccttgcg tgcg                                           24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
cagcggtaga ccacctatcg tgcg                                           24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
ggtaggtaac ctacctcagc tgcg                                           24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gaccggtatg cgacctggta tgcg                                           24
```

```
<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
atcgggtagg taaccttgcg tgcg                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ggtaggtaac ctacctcagc tgcg                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
atcgggtagg taaccttgcg tgcg                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ggtaggtaac ctacctcagc tgcg                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
atcgggtagg taaccttgcg tgcg                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
cagcacctga ccatcgatcg cagc                                              24
```

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
atcgggtagg taaccttgcg tgcg                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ggtaggtaac ctacctcagc tgcg                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
cgcacgcaag gttacctacc cgat                                            24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
cgcagctgag gtaggttacc tacc                                            24

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
cgcacgatag gtggtctacc gctgatataa acttgtgggg agctagtggc gtaggcaaga     60
gtgcc                                                                 65

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
ataaggcctg ctgaaaatga ctgaa                                           25
```

```
<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ctgcaccagt aaatatgcata ttaaaacaag                                              30

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
gctgaggtcg atgctgaggt cgcaaaactt gtggtagttg gagctgg                            47

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
gctgcgatcg atggtcaggt gctgaaactt gtggtagttg gagctga                            47

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
gctgtacccg atcgcaaggt ggtcaaactt gtggtagttg gagctgc                            47

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
cgcaaggtag gtgctgtacc cgcaaaactt gtggtagttg gagctgt                            47

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
tggcgtaggc aagagtgcct                                                          20
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
tggcgtaggc aagagtgcct                                              20

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
cgcacgatag gtggtctacc gctgatataa acttgtggta gttggagcta              50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
cgcacgatag gtggtctacc gctgatataa acttgtggta gttggagctc              50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
ggtcaggtta ccgctgcgat cgcaatataa acttgtggta gttggagctt              50

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
gtggcgtagg caagagtgcc                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gtggcgtagg caagagtgcc                                              20

```
<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ggtccgatta ccggtccgat gctgtgtggt agttggagct ggtga            45

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ggtctaccta cccgcacgat ggtctgtggt agttggagct ggtgg            45

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
cgtaggcaag agtgccttga c                                     21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
cgtaggcaag agtgccttga c                                     21

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
tgcgacctca gcatcgacct cagc                                  24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
cagcacctga ccatcgatcg cagc                                  24

<210> SEQ ID NO 36
```

```
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
gaccaccttg cgatcgggta cagc                                          24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
tgcgggtaca gcacctacct tgcg                                          24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
cagcggtaga ccacctatcg tgcg                                          24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
gaccggtatg cgacctggta tgcg                                          24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
tgcgatcgca gcggtaacct gacc                                          24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
cagcatcgga ccggtaatcg gacc                                          24

<210> SEQ ID NO 42
<211> LENGTH: 24
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
gaccatcgtg cgggtaggta gacc                                           24

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
tgtcccatct ggtaagtcag cacaaacgct gaggtcgatg ctgaggtgcg a             51

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
aacattaatg ctatgcagaa aatcttagag                                     30

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
gtcattaatg ctatgcagaa aatcttag                                       28

<210> SEQ ID NO 46
<211> LENGTH: 49
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
aggacagaaa ggtaaagctc cctccgctgc gatcgatggt caggtgctg               49

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
caaagcgagc aagagaatcc c                                              21

<210> SEQ ID NO 48
<211> LENGTH: 23
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 48
acaaagcgag caagagaatc ccc                                              23

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
ggaaaatctg tccaggtatc agatgctgta cccgatgcga aggtggtc                   48

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
caacttgtgg gatttttagc acagcaagt                                        29

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 51
tacttgtggg atttttagca cagcaag                                          27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
tgtcccatct ggtaagtcag cacaaac                                          27

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 53
gctggcgacg attaccaggt cgataacatt aatgctatgc agaaaatctt ag              52

<210> SEQ ID NO 54
<211> LENGTH: 50
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 54
gctggctgcg ataggtaggt taccgtcatt aatgctatgc agaaaatctt            50

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 55
aggacagaaa ggtaaagctc cctcc                                       25

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56
gcgagcgaag gttacctacc cgatcaaagc gagcaagaga atc                   43

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 57
gcgacgatag gtggtctacc gctgacaaag cgagcaagag aatcc                 45

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 58
ggaaaatctg tccaggtatc agat                                        24

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 59
gcgagctgag gtaggttacc tacccaactt gtgggatttt tagcacagca a          51

<210> SEQ ID NO 60
<211> LENGTH: 49
<212> TYPE: DNA
<213> ORGANISM: Artificial Sequence
<220> FEATURE:
```

```
<223> OTHER INFORMATION: Description of Artificial Sequence:
      oligonucleotide

<400> SEQUENCE: 60
gcgataccag gtgcgatacc ggtctacttg tgggattttt agcacagca              49

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 61
tcgcacctca gcatcgacct cagc                                        24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 62
atcgacctgg taatcgtcgc cagc                                        24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 63
cagcacctga ccatcgatcg cagc                                        24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 64
ggtaacctac ctatcgcagc cagc                                        24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 65
gaccaccttc gcatcgggta cagc                                        24
```